(12) United States Patent
Haley et al.

(10) Patent No.: US 7,951,549 B2
(45) Date of Patent: May 31, 2011

(54) METHODS FOR THE IDENTIFICATION OF AGENTS THAT INHIBIT MESENCHYMAL-LIKE TUMOR CELLS OR THEIR FORMATION

(75) Inventors: John D. Haley, Sea Cliff, NY (US); Stuart Thomson, Port Washington, NY (US); Julie Kan, Smithtown, NY (US); Salam A. Shaaban, Westborough, MA (US)

(73) Assignee: OSI Pharmaceuticals, Inc., Ardsley, NY (US)

( * ) Notice: Subject to any disclaimer, the term of this patent is extended or adjusted under 35 U.S.C. 154(b) by 3 days.

(21) Appl. No.: 12/381,082

(22) Filed: Mar. 6, 2009

(65) Prior Publication Data

US 2009/0226396 A1    Sep. 10, 2009

Related U.S. Application Data

(60) Provisional application No. 61/068,612, filed on Mar. 7, 2008.

(51) Int. Cl.
*G01N 33/574* (2006.01)
*C12Q 1/02* (2006.01)

(52) U.S. Cl. ......................................... 435/7.23; 435/29

(58) Field of Classification Search ........................ None
See application file for complete search history.

(56) References Cited

U.S. PATENT DOCUMENTS

| 2006/0211060 A1 | 9/2006 | Haley |
| 2007/0065858 A1 | 3/2007 | Haley |
| 2007/0212738 A1 | 9/2007 | Haley |
| 2008/0312260 A1 | 12/2008 | Haley |

FOREIGN PATENT DOCUMENTS

| WO | 2005/070020 A2 | 8/2005 |
| WO | 2005/117553 A2 | 12/2005 |

OTHER PUBLICATIONS

AACR Special Conference :Frontiers in Cancer Prevention Research, EMT: The basis for the design of rational drug combinations, Nov. 12-15, 2006, presented by OSI Pharmaceuticals, Boston, MA.
Avizienyte, E. et al. (2005) Current Opinion in Cell Biology 17:542-547.
Ayrault, O. et al. (2006) Experimental Cell Research 312(7):1185-1193.
Bailey, K.M. et al. (2008) The Journal of Biological Chemistry 283 (20):13714-13724.
Bartling, B. et al. (2006) Am J Respir Cell Mol Biol 34:83-91.
Bartling, B. et al. (2005) Carcinogenesis 26 (2):293-301, 2005.
Benavente, S. et al., AACR 2006, Department of Human Oncology, University of Wisconsin School of Medicine and Public Health, Madison, Wisconsin, abstract #1246 *www.humonc.wisc.edu/labs/hararilab.
Brown, K.A. (2004) Breast Cancer Research 6(3): R215-R231.
Buck, E. et al. (2007) Mol Cancer Ther 6(2):532-541.
Cano, A. et al. (2000) 82 Nature Cell Biology 2:76-83.
Carrozzino, F. et al. (2005) Am J Physiol Cell Physiol 289:1002-1014.
Cicchini, C. et al. (2008) Experimental Cell Research 314:143-152.
Comoglio, P.M. et al. (1996) Genes to Cells 1, 347-354.
Demir, A. et al. (2005) Cell Tissue Res 322:299-311.
Elshamy, W.M. (2005) Cancer Therapy 3:443-460.
Farahani, R.M.Z., Letters to the Editor, Nov. 30, 2006, Epithelial-Mesenchymal Transition: A Potential Therapeutic Goal for Prevention of Wound Fibrosis? Journal of Burns and Wounds, pp. 72-74.
Federick, B.A. et al. (Jun. 2007) Mol Cancer Ther 6(6):1683-1691.
Fuchs, B.C. et al. Cancer Res 2008; 68(7):2391-2399.
Grande, M. et al. (2002) Journal of Cell Science 115:4227-4236.
Grille, S.J. et al. (2003) Cancer Research 63, 2172-2178.
Grunert, S. et al (2003) Nature Reviews, Molecular Cell Biology 4:657-665.
Guaita, S. et al. (2002) The Journal of Biological Chemistry 277 (42):39209-39216.
Hugo, H. et al. (2007) J. Cell Physiol. 243:374-383.
Hurteau, G. J. et al. (2007) Cancer Res 67(17):7972-7976.
ISR and Written Opinion of the International Search Authority in PCT/US2009/001456.
Janda, E. et al. (2002) The Journal of Cell Biology, Jan. 21, 2002, 156(2): 299-313 *downloaded from www.jcb.org on Mar. 7, 2005.
Jiao, W. et al. (2002) British Journal of Cancer 86:98-101.
Kalluri, R. et al. (2003) J. Clin. Invest. 112(12):1776-1784.
Kanai, T. et al. (2000) British Journal of Cancer 82(10):1717-1723.
Kang, Y. et al. (2004) Cell 118:277-279.
Lee, J.M. et al. (2006) The Journal of Cell Biology, Mar. 27, 2006 172(7): 973-981 *downloaded from www.jcb.org on Feb. 11, 2007.
Lippman, S. M. et al. (2005) Clin Cancer Res 11(17):6097-6099.
Lu, Z. et al. (2003) Cancer Cell 4:499-515.
Luo, Y. et al. (2006) Chinese Medical Journal 119(9):713-718.
McMorrow, T. et al. (2005) Nephrol Dial Transplant 20: 2215-2225.
Mendici, D. et al. (2006) Molecular Biology of the Cell 17:1871-1879, Apr. 2006.
Okada, H. et al. (1997) The American Physiological Society F563-F574.

(Continued)

*Primary Examiner* — Robert Landsman
(74) *Attorney, Agent, or Firm* — Alexander A. Stewart; OSI Pharmaceuticals, Inc.

(57) ABSTRACT

The present invention provides tumor cell preparations for use as models of the EMT process for use in the identification of anti-cancer agents, wherein said tumor cell preparations comprise cells of the epithelial tumor cell line H358, which are stimulated by receptor ligands to induce EMT, or which have been engineered to inducibly express a protein that stimulates EMT. The present invention also provides methods of identifying potential anti-cancer agents by using such tumor cell preparations to identify agents that inhibit EMT, stimulate MET, or inhibit the growth of mesenchymal-like cells. Such agents should be particularly useful when used in conjunction with other anti-cancer drugs such as EGFR and IGF-1R kinase inhibitors, which appear to be less effective at inhibiting tumor cells that have undergone an EMT.

93 Claims, 23 Drawing Sheets
(6 of 23 Drawing Sheet(s) Filed in Color)

OTHER PUBLICATIONS

Oltean, S. et al., Sep. 19, 2006, PNAS 103(38):14116-14121.
Perez-Mancera, P.A. (2005) Human Molecular Genetics, 14 (22):3449-3461.
Perez-Soler, R. et al. (2003) Lung Cancer 41(suppl 2):S72, Abstract O-247.
Prindull, G. et al. (2004) Blood 103(8): 2892-2899.
Radisky, D.C. et al. (2005) Journal of Cell Science 118, 4325-4326.
Sabbah, M. et al. (2008) Drug Resistance Updates 11:123-151.
Savenger, P. et al. (1994) Molecular Biology of the Cell 5:851-862.
Shaaban, S. et al., 98th AACR Annual Meeting Apr. 14-18, 2007.
Shintani, Y. et al. (2008) Am J Respir Cell Mol Biol vol. 38:95-104.
Shrader, M. et al. (2007) Mol Cancer Ther 6(1):277-285.
Sokol, J. P. et al. (2005) Breast Cancer Research 7:R844-R853.
Teng, Y. et al. (2007) The Journal of Clinical Investigation 117(2):304-306.
Thiery, J.P. (2006) Nature Molecular Cell Biology 7:131-142.
Thomson, S. et al. (2005) Cancer Res 65 (20):9455-9462.
Venkov, C.D. et al. (2007) The Journal of Clinical Investigation 117(2):482-491 *http://www.jci.org.
Witta, S.E et al (2006) Cancer Res 66 (2):944-950.
Witta, S.E. et al (2004) Pro Amer Assoc Cancer Res 45; AACR Meeting Abstracts online, Abstract #3671. *downloaded Jun. 20, 2007 from www.aacrmeetingabstracts.org.
Yan, W. et al. (2006) The Journal of Biological Chemistry 281(28):19700-19708.
Yauch, R.L. et al. (2005) Clin Cancer Res 11(24) 8686-8698.
Zavadil, J. et al. (2005) Oncogene 24:5764-5774.
Khoury, H. et al. (2005) Molecular Biology of the Cell 16:550-561.
Brabletz, T. et al. (2005) Cells Tissues Organs 179:56-65.
Christiansen, J. et al. (2006) Cancer Res 66(17):8319-8326.
Christofori, G. (2006) Nature 441:444-450.
Leivonen, S. et al.(2007) Int. J. Cancer 121:2119-2124.
Moreno-Bueno, G. et al. (2008) Oncogene 27:6958-6969.
Nawshad, A. et al. (2005) Cells Tissues Organs 179:11-13.
Pardali, K. et al . (2007) Biochimica et Biophysica ACTA 1775:21-62.
Rees, J.R.E. et al. (2006) Cancer Res 66(19):9583-9590.
Savenger, P. et al. (2001) Bioassays 23: 912-923.
Tarin, D. (2005) Cancer Res 65(14):5996-6001.
Wang, D. et al. (2004) Oncogene 23:1668-1680.
Dumont, N. et al. (2003) Cancer Cell 3:531-536.
Huber, M.A. et al. (2005) Current Opinion in Cell Biology 17:548-558.
Thiery, J.P. (2002) Nature 2:442-454 *www.nature.com/reviews/cancer.

Figure 1. H358 cells were treated with growth factor and cytokines for 7 days and protein markers of EMT measured.
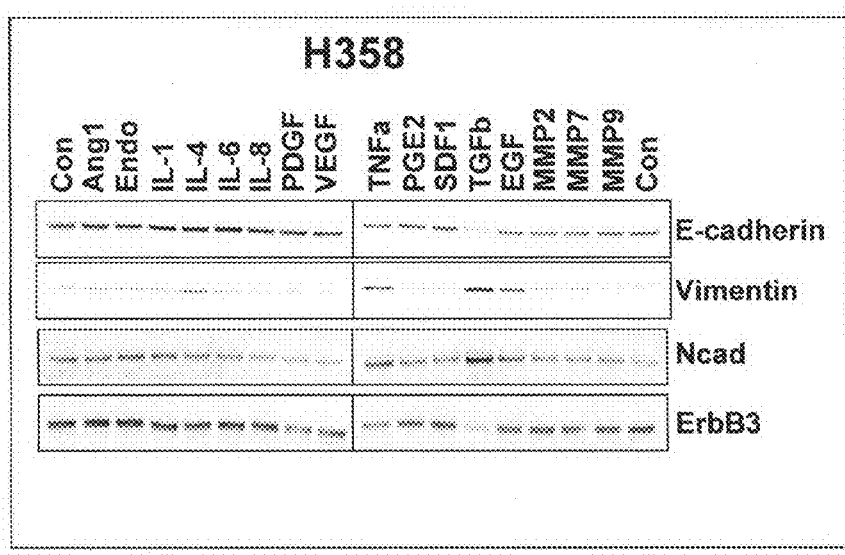

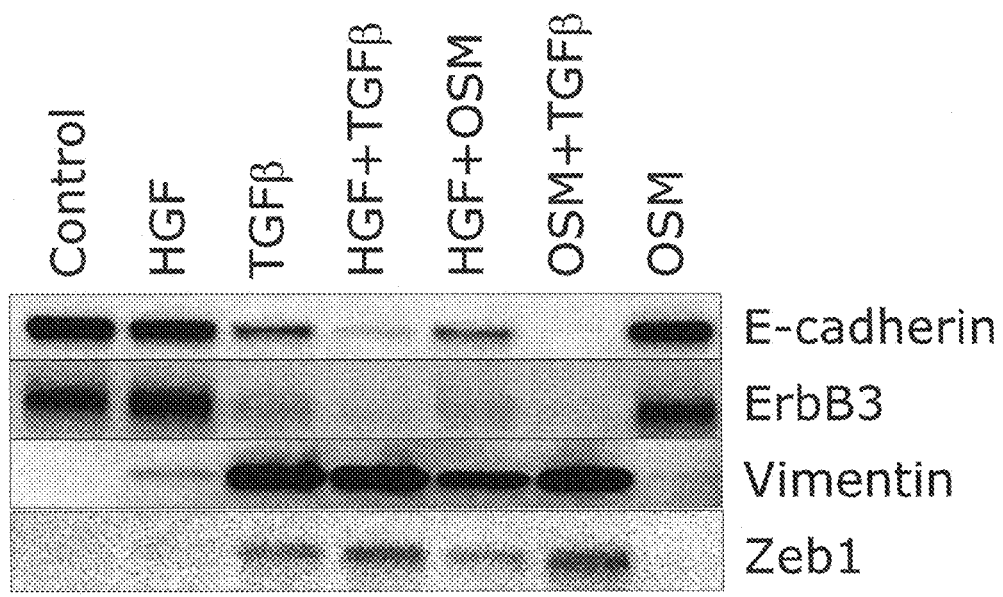
Figure 2: Western analysis of H358 cells treated with ligands as shown.

Figure 3. Schema used for development of tet-inducible EMT models suitable for in vivo imaging of primary and metastatic growth.
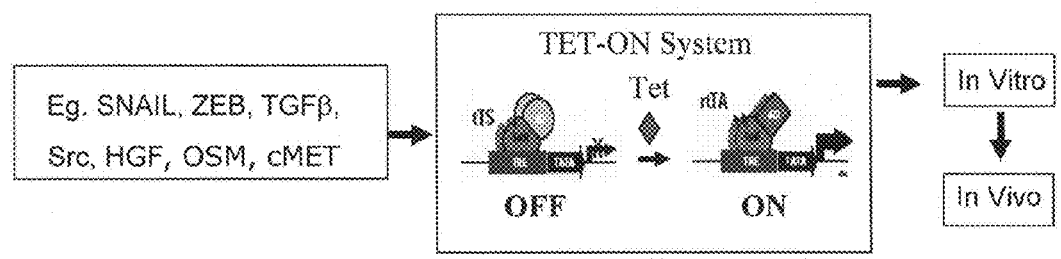

Figure 4. Doxycyclin dependent EMT-like transitions induced by Snail and Zeb expression in H358 cells, showing morphological (left panels) and marker changes (right panels) consistent with EMT.
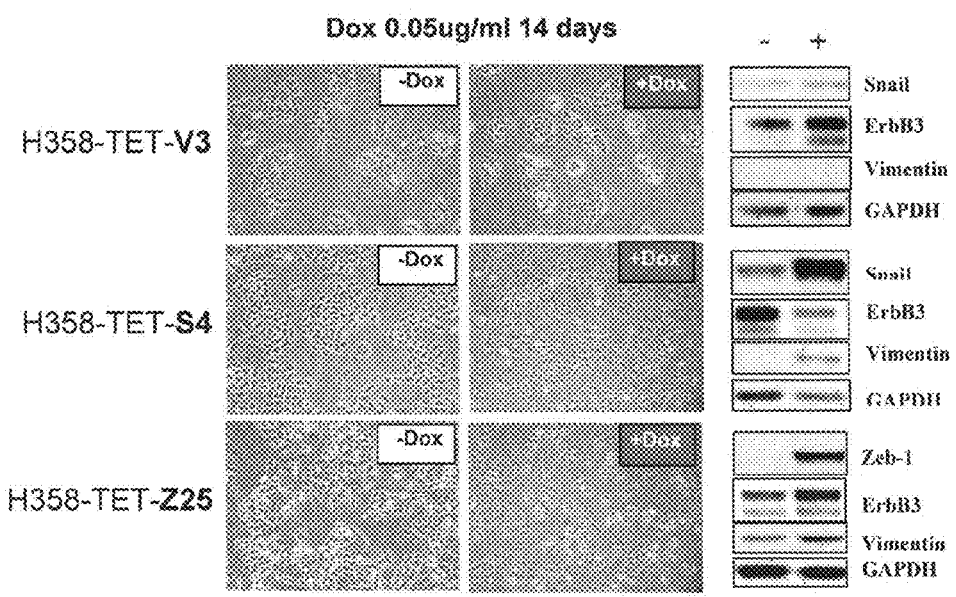

Figure 5. These changes in EMT marker expression and phenotype were found to be dose dependent on doxycyclin over 7 days of treatment.
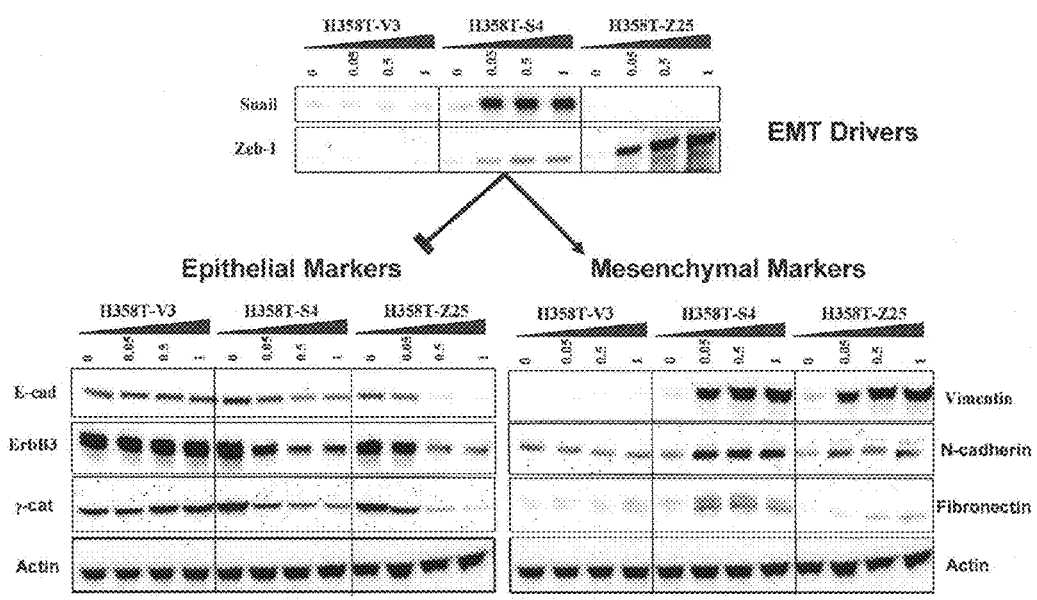

Figure 6: EMT induced by dox-inducible autocrine secretion of TGFβ in H358 cells
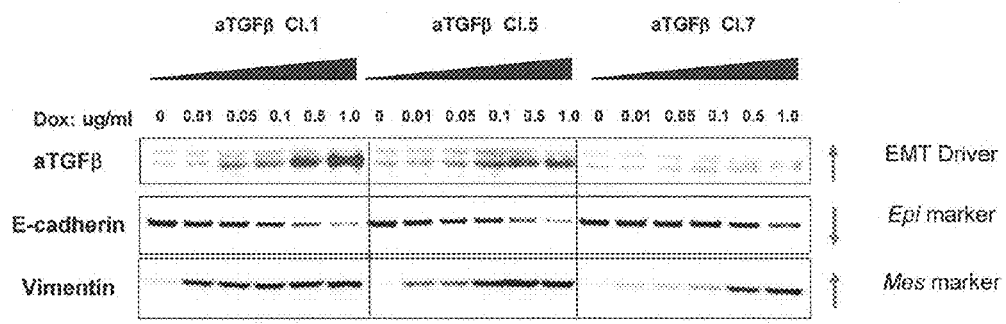

Figure 7A. Imaging of EMT using a mesenchymal-specific promoter (eg. vimentin) follwing doxycyclin induction of Snail.
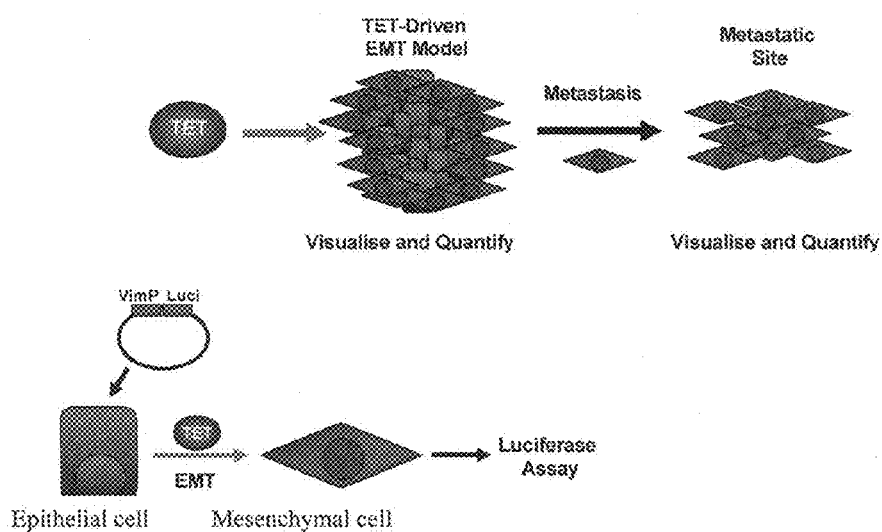
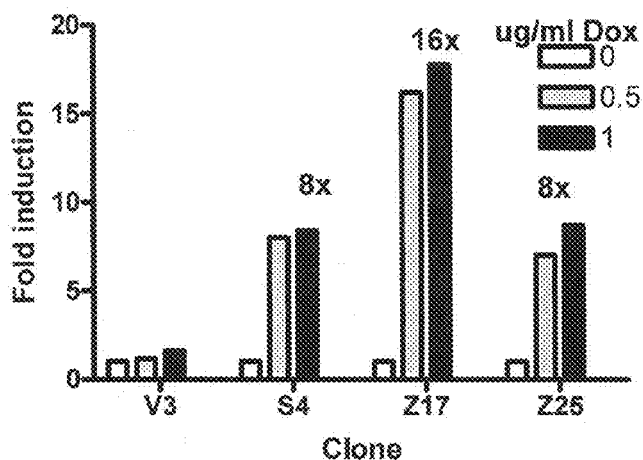
Figure 7B

Figure 8: Imaging of H358 luciferase expressing cells *in vivo*
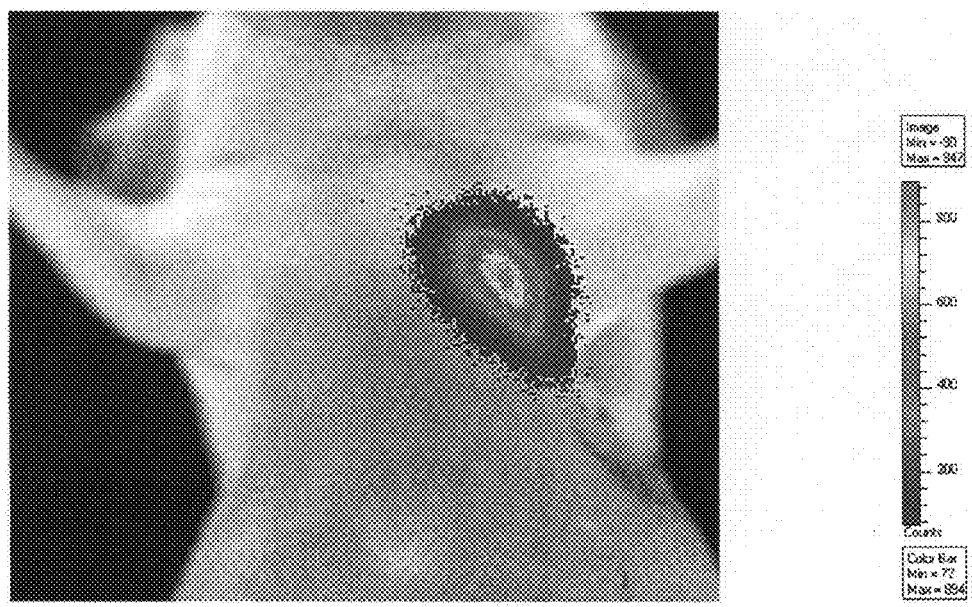

Figure 10: EMT ligands induce changes to E-cadherin and vimentin.
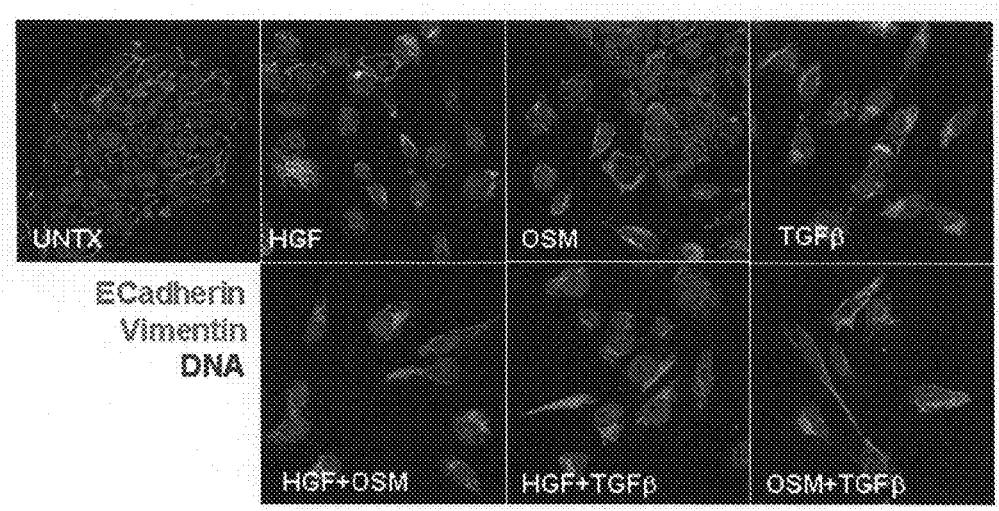

Figure 11B, continued
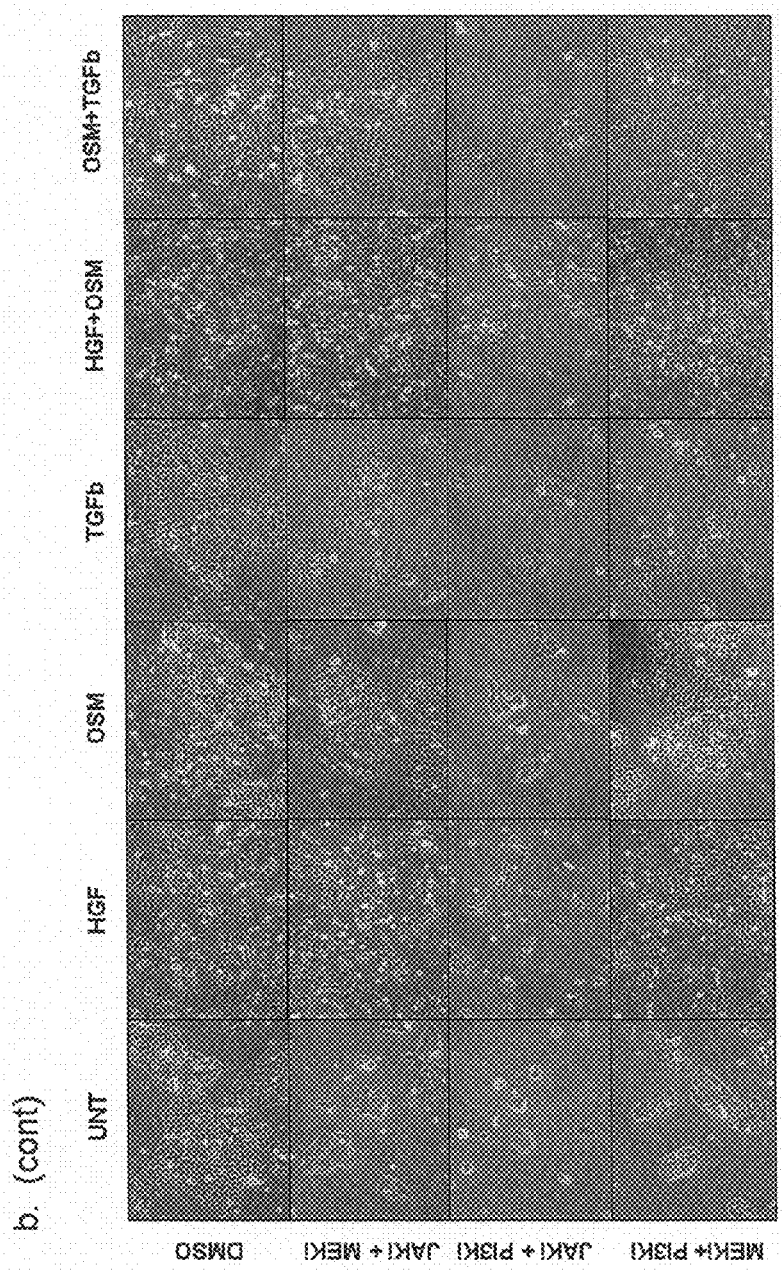

Figure 15
A 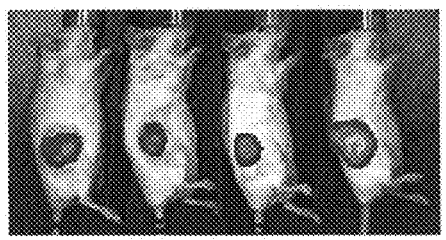 B 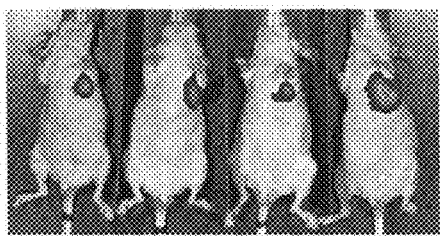

METHODS FOR THE IDENTIFICATION OF AGENTS THAT INHIBIT MESENCHYMAL-LIKE TUMOR CELLS OR THEIR FORMATION

CROSS-REFERENCE TO RELATED APPLICATIONS

This application claims the benefit of U.S. Provisional Application No. 61/068,612, filed Mar. 7, 2008, which is herein incorporated by reference in its entirety.

BACKGROUND OF THE INVENTION

The present invention is directed to EMT cell models and methods for their use in the identification of new anti-cancer agents for treating cancer patients, particularly in combination with other agents such as EGFR or IGF-1R kinase inhibitors that can be less effective at inhibiting tumor cells that have undergone an EMT. Cancer is a generic name for a wide range of cellular malignancies characterized by unregulated growth, lack of differentiation, and the ability to invade local tissues and metastasize. These neoplastic malignancies affect, with various degrees of prevalence, every tissue and organ in the body.

An anti-neoplastic drug would ideally kill cancer cells selectively, with a wide therapeutic index relative to its toxicity towards non-malignant cells. It would also retain its efficacy against malignant cells, even after prolonged exposure to the drug. Unfortunately, none of the current chemotherapies possess such an ideal profile. Instead, most possess very narrow therapeutic indexes. Furthermore, cancerous cells exposed to slightly sub-lethal concentrations of a chemotherapeutic agent will very often develop resistance to such an agent, and quite often cross-resistance to several other antineoplastic agents as well.

A multitude of therapeutic agents have been developed over the past few decades for the treatment of various types of cancer. The most commonly used types of anticancer agents include: DNA-alkylating agents (e.g., cyclophosphamide, ifosfamide), antimetabolites (e.g., methotrexate, a folate antagonist, and 5-fluorouracil, a pyrimidine antagonist), microtubule disrupters (e.g., vincristine, vinblastine, paclitaxel), DNA intercalators (e.g., doxorubicin, daunomycin, cisplatin), and hormone therapy (e.g., tamoxifen, flutamide). More recently, gene targeted therapies, such as protein-tyrosine kinase inhibitors have increasingly been used in cancer therapy (de Bono J. S. and Rowinsky, E. K. (2002) Trends in Mol. Medicine 8:S19-S26; Dancey, J. and Sausville, E. A. (2003) Nature Rev. Drug Discovery 2:92-313). Such approaches, such as the EGFR kinase inhibitor erlotinib, are generally associated with reduced toxicity compared with conventional cytotoxic agents. They are therefore particularly appropriate for use in combination regimens. In pancreatic cancer, phase III trials have shown that first-line erlotinib treatment in combination with gemcitabine improves survival.

The epidermal growth factor receptor (EGFR) family comprises four closely related receptors (HER1/EGFR, HER2, HER3 and HER4) involved in cellular responses such as differentiation and proliferation. Over-expression of the EGFR kinase, or its ligand TGF-alpha, is frequently associated with many cancers, including breast, lung, colorectal, ovarian, renal cell, bladder, head and neck cancers, glioblastomas, and astrocytomas, and is believed to contribute to the malignant growth of these tumors. A specific deletion-mutation in the EGFR gene (EGFRvIII) has also been found to increase cellular tumorigenicity. Activation of EGFR stimulated signaling pathways promote multiple processes that are potentially cancer-promoting, e.g. proliferation, angiogenesis, cell motility and invasion, decreased apoptosis and induction of drug resistance. Increased HER1/EGFR expression is frequently linked to advanced disease, metastases and poor prognosis. For example, in NSCLC and gastric cancer, increased HER1/EGFR expression has been shown to correlate with a high metastatic rate, poor tumor differentiation and increased tumor proliferation.

Mutations which activate the receptor's intrinsic protein tyrosine kinase activity and/or increase downstream signaling have been observed in NSCLC and glioblastoma. However the role of mutations as a principle mechanism in conferring sensitivity to EGF receptor inhibitors, for example erlotinib (TARCEVA®) or gefitinib (IRESSA™), has been controversial. Recently, a mutant form of the full length EGF receptor has been reported to predict responsiveness to the EGF receptor tyrosine kinase inhibitor gefitinib (Paez, J. G. et al. (2004) Science 304:1497-1500; Lynch, T. J. et al. (2004) N. Engl. J. Med. 350:2129-2139). Cell culture studies have shown that cell lines which express the mutant form of the EGF receptor (i.e. H3255) were more sensitive to growth inhibition by the EGF receptor tyrosine kinase inhibitor gefitinib, and that much higher concentrations of gefitinib was required to inhibit the tumor cell lines expressing wild type EGF receptor. These observations suggests that specific mutant forms of the EGF receptor may reflect a greater sensitivity to EGF receptor inhibitors, but do not identify a completely non-responsive phenotype.

Erlotinib (e.g. erlotinib HCl, also known as TARCEVA® or OSI-774) is an orally available inhibitor of EGFR kinase. In vitro, erlotinib has demonstrated substantial inhibitory activity against EGFR kinase in many human tumor cell lines. In a phase III trial, erlotinib monotherapy significantly prolonged survival, delayed disease progression and delayed worsening of lung cancer-related symptoms in patients with advanced, treatment-refractory NSCLC (Shepherd, F. et al. (2005) N. Engl. J. Med. 353(2):123-132). In November 2004 the U.S. Food and Drug Administration (FDA) approved TARCEVA® for the treatment of patients with locally advanced or metastatic non-small cell lung cancer (NSCLC) after failure of at least one prior chemotherapy regimen.

The development for use as anti-tumor agents of compounds that directly inhibit the kinase activity of IGF-1R, as well as antibodies that reduce IGF-1R kinase activity by blocking IGF-1R activation or antisense oligonucleotides that block IGF-1R expression, are also areas of intense research effort (e.g. see Larsson, O. et al (2005) Brit. J. Cancer 92:2097-2101; Ibrahim, Y. H. and Yee, D. (2005) Clin. Cancer Res. 11:944s-950s; Mitsiades, C. S. et al. (2004) Cancer Cell 5:221-230; Carmirand, A. et al. (2005) Breast Cancer Research 7:R570-R579 (DOI 10.1186/bcr1028); Carmirand, A. and Pollak, M. (2004) Brit. J. Cancer 90:1825-1829; Garcia-Echeverria, C. et al. (2004) Cancer Cell 5:231-239).

IGF-1R is a transmembrane RTK that binds primarily to IGF-1 but also to IGF-II and insulin with lower affinity. Binding of IGF-1 to its receptor results in receptor oligomerization, activation of tyrosine kinase, intermolecular receptor autophosphorylation and phosphorylation of cellular substrates (major substrates are IRS1 and Shc). The ligand-activated IGF-1R induces mitogenic activity in normal cells and plays an important role in abnormal growth. A major physiological role of the IGF-1 system is the promotion of normal growth and regeneration. Overexpressed IGF-1R (type 1 insulin-like growth factor receptor) can initiate mitogenesis and promote ligand-dependent neoplastic transformation. Furthermore, IGF-1R plays an important role in the establishment and maintenance of the malignant phenotype. Unlike the epidermal growth factor (EGF) receptor, no mutant oncogenic forms of the IGF-1R have been identified. However, several oncogenes have been demonstrated to affect IGF-1 and IGF-1R expression. The correlation between a reduction of IGF-1R expression and resistance to transformation has been seen. Exposure of cells to the mRNA antisense to IGF-1R RNA prevents soft agar growth of several human tumor cell lines. IGF-1R abrogates progression into apoptosis, both in vivo and in vitro. It has also been shown that a decrease in the level of IGF-1R below wild-type levels causes apoptosis of tumor cells in vivo. The ability of IGF-1R disruption to cause apoptosis appears to be diminished in normal, non-tumorigenic cells.

The IGF-1 pathway in human tumor development has an important role. IGF-1R overexpression is frequently found in various tumors (breast, colon, lung, sarcoma) and is often associated with an aggressive phenotype. High circulating IGF1 concentrations are strongly correlated with prostate, lung and breast cancer risk. Furthermore, IGF-1R is required for establishment and maintenance of the transformed phenotype in vitro and in vivo (Baserga R. *Exp. Cell. Res.*, 1999, 253, 1-6). The kinase activity of IGF-1R is essential for the transforming activity of several oncogenes: EGFR, PDGFR, SV40 T antigen, activated Ras, Raf, and v-Src. The expression of IGF-1R in normal fibroblasts induces neoplastic phenotypes, which can then form tumors in vivo. IGF-1R expression plays an important role in anchorage-independent growth. IGF-1R has also been shown to protect cells from chemotherapy-, radiation-, and cytokine-induced apoptosis. Conversely, inhibition of endogenous IGF-1R by dominant negative IGF-1R, triple helix formation or antisense expression vector has been shown to repress transforming activity in vitro and tumor growth in animal models.

During most cancer metastases, an important change occurs in a tumor cell known as the epithelial-mesenchymal transition (EMT) (Thiery, J. P. (2002) Nat. Rev. Cancer 2:442-454; Savagner, P. (2001) Bioessays 23:912-923; Kang Y. and Massague, J. (2004) Cell 118:277-279; Julien-Grille, S., et al. Cancer Research 63:2172-2178; Bates, R. C. et al. (2003) Current Biology 13:1721-1727; Lu Z., et al. (2003) Cancer Cell. 4(6):499-515)). EMT does not occur in healthy cells except during embryogenesis. Epithelial cells, which are bound together tightly and exhibit polarity, give rise to mesenchymal cells, which are held together more loosely, exhibit a loss of polarity, and have the ability to travel. These mesenchymal cells can spread into tissues surrounding the original tumor, as well as separate from the tumor, invade blood and lymph vessels, and travel to new locations where they divide and form additional tumors. Recent research has demonstrated that epithelial cells respond well to EGFR and IGF-1R kinase inhibitors, but that after an EMT the resulting mesenchymal-like cells are much less sensitive to such inhibitors. (e.g. Thompson, S. et al. (2005) Cancer Res. 65(20):9455-9462; U.S. Patent Application 60/997,514). Thus there is a pressing need for anti-cancer agents that can prevent or reverse tumor cell EMT events (e.g. stimulate a mesenchymal to epithelial transition (MET)), or inhibit the growth of the mesenchymal-like tumor cells resulting from EMT. Such agents should be particularly useful when used in conjunction with other anti-cancer drugs such as EGFR and IGF-1R kinase inhibitors.

As human cancers progress to a more invasive, metastatic state, multiple signaling programs regulating cell survival and migration programs are observed depending on cell and tissue contexts (Gupta, G. P., and Massague, J. (2006) Cell 127, 679-695). Recent data highlight the transdifferentiation of epithelial cancer cells to a more mesenchymal-like state, a process resembling epithelial-mesenchymal transition (EMT; (Oft, M., et al. (1996). Genes & development 10, 2462-2477; Perl, A. K., et al. (1998). Nature 392, 190-193), to facilitate cell invasion and metastasis (Brabletz, T. et al. (2005) Nat Rev Cancer 5, 744-749; Christofori, G. (2006) Nature 441, 444-450). Through EMT-like transitions mesenchymal-like tumor cells are thought to gain migratory capacity at the expense of proliferative potential. A mesenchymal-epithelial transition (MET) has been postulated to regenerate a more proliferative state and allow macrometastases resembling the primary tumor to form at distant sites (Thiery, J. P. (2002) Nat Rev Cancer 2, 442-454). EMT-like transitions in tumor cells result from transcriptional reprogramming over considerable periods of time (weeks to months) via transcription factors harboring zinc finger, forkhead, bHLH and HMG-box domains (Mani, S. A. et al. (2007) Proceedings of the National Academy of Sciences of the United States of America 104, 10069-10074; Peinado, H. et al. (2007) Nat Rev Cancer 7, 415-428). The loss of E-cadherin and transition to a more mesenchymal-like state likely serves a major role in the progression of cancer (Matsumura, T. et al. (2001) Clin Cancer Res 7, 594-599; Yoshiura, K. et al. (1995). Proceedings of the National Academy of Sciences of the United States of America 92, 7416-7419) and the acquisition of a mesenchymal phenotype has been correlated with poor prognosis (Baumgart, E. et al. (2007) Clin Cancer Res 13, 1685-1694; Kokkinos, M. I. Et al. (2007) Cells, tissues, organs 185, 191-203; Willipinski-Stapelfeldt, B. et al. (2005) Clin Cancer Res 11, 8006-8014.). Targeting tumor-derived and/or tumor-associated stromal cells provides a unique mechanism to block EMT-like transitions and inhibit the survival of invading cells.

The cellular changes associated with EMT-like transitions alter the dependence of carcinoma cells on EGF receptor signaling networks for survival. It has been observed that an EMT-like transition was associated with cellular insensitivity to the EGFR-TKI erlotinib (Thomson, S. et al. (2005) Cancer research 65, 9455-9462; Witta, S. E., et al. (2006) Cancer research 66, 944-950; Yauch, R. L., et al. (2005) Clin Cancer Res 11, 8686-8698), in part from EGFR independent activation of either or both the PI3'kinase or Mek-Erk pathways (Buck, E. et al. (2007). Molecular cancer therapeutics 6, 532-541). Similar data correlating EMT status to sensitivity to EGFR TKIs have been reported in pancreatic, CRC (Buck, E. et al. (2007) Molecular cancer therapeutics 6, 532-541) bladder (Shrader, M. et al. (2007) Molecular cancer therapeutics 6, 277-285) and HNSCC (Frederick et al. (2007) Molecular cancer therapeutics 6, 1683-1691) cell lines, xenografts and in patients (Yauch, R. L., et al. (2005) Clin Cancer Res 11, 8686-8698). The molecular determinants to alternative routes of activation of the PI3'kinase and Erk pathways, which can bypass cellular sensitivity to EGF receptor inhibitors, have been actively investigated (Chakravarti, A. et al. (2002) Cancer research 62, 200-207; Engelman, J. A. et al. (2007) Science 316:1039-1043).

Inhibition of EMT-like transitions and mesenchymal-like cell survival would be predicted to reduce tumor metastasis and progression. Current data suggest patients with metastasis have heterogeneous tumors that can contain cells with epithelial and mesenchymal-like phenotypes. The observation that tumors can acquire new signaling pathways, for example PDGFR and FGFR autocrine signaling, suggest new therapeutic modalities to target specific tumor cell populations. These data suggest rational drug combinations that would not only cause growth inhibition or apoptosis of tumor cells directly, but would also impact mesenchymal cell populations promoting cancer recurrence (Moody, S. E. et al. (2005). Cancer cell 8, 197-209). Essential for the discovery and development of such drug combinations will be the availability of good cellular and animal models where their efficacy can be readily assessed. The invention described herein provides such models.

SUMMARY OF THE INVENTION

The present invention provides a method of identifying an agent that inhibits tumor cells from undergoing an epithelial to mesenchymal transition, comprising contacting a sample of cells of the epithelial tumor cell line H358 with a test agent to be screened, contacting the sample with a single or dual protein ligand preparation that induces an epithelial-to-mesenchymal transition in H358 cells, determining whether the test agent inhibits the tumor cells in the sample from undergoing an epithelial to mesenchymal transition, by comparing the level of a biomarker whose level is indicative of the EMT status of the sample tumor cells to the level of the same biomarker in an identical sample of H358 cells not contacted with the test agent, and thus determining whether the test agent is an agent that inhibits tumor cells from undergoing an epithelial to mesenchymal transition. In one embodiment, the single protein ligand that induces an epithelial-to-mesenchymal transition in H358 cells is selected from EGF; TGFbeta; TNFalpha; and IL-4. In another embodiment, the dual protein ligands that induce an epithelial-to-mesenchymal transition in H358 cells are oncostatin-M plus HGF.

The present invention also provides a method of identifying an agent that inhibits tumor cells that have undergone an epithelial to mesenchymal transition, comprising contacting a sample of cells of the epithelial tumor cell line H358 with a single or dual protein ligand preparation to induce an epithelial-to-mesenchymal transition in the H358 cells, contacting the sample of cells with a test agent to be screened, determining whether the test agent inhibits mesenchymal-like H358 cell growth, and thus determining whether it is an agent that inhibits the growth of tumor cells that have undergone an epithelial to mesenchymal transition. In one embodiment, the single protein ligand that induces an epithelial-to-mesenchymal transition in H358 cells is selected from EGF; TGFbeta; TNFalpha; and IL-4. In another embodiment, the dual protein ligands that induce an epithelial-to-mesenchymal transition in H358 cells are oncostatin-M plus HGF.

The present invention also provides a method of identifying an agent that stimulates mesenchymal-like tumor cells to undergo a mesenchymal to epithelial transition, comprising contacting a sample of cells of the epithelial tumor cell line H358 with a single or dual protein ligand preparation to induce an epithelial-to-mesenchymal transition in the H358 cells, contacting the sample of cells with a test agent to be screened, determining whether the test agent stimulates the mesenchymal-like H358 cells in the sample to undergo a mesenchymal to epithelial transition, by comparing the level of a biomarker whose level is indicative of the EMT status of the sample tumor cells to the level of the same biomarker in an identical sample of mesenchymal-like H358 cells not contacted with the test agent, and thus determining whether the test agent is an agent that stimulates mesenchymal-like tumor cells to undergo a mesenchymal to epithelial transition. In one embodiment, the single protein ligand that induces an epithelial-to-mesenchymal transition in H358 cells is selected from EGF; TGFbeta; TNFalpha; and IL-4. In another embodiment, the dual protein ligands that induce an epithelial-to-mesenchymal transition in H358 cells are oncostatin-M plus HGF.

The present invention also provides a mesenchymal-like tumor cell preparation for use in the identification of anti-cancer agents, wherein said tumor cell preparation is prepared by a process comprising: contacting a sample of cells of the epithelial tumor cell line H358 with a single or dual protein ligand preparation to induce an epithelial-to-mesenchymal transition in the H358 cells, wherein the single protein ligand that induces an epithelial-to-mesenchymal transition in H358 cells is selected from EGF; TGFbeta; TNFalpha; and IL-4, and wherein the dual protein ligands that induce an epithelial-to-mesenchymal transition in H358 cells are oncostatin-M plus HGF.

The present invention also provides a tumor cell preparation for use in the identification of anti-cancer agents, wherein said tumor cell preparation comprises: a sample of cells of the epithelial tumor cell line H358, which have been engineered to inducibly express a protein that stimulates an epithelial to mesenchymal transition in H358 cells. The protein that is inducibly expressed and stimulates an epithelial to mesenchymal transition in H358 cells may be Snail, Zeb-1, or constitutively active TGF-beta. The present invention also provides methods of identifying potential anti-cancer agents by using such tumor cell preparations to identify agents that inhibit EMT, stimulate MET, or inhibit the growth of mesenchymal-like cells.

The present invention also provides methods for preparing compositions comprising agents identified by any of the methods described herein, to be used in the treatment of tumors or tumor metastases.

BRIEF DESCRIPTION OF THE FIGURES

The file of this patent contains at least one drawing executed in color. Copies of this patent with color drawing(s) will be provided by the Patent and Trademark Office upon request and payment of the necessary fee.

FIG. 1: Induction of EMT in H358 cells by growth factors and cytokines. H358 cells were treated with growth factors and cytokines for 7 days (see Materials abd Methods), and protein biomarkers of EMT, E-cadherin, vimentin, N-cadherin (Ncad) and erbB3 measured by immunoblotting of cell extracts. Growth factors included angiopoietin-1 (Ang1); Enodostatin (Endo); Interleukins-1, -4, -6, -8; platelet-derived growth factor (PDGF); vascular endothelial growth factor (VEGF); tumor necrosis factor alpha (TGFa); prostaglandin E2 (PGE2); stromal-derived factor-1 (SDF1), transforming growth factor beta (TGFb); epidermal growth factor (EGF); matrix metalloproteinases-2, -7, -9. Protein band density detected by immunoblot were compared to mock treated control (Con).

FIG. 2: Induction of EMT in H358 cells by multiple growth factors and cytokines. Immunoblotting analysis of protein biomarkers of EMT, E-cadherin, vimentin, ErbB3, and Zeb1 in lysates of H358 cells treated with ligands as shown.

FIG. 3: Schema used for development of tet-inducible EMT models suitable for in vivo imaging of primary and metastatic growth. EMT-inducing genes (Snail, Zeb, TGF-beta, Src, hepatocyte growth factor [HGF], oncostatin-M [OSM] and hepatocyte growth factor receptor [cMET]) were cloned into plasmids with promoter sequences designed to be expressed under the control of tetracyclines (e.g. doxycyclin). This allows for regulated EMT-inducing expression when tumor cells were grown as xenografts in vivo in immunocompromised mice.

FIG. 4: Doxycyclin dependent EMT-like transitions induced by Snail and Zeb expression in H358 cells, showing morphological (left panels) and biomarker changes (right panels) consistent with EMT. Protein biomarkers were analysed by immunoblotting analysis of ErbB3 and vimentin in lysates of H358 cells.

FIG. 5: Changes in EMT marker expression and phenotype induced by Snail and Zeb expression in H358 cells were found to be dose dependent on doxycycline over 7 days of treatment. The levels of transcriptional repressors snail and Zeb-1 were determined by immunoblotting analysis. Protein biomarkers of EMT were analysed by immunoblotting analysis of the epithelial biomarkers E-cadherin, erbB3, and gamma-catenin, and the mesenchymal biomarkers vimentin, N-cadherin, and fibronectin in lysates of H358 cells. Doxycycline concentration 0 to 1.0 µg/ml as indicated.

FIG. 6: EMT induced by dox-inducible autocrine secretion of TGFβ in H358 cells. The levels of EMT driver TGF-beta (constitutively active) were determined by immunoblotting analysis. Protein biomarkers of EMT were analysed by immunoblotting analysis of the epithelial (Epi) biomarker E-cadherin, and the mesenchymal (Mes) biomarker vimentin, in lysates of H358 cells. Doxycycline concentration 0 to 1.0 µg/ml as indicated.

FIGS. 7A-B: Imaging of EMT using a mesenchymal-specific promoter (vimentin) following doxycyclin induction of Snail. (A) Mesenchymal-specific promoter cells are useful in visualizing EMT in vivo both at the primary tumor site and metastatic sites, and important in measuring the activity in vivo of drugs which target EMT processes. (B) Cells induced to undergo EMT by expression of Snail (S4), Zeb1 (Z17 and Z25) were transfected with a vimentin promoter-luciferase plasmid and luciferase activity assayed. Cells induced to undergo EMT showed increased vimentin promoter activity than did vector control cells (V3). Transfections and luciferase assays were preformed using commercially available reagents using standard protocols.

FIG. 8: Imaging of H358 luciferase expressing cells in vivo. H358 cells expressing luciferase can be imaged using CCD cameras in real-time in both orthotopic lung models (shown) and in more conventional flank injection models (not shown). Imaging was performed using standard protocols and a Xenogen CCD imager (Caliper Life Sciences, Hopkinton, Mass. 01748).

FIG. 10: EMT ligands induce changes to E-cadherin and vimentin. Cells were treated for 7 days and stained for markers as described. HGF and OSM exhibit changes consistent with partial EMT while TGFβ and all dual ligand treatments result in more complete EMT (staining: E-cadherin, green; Vimentin, red; DNA, blue).

FIGS. 15A-B: Imaging of H358 luciferase expressing cells in vivo. Bioluminescent H358 inducible cells were generated by transducing pooled populations with lentivirus containing the firefly luciferase gene. These cells were then implanted into nude mice either subcutaneously (A), or orthotopically into the lung (B), where they were readily imaged using the Xenogen IVIS® Spectrum system.

DETAILED DESCRIPTION OF THE INVENTION

Figure 9A:
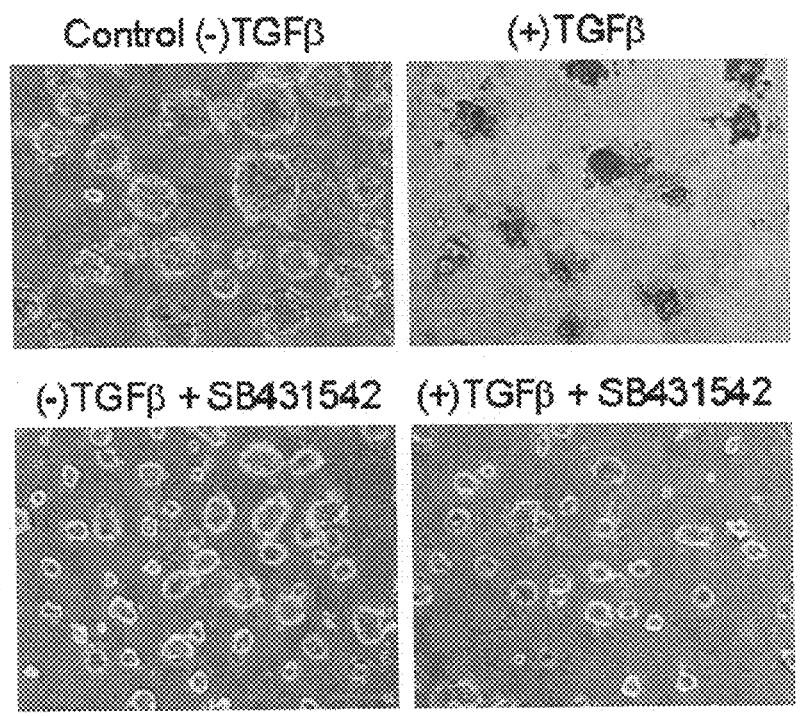
FIGS. 9A-B: Induction of EMT in H358 with TGFbeta in 3D Matrigel™ culture can be inhibited with a TGFbeta small molecule inhibitor (SB431542). [A] H358 NSCLC plated in MATRIGEL™ for 14-21 days in presence or absence of TGFbeta and SB431542. [B] Confocal microscopy of TGF-beta treated H358 in MATRIGEL™ demonstrating the restoration of epithelial phenotype in presence SB431542 (Staining: E-cadherin, green; Vimentin, red; DNA nuclear staining, blue).

The term "cancer" in an animal refers to the presence of cells possessing characteristics typical of cancer-causing cells, such as uncontrolled proliferation, immortality, metastatic potential, rapid growth and proliferation rate, and certain characteristic morphological features. Often, cancer cells will be in the form of a tumor, but such cells may exist alone within an animal, or may circulate in the blood stream as independent cells, such as leukemic cells.

"Cell growth", as used herein, for example in the context of "tumor cell growth", unless otherwise indicated, is used as commonly used in oncology, where the term is principally associated with growth in cell numbers, which occurs by means of cell reproduction (i.e. proliferation) when the rate the latter is greater than the rate of cell death (e.g. by apoptosis or necrosis), to produce an increase in the size of a population of cells, although a small component of that growth may in certain circumstances be due also to an increase in cell size or cytoplasmic volume of individual cells. An agent that inhibits cell growth can thus do so by either inhibiting proliferation or stimulating cell death, or both, such that the equilibrium between these two opposing processes is altered.

"Tumor growth" or "tumor metastases growth", as used herein, unless otherwise indicated, is used as commonly used in oncology, where the term is principally associated with an increased mass or volume of the tumor or tumor metastases, primarily as a result of tumor cell growth.

"Abnormal cell growth", as used herein, unless otherwise indicated, refers to cell growth that is independent of normal regulatory mechanisms (e.g., loss of contact inhibition). This includes the abnormal growth of: (1) tumor cells (tumors) that proliferate by expressing a mutated tyrosine kinase or overexpression of a receptor tyrosine kinase; (2) benign and malignant cells of other proliferative diseases in which aberrant tyrosine kinase activation occurs; (4) any tumors that proliferate by receptor tyrosine kinases; (5) any tumors that proliferate by aberrant serine/threonine kinase activation; and (6) benign and malignant cells of other proliferative diseases in which aberrant serine/threonine kinase activation occurs.

The term "treating" as used herein, unless otherwise indicated, means reversing, alleviating, inhibiting the progress of, or preventing, either partially or completely, the growth of tumors, tumor metastases, or other cancer-causing or neoplastic cells in a patient with cancer. The term "treatment" as used herein, unless otherwise indicated, refers to the act of treating.

The phrase "a method of treating" or its equivalent, when applied to, for example, cancer refers to a procedure or course of action that is designed to reduce or eliminate the number of cancer cells in an animal, or to alleviate the symptoms of a cancer. "A method of treating" cancer or another proliferative disorder does not necessarily mean that the cancer cells or other disorder will, in fact, be eliminated, that the number of cells or disorder will, in fact, be reduced, or that the symptoms of a cancer or other disorder will, in fact, be alleviated. Often, a method of treating cancer will be performed even with a low likelihood of success, but which, given the medical history and estimated survival expectancy of an animal, is nevertheless deemed an overall beneficial course of action.

The term "therapeutically effective agent" means a composition that will elicit the biological or medical response of a tissue, system, animal or human that is being sought by the researcher, veterinarian, medical doctor or other clinician.

The term "therapeutically effective amount" or "effective amount" means the amount of the subject compound or combination that will elicit the biological or medical response of a tissue, system, animal or human that is being sought by the researcher, veterinarian, medical doctor or other clinician.

The present invention derives from research that provided methods for determining which tumors will respond most effectively to treatment with protein-tyrosine kinase inhibitors (e.g. Thompson, S. et al. (2005) Cancer Res. 65(20): 9455-9462; U.S. Patent Application 60/997,514) based on whether the tumor cells have undergone an epithelial to mesenchymal transition ("EMT"; Thiery, J. P. (2002) Nat. Rev. Cancer 2:442-454; Savagner, P. (2001) Bioessays 23:912-923; Kang Y. and Massague, J. (2004) Cell 118:277-279; Julien-Grille, S., et al. Cancer Research 63:2172-2178; Bates, R. C. et al. (2003) Current Biology 13:1721-1727; Lu Z., et al. (2003) Cancer Cell. 4(6):499-515). This research demonstrated that epithelial cells respond well to EGFR and IGF-1R kinase inhibitors, but that after an EMT the resulting mesenchymal-like cells are much less sensitive to such inhibitors. Biomarkers can be used to determine whether tumor cells have undergone an EMT (Thomson, S. et al. (2005) Cancer Res. 65(20):9455-9462). As a result of such work it became apparent that new therapeutic approaches would be necessary to find agents that were capable of inhibiting the genesis, growth and/or function of such mesenchymal-like cells, which are thought to be an important element in the invasive and metastatic properties of tumors.

A considerable body of work is emerging that is beginning to delineate the biochemical pathways involved in regulating tumor EMT events, and to characterize the resultant mesenchymal-like tumor cells. For example, experiments using specific siRNA inhibitors of the expression of various protein products produced by mesenchymal-like tumor cells have demonstrated that reduced expression of the products of certain genes can specifically inhibit the growth of mesenchymal-like tumor cells. Thus pharmacological agents that also specifically inhibit the expression of the protein products encoded by these genes, or specifically inhibit the biological activity of the expressed proteins (e.g. phosphotransferase activity), such as specific antibodies to expressed proteins that possess an extracellular domain, antisense molecules, ribozymes, or small molecule enzyme inhibitors (e.g. protein kinase inhibitors), are similarly expected to be agents that will also specifically inhibit the growth of mesenchymal-like tumor cells. The anti-tumor effects of a combination of an EGFR or IGF-1R kinase inhibitor with such an agent should be superior to the anti-tumor effects of these kinase inhibitors by themselves, since such a combination should effectively inhibit both epithelial and mesenchymal-like tumor cells, and thus co-administration of such agents with EGFR or IGF-1R kinase inhibitors should be effective for treatment of patients with advanced cancers such as NSCL, pancreatic, colon or breast cancers.

Given the identification of key targets for the discovery and development of agents that will inhibit the growth of mesenchymal-like tumor cells, or the EMT process, there is thus a pressing need for models and methods to evaluate agents identified by in vitro screening methods (e.g. using protein kinase assays) to determine if they have the predicted effect of inhibiting the growth and/or migration of mesenchymal-like tumor cells, both at a cellular level, and in vivo. The data presented in the Examples herein demonstrates that the epithelial tumor cell line H358 can be stimulated to undergo EMT by contacting it with one or more cell receptor ligands, or by inducing the expression of one or more protein products capable of modulating the EMT process. Not all epithelial tumor cell lines can be stimulated to undergo EMT, and the optimal process for EMT induction is cell line dependent. Thus, H358 tumor cells, treated in various ways to induce EMT, can be used as models, both in vitro and vivo, in methods to identify agents that can inhibit mesenchymal-like tumor cells, prevent their formation, or reverse the EMT process. These methods are also useful in the identification of agents for the treatment of fibrotic disorders resulting in part from EMT transitions, including but not limited to renal fibrosis, hepatic fibrosis, pulmonary fibrosis, and mesotheliomas. Thus any of the inventions described herein as being applicable to tumor cells, will also be applicable to other cell types involved in fibrotic diseases that undergo EMT. Similarly, any of the inventions described herein as being useful for the identification of anti-cancer agents, will also be useful in the identification of anti-fibrotic agents for treating diseases that involve fibrosis.

"H358 cells" as used herein, refers to cells of the cell line NCI-H358™ [a.k.a. H-358; H358] available from the American Tissue Culture Collection (ATCC) as CRL-5807, derived form human lung bronchiole or alveolus and showing morphology of both bronchioalveolar carcinoma and non-small cell lung adenocarcinoma.

Accordingly, the present invention provides a method of identifying an agent that inhibits tumor cells from undergoing an epithelial to mesenchymal transition, comprising contacting a sample of cells of the epithelial tumor cell line H358 with a test agent to be screened, contacting the sample with a single or dual protein ligand preparation that induces an epithelial-to-mesenchymal transition in H358 cells, determining whether the test agent inhibits the tumor cells in the sample from undergoing an epithelial to mesenchymal transition, by comparing the level of a biomarker whose level is indicative of the EMT status of the sample tumor cells to the level of the same biomarker in an identical sample of H358 cells not contacted with the test agent, and thus determining whether the test agent is an agent that inhibits tumor cells from undergoing an epithelial to mesenchymal transition. In one embodiment, the single protein ligand that induces an epithelial-to-mesenchymal transition in H358 cells is selected from EGF; TGFbeta; TNFalpha; and IL-4. In another embodiment, the dual protein ligands that induce an epithelial-to-mesenchymal transition in H358 cells are oncostatin-M plus HGF.

A "single protein ligand preparation" as used herein, means a preparation comprising a protein ligand for a cell receptor, which ligand is capable, by itself, of substantially inducing EMT in H358 cells, as assessed for example by a significant decrease in expression of the epithelial biomarker E-cadherin, and/or a significant increase in expression of the mesenchymal biomarker vimentin. A "dual protein ligand preparation" as used herein, means a preparation comprising two protein ligands for different cell receptors, which ligands are capable of inducing EMT in H358 cells, and where both ligands are required for EMT induction (i.e. either ligand by itself does not substantially induce EMT). Either preparation may contain additional compounds or proteins, e.g. cell nutrients, other growth factors, agents that stabilize the protein ligands, etc. For example, a single protein ligand preparation may be supplemented with one or more alternative single ligands that also induces EMT, or a ligand that does not normally induce EMT on its own, which may result in a slightly more complete EMT. For example, HGF or OSM may be added to the EMT inducer TGF-beta, which results in a slightly more complete EMT, as judged by E-cadherin expression. "TGF-beta", as used herein can be any active mammalian TGF-beta protein, e.g. human TGFbeta-1 (TGFB1; NCIB GeneID: 7040), human TGFbeta-2 (TGFB2; NCIB GeneID: 7042), or human TGFbeta-3 (TGFB3; NCIB GeneID: 7043), or hererodimers thereof (see Massagué J, et al. (1992) Cancer Surv. 12:81-103).

In any of the methods or cell preparations of the invention described herein, the single protein ligand that induces an epithelial-to-mesenchymal transition in H358 cells may be selected from any of the protein ligands that bind to and activate the EGF receptor (i.e. NCIB GeneID: 1956, or heterodimers with other HER family receptors); TGF-beta receptor II (NCIB GeneID: 7048); TNFα receptor (TNFRSF1A, a.k.a. CD120a or TNF-R1; NCIB GeneID: 7132); or the IL-4 receptor (interleukin 4 receptor (IL4R); NCIB GeneID: 3566), either presently known, or yet to be discovered or synthesized. For example, the single protein ligand that induces an epithelial-to-mesenchymal transition in H358 cells may be selected from EGF (NCIB GeneID: 1950); TGF-beta; TNFα (tumor necrosis factor α; NCIB GeneID: 7124); and IL-4 (interleukin 4; NCIB GeneID: 3565). Other examples include the EGF receptor ligands, transforming growth factor-α (TGF-α; NCIB GeneID: 7039), heparin-binding EGF-like growth factor (HB-EGF; NCIB GeneID: 1839), amphiregulin (AREG; NCIB GeneID: 374), betacellulin (BTC; NCIB GeneID: 685), epiregulin (EREG; NCIB GeneID: 2069), and epigen (EPGN; NCIB GeneID: 255324); the TNF receptor ligand, TNF-beta; TGF-beta receptor II ligands, TGFbeta-1, TGFbeta-2, and TGF-beta-3, or hererodimers thereof; and the IL-4 receptor ligand, Interleukin-13 (IL-13; NCIB GeneID: 3596). The human versions of the above ligand proteins are preferred, but where an alternative animal version exists (e.g. from mouse, rat, rabbit, dog, monkey, pig, etc) that also has activity in stimulating the human receptor on H358 cells, and induces EMT, this may also be used.

In any of the methods or cell preparations of the invention described herein, the dual protein ligands that induce an epithelial-to-mesenchymal transition in H358 cells may comprise one ligand that binds to and activates the oncostatin-M receptor (OSMR; NCIB GeneID: 9180) plus one ligand that binds to and activates the HGF receptor (NCIB GeneID: 4233; a.k.a. met proto-oncogene, Met receptor tyrosine kinase, or hepatocyte growth factor receptor). For example, the dual protein ligands that induce an epithelial-to-mesenchymal transition in H358 cells may be oncostatin-M (OSM; NCIB GeneID: 5008) plus HGF (NCIB GeneID: 3082). In an alternative embodiment, the dual protein ligands that induce an epithelial-to-mesenchymal transition in H358 cells may comprise one protein ligand that binds to a receptor that activates the signal transduction pathways activated by the binding of oncostatin M to its receptor (e.g. one ligand that binds to and activates the oncostatin-M receptor (e.g. oncostatin M), or a protein ligand that binds to another receptor that activates the same signal transduction pathways as are activated by binding of oncostatin M to its receptor (i.e. JAK-STAT pathways)); plus one ligand that binds to a cell tyrosine kinase receptor and activates the same signal transduction pathways that are activated by the binding of HGF to its receptor (i.e. the PI3K and MAPK pathways; as activated by binding of HGF to Met receptor tyrosine kinase). Receptor tyrosine kinases that activate the PI3K and MAPK pathways include for example, IGF1-R, FGFR1, FGFR2, FGFR3, FGFR4, heterodimers of FGF receptors 1-4, RON, EGFR, HER-4, heterodimers of HER receptors 1-4, VEGFR-1 (Flt-1), VEGFR-2 (Flk-1/KDR), VEGFR-3 (Flt-4), and PDGFR ($\alpha$ and $\beta$ receptor homo- and herero-dimers). Thus, examples of additional ligands that may be combined with oncostatin M in a dual ligand preparation include IGF-1, IGF-2, FGF1, FGF2, FGF3, FGF4, FGF5, FGF6, FGF7, FGF8, FGF8, FGF10, macrophage-stimulating protein (MSP; RON receptor ligand), transforming growth factor-$\alpha$ (TGF-$\alpha$), heparin-binding EGF-like growth factor (HB-EGF), amphiregulin (AR), betacellulin (BTC), epiregulin (EPR), epigen (EPI), neuregulins (NRG-1 (Heregulin), NRG-2, NRG-3, NRG-4), VEGF-A, VEGF-B, VEGF-C, VEGF-D, VEGF-E, PDGF-AA, PDGF-AB, PDGF-BB, PDGF-CC, and PDGF-DD. The human versions of the above ligand proteins are preferred, but where an alternative animal version exists (e.g. from mouse, rat, rabbit, dog, monkey, pig, etc) that also has activity in stimulating the human receptor on H358 cells, and induces EMT, this may also be used.

The induction of EMT in H358 cells by the specific ligands disclosed herein allows targeting of specific pathways that induce EMT, and thus for identification of anticancer agents that may have different modes of action, and may thus act together in a synergistic manner. The dual-ligand driven EMT models and methods dependent thereon that are disclosed herein are absolutely dependent on both ligands for EMT induction. EMT induction by such dual-ligand preparations has not been previously described, and their use for identification of new anticancer agents may also lead to the identification of agents that have different modes of action from those identified by single ligand EMT induction systems, or by other dual ligand systems.

The NCBI GeneID numbers listed herein are unique identifiers of the human gene from the NCBI Entrez Gene database record (National Center for Biotechnology Information (NCBI), U.S. National Library of Medicine, 8600 Rockville Pike, Building 38A, Bethesda, Md. 20894; Internet address http://www.ncbi.nlm.nih.gov/). They are used herein to unambiguously identify gene products that are referred to elsewhere in the application by names and/or acronyms. Proteins expressed by genes thus identified represent proteins that may be used in the methods of this invention, and the sequences of these proteins, including different isoforms, as disclosed in NCBI database (e.g. GENBANK®) records are herein incorporated by reference.

The sample of cells of the epithelial tumor cell line H358 in any of the methods or preparations of this invention can be for example cells in monolayer culture (e.g. cells in a tissue culture plate or dish, e.g. a 96-well plate); cells in three-dimensional culture, such as for example Matrigel™ 3D culture, spheroid cultures, or soft agar culture (Kim, J. B., (2005) Seminars in Cancer Biology 15:365-377; Sutherland, R. M., (1988) Science 240:177-184; Hamilton, G. (1998) Cancer Letters, 131:29-34; or cells in vivo, e.g. a tumor xenograft. In methods described herein that require "an identical sample of cells", this refers to a sample of cells with essentially the same number of cells, growing under the same conditions. For example, an identical tissue culture dish with approximately the same number of cells, or a tumor xenograft of the same or similar size.

Many biomarkers are known whose level of expression or activity is indicative of the EMT status of tumor cells (e.g. see US Patent Application Publication. 2007/0212738; U.S. Patent Application 60/923,463; U.S. Patent Application 60/997,514). Such markers tend to be classified as epithelial or mesenchymal, due to their characteristic association with the particular stage of EMT. Characteristic biomarkers can be, for example, proteins, encoding mRNAs, activity of a gene promoter, level of a transcriptional repressor, or promoter methylation. In any of the methods described herein the biomarker whose expression level is indicative of the EMT status of the sample tumor cells can be an epithelial cell biomarker. Epithelial cell biomarkers include for example E-cadherin, cytokeratin 8, cytokeratin 18, P-cadherin or erbB3. Additional epithelial cell biomarkers include Brk, $\gamma$-catenin, $\alpha$1-catenin, $\alpha$2-catenin, $\alpha$3-catenin, connexin 31, plakophilin 3, stratifin 1, laminin alpha-5 and ST14. In any of the methods described herein the biomarker whose expression level is indicative of the EMT status of the sample tumor cells can also be a mesenchymal cell biomarker. Mesenchymal cell biomarkers include for example is vimentin, fibronectin, N-cadherin, zeb1, twist, FOXC2 or snail. Additional mesenchymal cell biomarkers include, fibrillin-1, fibrillin-2, collagen alpha2(IV), collagen alpha2(V), LOXL1, nidogen, C11 or f9, tenascin, tubulin alpha-3, and epimorphin. Additionally any other epithelial or mesenchymal cell biomarkers known in the art, described herein, or yet to be described, may be used in the methods of the invention described herein. In any of the methods described herein, multiple biomarker level determinations can also be used to assess EMT status, potentially providing a more reliable assessment. For example, an epithelial and a mesenchymal biomarker level may be assessed, the reciprocal changes in each providing internal confirmation that EMT has occurred (e.g. suitable biomarker pairs include for example, E-cadherin/vimentin). In an alternative embodiment, the epithelial biomarker comprises one or more keratins selected from the epithelial keratins 1-28 and 71-80, and the mesenchymal biomarker is vimentin, wherein co-expression of epithelial and mesenchymal biomarkers at similar levels is indicative of a mesenchymal-like tumor cell (see U.S. Patent Application 60/923,463). When used in any of the methods of the invention described herein, epithelial keratins 1-28 and 71-80 includes all the keratins listed in Table 2 herein. In one embodiment of the latter method the epithelial keratin(s) are assessed using a method that will detect all or the majority (i.e. 50% or more) of the keratin biomarkers expressed by the tumor cell (e.g. by using a multi- or pan-specific antibody). In another embodiment of above methods where epithelial keratin biomarker levels are determined, the biomarker comprises keratin 8 and/or keratin 18.

The term "co-expression of epithelial and mesenchymal biomarkers at similar levels" as used herein in the context of determining co-expression of epithelial keratins and the mesenchymal biomarker vimentin means that the ratio of mesenchymal to epithelial biomarker levels is in the range of about 10:1 to about 1:10 (assuming that each biomarker is assayed under comparable conditions, e.g. using antibodies of identical affinity, nucleic acid probes of identical length, identical detection methods, etc.).

In an alternative embodiment of any of the methods described herein that include a step of determining the level of a biomarker whose level is indicative of the EMT status of the sample tumor cells, the biomarker can be the activity of a gene promoter that is altered when the tumor cells undergo EMT. Such promoter activity is readily assessed by incorporating a promoter-reporter construct into the tumor cells and measuring reporter activity. In one embodiment, the activity of an epithelial biomarker gene promoter is assessed by inclusion of an epithelial biomarker gene promoter-reporter gene construct into the H358 cells such that said promoter reporter activity can be monitored by reporter gene expression level or activity. For example, the epithelial biomarker gene promoter-reporter gene construct may be an E-cadherin promoter-firefly luciferase construct. In an alternative embodiment, the activity of a mesenchymal biomarker gene promoter is assessed by inclusion of a mesenchymal biomarker gene promoter-reporter gene construct into the H358 cells such that said promoter reporter activity can be monitored by reporter gene expression level or activity. For example, the mesenchymal biomarker gene promoter-reporter gene construct may be an vimentin promoter-firefly luciferase construct. The promoter-reporter gene construct may be permanently incorporated into the H358 cells as a stable engineered cell line, or may be transiently expressed, using any of the standard techniques for transferring nucleic acid constructs into cells (e.g. transfection, electroporation). Multiple promoter-reporter gene constructs may also be employed in order to monitor several biomarkers simultaneously, e.g. an E-cadherin promoter-firefly luciferase construct and a vimentin promoter-*renilla* luciferase construct, in order to, for example, monitor simultaneous repression of the E-cadherin gene and induction of the vimentin gene as tumor cells undergo EMT.

The present invention also provides a method of identifying an agent that inhibits tumor cells that have undergone an epithelial to mesenchymal transition, comprising contacting a sample of cells of the epithelial tumor cell line H358 with a single or dual protein ligand preparation to induce an epithelial-to-mesenchymal transition in the H358 cells, contacting the sample of cells with a test agent to be screened, determining whether the test agent inhibits mesenchymal-like H358 cell growth, and thus determining whether it is an agent that inhibits the growth of tumor cells that have undergone an epithelial to mesenchymal transition. In one embodiment, the single protein ligand that induces an epithelial-to-mesenchymal transition in H358 cells is selected from EGF; TGFbeta; TNFalpha; and IL-4. In another embodiment, the dual protein ligands that induce an epithelial-to-mesenchymal transition in H358 cells are oncostatin-M plus HGF. An alternative embodiment of this method comprises, after the step of determining whether the test agent inhibits the growth of tumor cells that have undergone an epithelial to mesenchymal transition, the additional steps of determining whether an agent that inhibits mesenchymal-like H358 tumor cell growth, also inhibits epithelial H358 tumor cell growth, and thus determining whether it is an agent that specifically inhibits the growth of tumor cells that have undergone an epithelial to mesenchymal transition. In an embodiment of the above methods, an agent that inhibits the growth of tumor cells that have undergone an epithelial to mesenchymal transition is determined to do so by stimulating apoptosis of said tumor cells. In another embodiment of the above methods, an agent that inhibits the growth of tumor cells that have undergone an epithelial to mesenchymal transition is determined to do so by inhibiting proliferation of said tumor cells.

The present invention also provides a method of identifying an agent that stimulates mesenchymal-like tumor cells to undergo a mesenchymal to epithelial transition, comprising contacting a sample of cells of the epithelial tumor cell line H358 with a single or dual protein ligand preparation to induce, an epithelial-to-mesenchymal transition in the H358 cells, contacting the sample of cells with a test agent to be screened, determining whether the test agent stimulates the mesenchymal-like H358 cells in the sample to undergo a mesenchymal to epithelial transition, by comparing the level of a biomarker whose level is indicative of the EMT status of the sample tumor cells to the level of the same biomarker in an identical sample of mesenchymal-like H358 cells not contacted with the test agent, and thus determining whether the test agent is an agent that stimulates mesenchymal-like tumor cells to undergo a mesenchymal to epithelial transition. In one embodiment, the single protein ligand that induces an epithelial-to-mesenchymal transition in H358 cells is selected from EGF; TGFbeta; TNFalpha; and IL-4. In another embodiment, the dual protein ligands that induce an epithelial-to-mesenchymal transition in H358 cells are oncostatin-M plus HGF.

The present invention also provides a method of preparing a composition comprising a chemical compound which inhibits the growth of tumor cells that have undergone an epithelial to mesenchymal transition, which comprises contacting a sample of cells of the epithelial tumor cell line H358 with a test agent to be screened, contacting the sample with a single or dual protein ligand preparation that induces an epithelial-to-mesenchymal transition in H358 cells, determining whether the test agent inhibits the tumor cells in the sample from undergoing an epithelial to mesenchymal transition, by comparing the level of a biomarker whose level is indicative of the EMT status of the sample tumor cells to the level of the same biomarker in an identical sample of H358 cells not contacted with the test agent, and thus determining whether the test agent is an agent that inhibits tumor cells from undergoing an epithelial to mesenchymal transition, and admixing the test agent so identified with a carrier, thereby preparing said composition.

The present invention also provides a method of preparing a composition comprising a chemical compound which inhibits the growth of tumor cells that have undergone an epithelial to mesenchymal transition, which comprises contacting a sample of cells of the epithelial tumor cell line H358 with a single or dual protein ligand preparation to induce an epithelial-to-mesenchymal transition in the H358 cells, contacting the sample of cells with a test agent to be screened, determining whether the test agent inhibits mesenchymal-like H358 cell growth, and thus determining whether it is an agent that inhibits the growth of tumor cells that have undergone an epithelial to mesenchymal transition, and admixing the test agent so identified with a carrier, thereby preparing said composition.

The present invention also provides a method of preparing a composition comprising a chemical compound which inhibits the growth of tumor cells that have undergone an epithelial to mesenchymal transition, which comprises contacting a sample of cells of the epithelial tumor cell line H358 with a single or dual protein ligand preparation to induce an epithelial-to-mesenchymal transition in the H358 cells, contacting the sample of cells with a test agent to be screened, determining whether the test agent stimulates the mesenchymal-like H358 cells in the sample to undergo a mesenchymal to epithelial transition, by comparing the level of a biomarker whose level is indicative of the EMT status of the sample tumor cells to the level of the same biomarker in an identical sample of mesenchymal-like H358 cells not contacted with the test agent, and thus determining whether the test agent is an agent that stimulates mesenchymal-like tumor cells to undergo a mesenchymal to epithelial transition, and admixing the test agent so identified with a carrier, thereby preparing said composition.

The present invention also provides a mesenchymal-like tumor cell preparation for use in the identification of anti-cancer agents, wherein said tumor cell preparation is prepared by a process comprising: contacting a sample of cells of the epithelial tumor cell line H358 with a single or dual protein ligand preparation to induce an epithelial-to-mesenchymal transition in the H358 cells, wherein the single protein ligand that induces an epithelial-to-mesenchymal transition in H358 cells is selected from EGF; TGFbeta; TNFalpha; and IL-4, and wherein the dual protein ligands that induce an epithelial-to-mesenchymal transition in H358 cells are oncostatin-M plus HGF.

For any of the methods described herein, a test agent can be any chemical compound, including small molecules (<approx. 5000 Daltons molecular weight) and macromolecules (e.g. a polypeptide or protein, nucleic acid, glycoprotein, complex carbohydrate, synthetic or natural polymer etc.). Thus, a test agent may be selected from, for example, combinatorial libraries, defined chemical entities, peptide and peptide mimetics, oligonucleotides and natural product libraries, aptamers, and other entities such as display (e.g. phage display libraries) and antibody products.

The present invention also provides a method of identifying an agent that inhibits tumor cells from undergoing an epithelial to mesenchymal transition, comprising contacting a sample of cells of the epithelial tumor cell line H358, which have been engineered to inducibly express a protein that stimulates an epithelial to mesenchymal transition in H358 cells, with a test agent to be screened, contacting the sample with a compound that induces the expression of said protein that stimulates an epithelial to mesenchymal transition in the engineered H358 cells, determining whether the test agent inhibits the tumor cells in the sample from undergoing an epithelial to mesenchymal transition, by comparing the level of a biomarker whose level is indicative of the EMT status of the sample tumor cells to the level of the same biomarker in an identical sample of engineered H358 cells not contacted with the test agent, and thus determining whether the test agent is an agent that inhibits tumor cells from undergoing an epithelial to mesenchymal transition.

"Inducibly express", as used herein, when referring for example to cells which have been engineered to "inducibly express" a protein, means that the protein expression is only turned on by the presence (or absence) of an inducing agent that controls transcription of the gene encoding the protein, which will preferably be incorporated into the cells by stable transformation with a construct containing the gene for the encoding protein under the control of a promoter that is responsive to the inducing agent (i.e. the gene encoding the protein is operably linked to a nucleotide sequence regulating the gene expression, which nucleotide sequence comprises a promoter sequence whose activity can be controlled by the presence of an inducing agent). One example of such an inducible promoter is a tetracycline (tet)-responsive promoter (e.g. a Tet-on system; e.g. see Gossen, M. et al. (1995) Science 268:1766-1769). Such inducible gene expression systems for controlling the expression levels of specific genes of interest are well known in the art (e.g. see Blau, H. M. and Rossi, F. M. V. (1999) Proc. Natl. Acad. Sci. USA 96:797-799; Yamamoto, A. et al. (2001) Neurobiology of Disease 8:923-932; Clackson, T. (2000) Gene Therapy 7:120-125).

For any of the methods or cell preparations described herein involving the epithelial tumor cell line H358 which has been engineered to inducibly express a protein that stimulates an epithelial to mesenchymal transition in H358 cells, in one embodiment the cells also comprise a promoter-reporter gene construct that can be similarly inducibly expressed, such that said promoter reporter activity can be monitored by reporter gene expression level or activity, and thus be used to readily assess whether induction of the protein that stimulates an epithelial to mesenchymal transition has been successful. In one example of such an embodiment, the reporter gene is the gene for firefly or *Renilla* luciferase. Assessment of reporter levels can for example be used for readily monitoring the extent of EMT induction of H358 cells, and the location of cells that have undergone EMT. Thus, for example, cells in vivo that have migrated from a primary tumor, or metastasized, can be readily tracked by monitoring such a reporter gene. Thus, the present invention provides a method of identifying an agent that inhibits tumor cells from undergoing an epithelial to mesenchymal transition (and metastasis), comprising contacting in vivo a sample of cells of the epithelial tumor cell line H358, which have been engineered to inducibly express both a protein that stimulates an epithelial to mesenchymal transition in H358 cells, and a reporter gene product (e.g. firefly luciferase), and which have been allowed to form a tumor xenograft in an immunocompromised animal, with a test agent to be screened, contacting the sample with a compound that induces the expression of said protein that stimulates an epithelial to mesenchymal transition in the engineered H358 cells and the reporter gene product, determining whether the test agent inhibits the tumor cells in the sample from undergoing an epithelial to mesenchymal transition (and metastasis), by comparing the extent of migration of the sample tumor cells away from a primary tumor (e.g. by imaging analysis of the reporter gene product) to the extent of migration of an identical sample of engineered H358 cells not contacted with the test agent, and thus determining whether the test agent is an agent that inhibits tumor cells from undergoing an epithelial to mesenchymal transition (and metastasis). Cells derived form an EMT-transition in vivo can also be detected by surgical isolation and immunohistochemistry or in situ hybridization using for example biomarkers as described herein, or in US Patent Application Publication 2007/0212738, U.S. Patent Application 60/923,463, or U.S. Patent Application 60/997,514).

In one embodiment of the above methods the protein that is inducibly expressed and stimulates an epithelial to mesenchymal transition in H358 cells is Snail. In another embodiment of this method the protein that is inducibly expressed and stimulates an epithelial to mesenchymal transition in H358 cells is Zeb-1. In another embodiment of this method the protein that is inducibly expressed and stimulates an epithelial to mesenchymal transition in H358 cells is constitutively active TGF-beta. In an alternative embodiment, the protein that is inducibly expressed and stimulates an epithelial to mesenchymal transition in H358 cells may be co-expressed with one or more other proteins that enhance the EMT. Additional EMT causing genes that encode proteins that may be inducibly expressed in engineered H358 cells to promote EMT include, but are not limited to, co-expressed HGF and OSM; tumor necrosis factor alpha (TNFa); constitutively active cMET receptor; activated Src kinase (e.g. v-Src or Src Y530F mutants); IL-4; IL-13; EGF, transforming growth factor-α (TGF-α), heparin-binding EGF-like growth factor (HB-EGF), amphiregulin (AR), betacellulin (BTC), epiregulin (EPR), epigen (EPI); and TNF-beta. Similarly, in any of the other methods or cell preparations described herein involving a protein that is inducibly expressed and stimulates an epithelial to mesenchymal transition in H358 cells, the protein can be any of the examples described above.

In one embodiment of these methods, a Tet-regulated promoter is used to inducibly express the protein that stimulates an epithelial to mesenchymal transition in H358 cells, e.g. a Tet-on system. In one embodiment of this method, the compound that induces the expression of the protein that stimulates an epithelial to mesenchymal transition in the engineered H358 cells is doxycycline. Other inducers that may be used include, but are not limited to, tetracycline and anhydrotetracycline. Similarly, in any of the other methods or cell preparations described herein involving a protein that is inducibly expressed and stimulates an epithelial to mesenchymal transition in H358 cells, the promoter and inducer compound used to inducibly express the protein can be any of the examples described above. Induction systems include but are not limited to tetracycline regulated plasmids, e.g. Tet-on and Tet-off systems?

In the above methods the biomarker whose level is indicative of the EMT status of the sample tumor cells is for example an epithelial cell biomarker, e.g. E-cadherin, cytoketatin 8, cytokeratin 18, P-cadherin or erbB3, or the activity of an epithelial biomarker gene promoter. In one embodiment, the activity of an epithelial biomarker gene promoter may be assessed by inclusion of a human epithelial biomarker gene promoter-reporter gene construct in the engineered H358 cells such that said promoter reporter activity can be monitored by reporter gene expression level or activity. In one embodiment, the epithelial biomarker gene promoter-reporter gene construct is a human E-cadherin promoter-firefly luciferase construct. Additional examples of epithelial promoters that may be used include the promoters of the following genes: human ELF3 (i.e. E74-like factor 3 (ets domain transcription factor, epithelial-specific), GeneID: 1999). In an alternative embodiment, RNA transcript splicing mechanisms that are unique to human epithelial cells (Savagner, P. et al. (1994) Mol Biol Cell. 5(8):851-862; Oltean, S. et al. (2006) Proc Natl Acad Sci USA. 103(38):14116-14121; Ghigna, C. et al. (2005) Mol Cell. 20(6):881-890; Bonano, V. I. et al. (2007) Nat Protoc. 2(9):2166-2181), and do not operate after EMT, can be utilized as markers of EMT status. For example, by including the sequences necessary for such epithelial-specific splicing into a promoter-luciferase construct incorporated into H358 cells (e.g. a CMV promoter-firefly luciferase construct) such that active luciferase will only be expressed in the epithelial state, induction of EMT can readily be monitored by a decrease in luciferase expression or activity. In an alternative embodiment, miRNAs that are expressed specifically in human epithelial cells (e.g. see Hurteau, G. J. et al. (2007) Cancer Research 67:7972-7976; Christoffersen, N. R. et al. (2007) RNA 13:1172-1178; Shell, S. et al (2007) Proc Natl. Acad. Sci. 104(27):11400-11405), that degrade or diminish translation of transcripts containing complementary nucleic acid sequences, can be utilized as markers of EMT status. For example, by including sequences complementary to such miRNAs into a promoter-luciferase construct incorporated into H358 cells (e.g. a CMV promoter-firefly luciferase construct) such that active luciferase will not be expressed in the epithelial state, induction of EMT can readily be monitored by an increase in luciferase expression or activity. Similarly, in any of the other methods described herein involving a protein that is inducibly expressed and stimulates an epithelial to mesenchymal transition in H358 cells, the biomarker whose level is indicative of the EMT status of the sample tumor cells can be any of the examples described above.

In the above methods the biomarker whose level is indicative of the EMT status of the sample tumor cells is for example a mesenchymal cell biomarker, e.g. vimentin, fibronectin, N-cadherin, zeb1, twist, FOXC2 or snail, or the activity of a mesenchymal biomarker gene promoter. In one embodiment, the activity of a mesenchymal biomarker gene promoter may be assessed by inclusion of a human mesenchymal biomarker gene promoter-reporter gene construct in the engineered H358 cells such that said promoter reporter activity can be monitored by reporter gene expression level or activity. In one embodiment, the mesenchymal biomarker gene promoter-reporter gene construct is a human vimentin promoter-firefly luciferase construct. Additional examples of mesenchymal promoters that may be used include the promoters from the following human genes: S100A4 (i.e. S100 calcium binding protein A4 (a.k.a. FSP1), GeneID: 6275), SPARC (i.e. secreted protein, acidic, cysteine-rich (osteonectin), GeneID: 6678), IL-11 (i.e. interleukin 11, GeneID: 3589), PCOLCE2 (i.e procollagen C-endopeptidase enhancer 2, GeneID: 26577), COL6A2 (i.e. collagen, type VI, alpha 2, GeneID: 1292), TFPI2 (i.e. tissue factor pathway inhibitor 2), GeneID: 7980), FBN1 (i.e. fibrillin 1, GeneID: 2200), Zeb1 (i.e. zinc finger E-box binding homeobox 1, GeneID: 6935), and CHST2 (i.e. carbohydrate (N-acetylglucosamine-6-O) sulfotransferase 2, GeneID: 9435). In an alternative embodiment, RNA transcript splicing mechanisms that are unique to human mesenchymal cells (Savagner, P. et al. (1994) Mol Biol Cell. 5(8):851-862; Oltean, S. et al. (2006) Proc Natl Acad Sci USA. 103(38):14116-14121; Ghigna, C. et al. (2005) Mol Cell. 20(6):881-890; Bonano, V. I. et al. (2007) Nat Protoc. 2(9):2166-2181), and do not operate prior to EMT, in epithelial cells, can be utilized as markers of EMT status. For example, by including the sequences necessary for such mesenchymal-specific splicing into a promoter-luciferase construct incorporated into H358 cells (e.g. a CMV promoter-firefly luciferase construct) such that active luciferase will only be expressed in the mesenchymal state, induction of EMT can readily be monitored by an increase in luciferase expression or activity. In an alternative embodiment, miRNAs that are expressed specifically in human mesenchymal cells (e.g. see Hurteau, G. J. et al. (2007) Cancer Research 67:7972-7976; Christoffersen, N. R. et al. (2007) RNA 13:1172-1178; Shell, S. et al (2007) Proc Natl. Acad. Sci. 104(27):11400-11405), that degrade or diminish translation of transcripts containing complementary nucleic acid sequences, can be utilized as markers of EMT status. For example, by including sequences complementary to such miRNAs into a promoter-luciferase construct incorporated into H358 cells (e.g. a CMV promoter-firefly luciferase construct) such that active luciferase will not be expressed in the mesenchymal state, induction of EMT can readily be monitored by a decrease in luciferase expression or activity. Similarly, in any of the other methods described herein involving a protein that is inducibly expressed and stimulates an epithelial to mesenchymal transition in H358 cells, the biomarker whose level is indicative of the EMT status of the sample tumor cells can be any of the examples described above.

In any of the methods or cell preparations described herein involving a biomarker gene promoter-reporter gene construct in the engineered H358 cells for monitoring biomarker promoter activity, more than one biomarker gene promoter-reporter gene construct may be employed so that multiple biomarkers may be simultaneously monitored in order to assess EMT status. For example, in one embodiment an epithelial biomarker gene promoter-reporter gene construct and a mesenchymal biomarker gene promoter-reporter gene construct are both used such that decreases in epithelial biomarker gene promoter activity and increases in mesenchymal biomarker gene promoter activity can both be monitored during EMT. For example, the epithelial biomarker gene promoter-reporter gene construct may be an E-cadherin promoter-firefly luciferase construct and the mesenchymal biomarker gene promoter-reporter gene construct may be a vimentin promoter-renilla luciferase construct. By using two different reporter genes that can be independently monitored (e.g. two luciferases that produce products that take part in luminescent reactions involving the emission of light of different characteristic wavelengths; e.g. see Hawkins, E. H. et al. (2002) DUAL-GLO® Luciferase Assay System: Convenient dual-reporter measurements in 96- and 384-well plates. *Promega Notes* 81, 22-6; Nieuwenhuijsen B W. et al. (2004) J Biomol Screen. 8, 676-84), both promoters can be monitored simultaneously. Similarly, two or more of the biomarkers described herein above involving epithelial or mesenchymal specific miRNAs or splicing mechanisms can be simultaneously monitored by using two different reporter genes that can be independently monitored.

In any of the methods or cell preparations described herein involving a biomarker gene promoter-reporter gene construct in the engineered H358 cells for monitoring biomarker promoter activity by assessing reporter gene expression level, the reporter gene can be any heterologous gene that expresses a protein whose level is readily determined by measuring expressed protein or enzymic activity. Suitable reporter genes include firefly (*Photinus pyralis*) luciferase, *Renilla* (*Renilla reniformis*) luciferase, *Gaussia* (*Gaussia princeps*) luciferase, green fluorescent protein (GFP), red fluorescent protein (RFP), etc. (e.g. see Hawkins, E. H. et al. (2002) DUAL-GLO® Luciferase Assay System: Convenient dual-reporter measurements in 96- and 384-well plates. *Promega Notes* 81, 22-6; Nieuwenhuijsen B W. et al. (2004) J. Biomol. Screen. 8, 676-84; Verhaegen M. and Christopoulos T. K. (2002) Anal. Chem., 74:4378-4385; Tannous, B. A., et al. (2005) Mol. Ther., 11:435-443; Hoffmann, R. M. (2004) Acta Histochemica 106(2):77-87); Hoffmann, R. M. (2008) Methods in Cell Biol. 85:485-495). Gaussia luciferase is a protein that is secreted from cells where it is expressed, hence it potentially allows, in any of the methods of the invention, the monitoring of reporter activity secreted into in the growth medium of cells in culture, or into the blood, or other biological fluids, from cells growing in vivo (e.g. tumor xenografts).

In one embodiment of the above methods, the sample of cells of the epithelial tumor cell line H358, which have been engineered to inducibly express a protein that stimulates an epithelial to mesenchymal transition in H358 cells, is an in vivo sample, such as, for example, a xenograft growing in an animal (e.g. immunocompromised mice or rats). Similarly, in any of the other methods or cell preparations described herein involving a protein that is inducibly expressed and stimulates an epithelial to mesenchymal transition in H358 cells, the sample of cells of the epithelial tumor cell line H358 can be an in vivo sample, as described above.

The present invention also provides an animal model comprising a sample of cells of the epithelial tumor cell line H358, which have been engineered to inducibly express a protein that stimulates an epithelial to mesenchymal transition in H358 cells, wherein the sample of cells is a xenograft. In one embodiment of this animal model the animal is an immune-deficient animal (e.g. an immune-deficient mouse, such as a nude mouse, also known as a Foxn1nu mouse; or a NOG (NOD/Shi-scid/IL-2Rγ$^{null}$) mouse; a SCID mouse; or a NOD/scid mouse).

The present invention also provides a method of identifying an agent that inhibits tumor cells that have undergone an epithelial to mesenchymal transition, comprising: contacting a sample of cells of the epithelial tumor cell line H358, which have been engineered to inducibly express a protein that stimulates an epithelial to mesenchymal transition in H358 cells, with a compound that induces the expression of said protein such that an epithelial-to-mesenchymal transition is induced in the cells, contacting the sample of cells with a test agent to be screened, determining whether the test agent inhibits mesenchymal-like H358 cell growth, and thus determining whether it is an agent that inhibits the growth of tumor cells that have undergone an epithelial to mesenchymal transition. An alternative embodiment of this method comprises, after the step of determining whether the test agent inhibits the growth of tumor cells that have undergone an epithelial to mesenchymal transition, the additional steps of determining whether an agent that inhibits mesenchymal-like H358 tumor cell growth, also inhibits epithelial H358 tumor cell growth, and thus determining whether it is an agent that specifically inhibits the growth of tumor cells that have undergone an epithelial to mesenchymal transition. In an embodiment of the above methods, an agent that inhibits the growth of tumor cells that have undergone an epithelial to mesenchymal transition is determined to do so by stimulating apoptosis of said tumor cells. In another embodiment of the above methods, an agent that inhibits the growth of tumor cells that have undergone an epithelial to mesenchymal transition is determined to do so by inhibiting proliferation of said tumor cells.

The present invention also provides a method of identifying an agent that stimulates mesenchymal-like tumor cells to undergo a mesenchymal to epithelial transition, comprising contacting a sample of cells of the epithelial tumor cell line H358, which have been engineered to inducibly express a protein that stimulates an epithelial to mesenchymal transition in H358 cells, with a compound that induces the expression of said protein such that an epithelial-to-mesenchymal transition is induced in the cells, contacting the sample of cells with a test agent to be screened, determining whether the test agent stimulates the mesenchymal-like H358 cells in the sample to undergo a mesenchymal to epithelial transition, by comparing the level of a biomarker whose level is indicative of the EMT status of the sample tumor cells to the level of the same biomarker in an identical sample of mesenchymal-like H358 cells not contacted with the test agent, and thus determining whether the test agent is an agent that stimulates-mesenchymal-like tumor cells to undergo a mesenchymal to epithelial transition.

The present invention also provides a tumor cell preparation for use in the identification of anti-cancer agents, wherein said tumor cell preparation comprises: a sample of cells of the epithelial tumor cell line H358, which have been engineered to inducibly express a protein that stimulates an epithelial to mesenchymal transition in H358 cells. In one embodiment, the tumor cell preparation also comprises a mesenchymal biomarker gene promoter-reporter gene construct in the engineered H358 cells so that the activity of the mesenchymal biomarker gene promoter can be assessed by monitoring reporter gene level or activity. In one embodiment, the mesenchymal biomarker gene promoter-reporter gene construct is a vimentin promoter-firefly luciferase construct. In another embodiment, the tumor cell preparation comprises a epithelial biomarker gene promoter-reporter gene construct in the engineered H358 cells so that the activity of the epithelial biomarker gene promoter can be assessed by monitoring reporter gene level or activity. In one embodiment, the epithelial biomarker gene promoter-reporter gene construct is an E-cadherin promoter-firefly luciferase construct. In the above cell preparations the protein that is inducibly expressed and stimulates an epithelial to mesenchymal transition in H358 cells can be any of those identified for use in the methods described herein above that utilize such a cell preparation (e.g. Snail, Zeb1 etc). In one embodiment of this cell preparation, a Tet-regulated promoter is used to inducibly express (e.g. using doxycyclin, or tetracycline) the protein that stimulates an epithelial to mesenchymal transition in the H358 cells. In the above embodiments, the biomarker gene promoter-reporter gene construct is stably expressed by the engineered H358 cell. Accordingly, this invention provides, for use in the identification of anti-cancer agents, both an epithelial H358 tumor cell preparation, prior to induction of a protein that stimulates an epithelial to mesenchymal transition, and a mesenchymal-like tumor cell preparation, after induction of a protein that stimulates an epithelial to mesenchymal transition. As described herein, these cell preparations can be used for screening test agents to identify agents that inhibit either cell type, or to find agents that will inhibit EMT or stimulate MET.

In the context of the methods of this invention, epithelial or mesenchymal biomarkers expressed by a tumor cell can include molecular and cellular markers that indicate the transition state of the tumor cell. In a preferred embodiment the biomarker is an individual marker protein, or its encoding mRNA, characteristic of the particular transition state of the tumor cell, i.e. a tumor cell exhibiting epithelial or mesenchymal characteristics. In an alternative embodiment, in certain circumstances the biomarker may be a characteristic morphological pattern produced in the tumor cell by cellular macromolecules that is characteristic of either an epithelial or mesenchymal condition. Thus, morphometric cell analysis can be used to provide information on epithelial or mesenchymal status of tumor cells. In an additional embodiment the biomarker that indicates the transition state of the tumor cell is methylation of the E-Cadherin gene (CDH1) promoter. CDH1 promoter methylation indicates that tumor cells have undergone an EMT transition.

TABLE 1

Molecular Biomarker Gene Identification

| Human Biomarker | NCBI GeneID[1] | NCBI RefSeq[2] |
|---|---|---|
| E-cadherin | 999 | NP_004351 |
| Brk | 5753 | NP_005966 |
| γ-catenin | 3728 | NP_002221 |
| α1-catenin | 1495 | NP_001894 |
| α2-catenin | 1496 | NP_004380 |
| α3-catenin | 29119 | NP_037398 |
| keratin 8 | 3856 | NP_002264 |
| keratin 18 | 3875 | NP_000215 |
| vimentin | 7431 | NP_003371 |
| fibronectin 1 | 2335 | NP_002017 |
| fibrillin-1 | 2200 | NP_000129 |
| fibrillin-2 | 2201 | NP_001990 |
| collagen alpha2(IV) | 1284 | NP_001837 |
| collagen alpha2(V) | 1290 | NP_000384 |
| LOXL1 | 4016 | NP_005567 |
| nidogen | 4811 | NP_002499 |
| C11orf9 | 745 | NP_037411 |

TABLE 1-continued

Molecular Biomarker Gene Identification

| Human Biomarker | NCBI GeneID[1] | NCBI RefSeq[2] |
|---|---|---|
| tenascin | 3371 | NP_002151 |
| N-cadherin | 1000 | NP_001783 |

[1]The NCBI GeneID number is a unique identifier of the biomarker gene from the NCBI Entrez Gene database record (National Center for Biotechnology Information (NCBI), U.S. National Library of Medicine, 8600 Rockville Pike, Building 38A, Bethesda, MD 20894; Internet address http://www.ncbi.nlm.nih.gov/).
[2]The NCBI RefSeq (Reference Sequence) is an example of a sequence expressed by the biomarker gene.

TABLE 2

Molecular Biomarker Gene Identification

| Human Biomarker[3] | NCBI GeneID[1] | NCBI RefSeq[2] |
|---|---|---|
| Epithelial | | |
| keratin K1 | 3848 | NP_006112 |
| keratin K2 | 3849 | NP_000414 |
| keratin K3 | 3850 | NP_476429 |
| keratin K4 | 3851 | NP_002263 |
| keratin K5 | 3852 | NP_000415 |
| keratin K6a | 3853 | NP_005545 |
| keratin K6b | 3854 | NP_005546 |
| keratin K6c | 286887 | NP_775109 |
| keratin K7 | 3855 | NP_005547 |
| keratin K8 | 3856 | NP_002264 |
| keratin K9 | 3857 | NP_000217 |
| keratin K10 | 3858 | NP_000412 |
| keratin K12 | 3859 | NP_000214 |
| keratin K13 | 3860 | NP_002265 |
| keratin K14 | 3861 | NP_000517 |
| keratin K15 | 3866 | NP_002266 |
| keratin K16 | 3868 | NP_005548 |
| keratin K17 | 3872 | NP_000413 |
| keratin K18 | 3875 | NP_000215 |
| keratin K19 | 3880 | NP_002267 |
| keratin K20 | 54474 | NP_061883 |
| keratin K23 | 25984 | NP_056330 |
| keratin K24 | 192666 | NP_061889 |
| keratin K25 | 147183 | NP_853512 |
| keratin K26 | 353288 | NP_853517 |
| keratin K27 | 342574 | NP_853515 |
| keratin K28 | 162605 | NP_853513 |
| keratin K71 | 112802 | NP_258259 |
| keratin K72 | 140807 | NP_542785 |
| keratin K73 | 319101 | NP_778238 |
| keratin K74 | 121391 | NP_778223 |
| keratin K75 | 9119 | NP_004684 |
| keratin K76 | 51350 | NP_056932 |
| keratin K77 | 374454 | NP_778253 |
| keratin K78 | 196374 | NP_775487 |
| keratin K79 | 338785 | NP_787028 |
| keratin K80 | 144501 | NP_001074961 |
| Mesenchymal | | |
| vimentin | 7431 | NP_003371 |

[1]The NCBI GeneID number is a unique identifier of the biomarker gene from the NCBI Entrez Gene database record (National Center for Biotechnology Information (NCBI), U.S. National Library of Medicine, 8600 Rockville Pike, Building 38A, Bethesda, MD 20894; Internet address http://www.ncbi.nlm.nih.gov/).
[2]The NCBI RefSeq (Reference Sequence) is an example of a sequence expressed by the biomarker gene.
[3]The new consensus nomenclature has been used herein when referring to keratins (see Schweizer, J. et al. (2006) J. Cell Biol. 174(2): 169-174). Former names for these proteins can be found in the latter reference, and at the Human Intermediate Filament Database (http://www.interfil.org/index.php). N.B. Epithelial keratins or cytokeratins are intermediate filament keratins. The terms "keratin" and "cytokeratin" are used synonymously herein. When refering to specific keratins in the text herein the "K" in the standard keratin designation (as in Table 2) is generally dropped (e.g. keratin K8 = keratin 8).

Table 1 lists genes coding for examples of epithelial or mesenchymal molecular biomarkers that can be used in the practice of the methods of the invention described herein. The epithelial or mesenchymal molecular biomarkers can include any product expressed by these genes, including variants thereof, e.g. expressed mRNA or protein, splice variants, coand post-translationally modified proteins, polymorphic variants etc. In one embodiment the biomarker is the embryonal EDB+ fibronectin, a splice variant expressed by the fibronectin 1 gene (Kilian, O. et al. (2004) Bone 35(6):1334-1345). A possible advantage of determining this fetal form of fibronectin is that one could readily distinguish mesenchymal-like tumors from surrounding stromal tissue. Table 2 lists genes coding for examples of molecular biomarkers that can be used in the practice of certain embodiments of the methods of the invention described herein wherein co-expression of epithelial keratin(s) and the mesenchymal biomarker vimentin at similar levels is indicative of a mesenchymal-like cell. The molecular biomarkers can include any product expressed by these genes, including variants thereof, e.g. expressed mRNA or protein, splice variants, co- and post-translationally modified proteins, polymorphic variants etc.

In another embodiment of any of the methods of the invention described herein, the mesenchymal biomarker utilized in the method is selected from the human transcriptional repressors Snail (NCBI GeneID 6615), Zeb1 (NCBI GeneID 6935), Twist (NCBI GeneID 7291), Sip1 NCBI GeneID 8487), and Slug (NCBI GeneID 6591).

In another embodiment of the methods of this invention the mesenchymal biomarker is methylation of the promoter of a gene whose transcription is repressed as a result of EMT in the tumor cell. In the context of this method high levels of a tumor cell mesenchymal biomarker essentially means readily detectable methylation of the promoter (e.g. a strong signal during detection of a methylation-specific PCR-amplified nucleic acid product derived from a promoter methylation site), whereas low levels of a tumor cell mesenchymal biomarker essentially means no detectable or low methylation of the promoter (e.g. no, or a comparatively weak, signal during detection of a methylation-specific PCR-amplified nucleic acid product derived from a promoter methylation site). In one embodiment of this method the gene whose transcription is repressed as a result of EMT in the tumor cell is the E-Cadherin gene (i.e. CDH1; NCBI GeneID 999). In another embodiment of this method the gene whose transcription is repressed as a result of EMT in the tumor cell is the γ-catenin gene (i.e. NCBI GeneID 3728). In another embodiment of this method the gene whose transcription is repressed as a result of EMT in the tumor cell is an α-catenin gene (e.g. NCBI GeneID 1495, 1496, or 29119). In another embodiment of this method the gene whose transcription is repressed as a result of EMT in the tumor cell is a cytokeratin gene (e.g. NCBI GeneID 3856 (keratin 8) or 3875 (keratin 18)).

Examples of additional epithelial markers that can be used in any of the methods of this invention include phospho-14-3-3 epsilon, 14-3-3 gamma (KCIP-1), 14-3-3 sigma (Stratifin), 14-3-3 zeta/delta, phospho-serine/threonine phosphatase 2A, 4F2hc (CD98 antigen), adenine nucleotide translocator 2, annexin A3, ATP synthase beta chain, phospho-insulin receptor substrate p53/p54, Basigin (CD147 antigen), phospho-CRK-associated substrate (p130Cas), Bcl-X, phospho-P-cadherin, phospho-calmodulin (CaM), Calpain-2 catalytic subunit, Cathepsin D, Cofilin-1Calpain small subunit 1, Catenin beta-1, Catenin delta-1 (p120 catenin), Cystatin B, phospho-DAZ-associated protein 1, Carbonyl reductase [NADPH], Diaphanous-related formin 1 (DRF1), Desmoglein-2, Elongation factor 1-delta, phospho-p185erbB2, Ezrin (p81), phospho-focal adhesion kinase 1, phospho-p94-FER (c-FER)., Filamin B, phospho-GRB2-associated binding protein 1, Rho-GDI alpha, phospho-GRB2, GRP 78, Glutathione S-transferase P, 3-hydroxyacyl-CoA dehydrogenase, HSP 90-alpha, HSP70.1, eIF3 p110, eIF-4E, Leukocyte elastase inhibitor, Importin-4, Integrin alpha-6, Integrin beta-4, phospho-Cytokeratin 17, Cytokeratin 19, Cytokeratin 7, Casein kinase I, alpha, Protein kinase C, delta, Pyruvate kinase, isozymes M1/M2phospho-Erbin, LIM and SH3 domain protein 1 (LASP-1), 4F21c (CD98 light chain), L-lactate dehydrogenase A chain, Galectin-3, Galectin-3 binding protein, phospho-LIN-7 homolog C, MAP (APC-binding protein EB1), Maspin precursor (Protease inhibitor 5), phospho-Met tyrosine kinase (HGF receptor), Mixed-lineage leukemia protein 2, Monocarboxylate transporter 4, phospho-C-Myc binding protein (AMY-1), Myosin-9, Myosin light polypeptide 6, Nicotinamide phosphoribosyltransferase, Niban-like protein (Meg-3), Ornithine aminotransferase, phospho-Occludin, Ubiquitin thiolesterase, PAF acetylhydrolase IB beta subunit, phospho-partitioning-defective 3 (PAR-3), phospho-programmed cell death 6-interacting protein, phospho-Programmed cell death protein 6, Protein disulfide-isomerase, phospho-plakophilin-2, phospho-plakophilin-3, Protein phosphatase 1, Peroxiredoxin 5, Proteasome activator complex subunit 1, Prothymosin alpha, Retinoic acid-induced protein 3, phospho-DNA repair protein REV1, Ribonuclease inhibitor, RuvB-like 1, S-100P, S-100L, Calcyclin, S100C, phospho-Sec23A, phospho-Sec23B, Lysosome membrane protein II (LIMP II), p60-Src, phospho-Amplaxin (EMS1), SLP-2, Gamma-synuclein, Tumor calcium signal transducer 1, Tumor calcium signal transducer 2, Transgelin-2, Transaldolase, Tubulin beta-2 chain, Translationally controlled (TCTP), Tissue transglutaminase, Transmembrane protein Tmp21, Ubiquitin-conjugating enzyme E2 N, UDP-glucosyltransferase 1, phospho-p61-Yes, phospho-Tight junction protein ZO-1, AHNAK (Desmoyokin), phospho-ATP synthase beta chain, phospho-ATP synthase delta, Cold shock domain protein E1, Desmoplakin III, Plectin 1, phospho-Nectin 2 (CD112 antigen), phospho-p185-Ron, phospho-SHC1, E-cadherin, Brk, γ-catenin, α1-catenin, α2-catenin, α3-catenin, keratin 8, keratin 18, connexin 31, plakophilin 3, stratafin 1, laminin alpha-5, ST14, and other epithelial biomarkers known in the art (see for example, US Patent Application Publication 2007/0212738; U.S. Patent Application 60/923,463; U.S. Patent Application 60/997,514). Where the epithelial biomarker is a phospho-"protein" the extent of phosphorylation of the protein rather than the level of the protein per se is the parameter that is altered after EMT. The altered level of phosphorylation of these proteins is also understood to be due to changes in the level of phosphorylation of one or more tyrosine residues of the protein (US Patent Application Publication 2007/0212738).

Examples of additional mesenchymal markers that can be used in any of the methods of this invention include MMP9 (matrix-metalloproteinase 9; NCBI Gene ID No. 4318), MHC class I antigen A*1, Acyl-CoA desaturase, LANP-like protein (LANP-L), Annexin A6, ATP synthase gamma chain, BAG-family molecular chaperone regulator-2, phospho-Bullous pemphigoid antigen, phospho-Protein C1orf77, CDK1 (cdc2), phospho-Clathrin heavy chain 1, Condensin complex subunit 1,3,2-trans-enoyl-CoA isomerase, DEAH-box protein 9, phospho-Enhancer of rudimentary homolog, phospho-Fibrillarin, GAPDH muscle, GAPDH liver, Synaptic glycoprotein SC2, phospho-Histone H1.0, phospho-Histone H1.2, phospho-Histone H1.3, phospho-Histone H1.4, phospho-Histone H1.5, phospho-Histone H1x, phospho-Histone H2AFX, phospho-Histone H2A.o, phospho-Histone H2A.q, phospho-Histone H2A.z, phospho-Histone H2B.j, phospho-Histone H2B.r, phospho-Histone H4, phospho-HMG-17-like 3, phospho-HMG-14, phospho-HMG-17, phospho-HMGI-C, phospho-HMG-I/HMG-Y, phospho-Thyroid receptor interacting protein 7 (TRIP7), phosphohnRNP H3, hnRNP C1/C2, hnRNP F, phospho-hnRNP G, eIF-5A, NFAT 45 kDa, Importin beta-3, cAMP-dependent PK1a, Lamin B1, Lamin A/C, phospho-Laminin alpha-3 chain, L-lactate dehydrogenase B chain, Galectin-1, phospho-Fez1, Hyaluronan-binding protein 1, phospho-Microtubule-actin crosslinking factor 1, Melanoma-associated antigen 4, Matrin-3, Phosphate carrier protein, Myosin-10, phospho-N-acylneuraminate cytidylyltransferase, phospho-NHP2-like protein 1, H/ACA ribonucleoprotein subunit 1, Nucleolar phosphoprotein p130, phospho-RNA-binding protein Nova-2, Nucleophosmin (NPM), NADH-ubiquinone oxidoreductase 39 kDa subunit, phospho-Polyadenylate-binding protein 2, Prohibitin, Prohibitin-2, Splicing factor Prp8, Polypyrimidine tract-binding protein 1, Parathymosin, Rab-2A, phospho-RNA-binding protein Raly, Putative RNA-binding protein 3, phospho-60S ribosomal protein L23, hnRNP A0, hnRNP A2/B1, hnRNP A/B, U2 small nuclear ribonucleoprotein B, phospho-Ryanodine receptor 3, phospho-Splicing factor 3A subunit 2, snRNP core protein D3, Nesprin-1, Tyrosine—tRNA ligase, phospho-Tankyrase 1-BP, Tubulin beta-3, Acetyl-CoA acetyltransferase, phospho-bZIP enhancing factor BEF (Aly/REF; Tho4), Ubiquitin, Ubiquitin carboxyl-terminal hydrolase 5, Ubiquinol-cytochrome c reductase, Vacuolar protein sorting 16, phospho-Zinc finger protein 64, phospho-AHNAK (Desmoyokin), ATP synthase beta chain, ATP synthase delta chain, phospho-Cold shock domain protein E1, phospho-Plectin 1, Nectin 2 (CD112 antigen), p185-Ron, SHC1, vimentin, fibronectin, fibrillin-1, fibrillin-2, collagen alpha-2(IV), collagen alpha-2 (V), LOXL1, nidogen, C11 or f9, tenascin, N-cadherin, embryonal EDB$^+$ fibronectin, tubulin alpha-3, epimorphin, and other mesenchymal biomarkers known in the art, (see for example, U.S. Patent Application Publication 2007/0212738; U.S. Patent Application 60/923,463; U.S. Patent Application 60/997,514). Where the mesenchymal biomarker is a phospho-"protein" the extent of phosphorylation of the protein rather than the level of the protein per se is the parameter that is altered after EMT. The altered level of phosphorylation of these proteins is also understood to be due to changes in the level of phosphorylation of one or more tyrosine residues of the protein (U.S. Patent Application Publication 2007/0212738).

The biomarkers in the above lists of epithelial and mesenchymal biomarkers have been identified as being altered in expression level (or phosphoylation level for phospho-"proteins") after EMT (see for example, US Patent Application Publication 2007/0212738, the contents of which are incorporated herein by reference; U.S. Published Application 2006/0211060 (filed Mar. 16, 2006); Thomson, S. et al. (2005) Cancer Res. 65(20) 9455-9462; and Yauch, R. L. et al. (2005) Clin. Can. Res. 11(24) 8686-8698).

In the methods of this invention, biomarker expression level can be assessed relative to a control molecule whose expression level remains constant throughout EMT or when comparing tumor cells expressing either epithelial or mesenchymal transition states as indicated by molecular biomarkers (e.g. a "housekeeping" gene, such as GAPDH, β-actin, tubulin, or the like). Biomarker expression level can also be assessed relative to the other type of tumor cell biomarker (i.e. epithelial compared to mesenchymal), or to the biomarker level in non-tumor cells of the same tissue, or another cell or tissue source used as an assay reference.

In the methods of this invention, the level of an epithelial or mesenchymal biomarker expressed by a tumor cell can be assessed by using any of the standard bioassay procedures known in the art for determination of the level of expression of a gene, including for example ELISA, RIA, immunoprecipitation, immunoblotting, immunofluorescence microscopy, immunohistochemistry (IHC), RT-PCR, in situ hybridization, cDNA microarray, or the like, as described in more detail below. In an embodiment of any of these methods, their use is coupled with a method to isolate a particular cell population, e.g. laser capture microdisection (LCM). In an additional embodiment, FACS analysis can be used with immunofluorescence biomarker (e.g. E-cadherin) labeling to isolate and quantify cell populations expressing different epithelial or mesenchymal biomarkers, and thus for example the percentage of cells that have undergone an EMT can be estimated (e.g. see Xu, Z. et al. (2003) Cell Research 13(5):343-350).

In the methods of this invention, the expression level of a tumor cell epithelial or mesenchymal biomarker in vivo is preferably assessed by assaying a tumor biopsy. In one embodiment the biopsy comprises samples taken from multiple areas of the tumor, or a method (e.g. core needle biopsy) that samples different areas of the tumor, thus ensuring that when the tumor is of a heterogeneous nature with respect to the types of cells it contains, that a representative biopsy is obtained. In an alternative embodiment, given that a tumor may be heterogeneous with respect to the EMT status of the cells it contains, the methods of this invention are preferably applied separately to different cell types (e.g. using IHC, or an analysis method coupled with a step to isolate a particular cell population). Alternatively, by employing cell surface epithelial and/or mesenchymal biomarker antibodies (e.g. to E-cadherin), FACS analysis can be used to isolate and quantify the numbers of tumor cells at different stages of EMT.

However, in an alternative embodiment, expression level of the tumor cell biomarker can be assessed in bodily fluids or excretions containing detectable levels of biomarkers originating from the tumor or tumor cells. Bodily fluids or excretions useful in the present invention include blood, urine, saliva, stool, pleural fluid, lymphatic fluid, sputum, ascites, prostatic fluid, cerebrospinal fluid (CSF), or any other bodily secretion or derivative thereof. By blood it is meant to include whole blood, plasma, serum or any derivative of blood. Assessment of tumor epithelial or mesenchymal biomarkers in such bodily fluids or excretions can sometimes be preferred in circumstances where an invasive sampling method is inappropriate or inconvenient.

For assessment of tumor cell epithelial or mesenchymal biomarker expression, tumor samples containing tumor cells, or proteins or nucleic acids produced by these tumor cells, may be used in the methods of the present invention. In these embodiments, the level of expression of the biomarker can be assessed by assessing the amount (e.g. absolute amount or concentration) of the marker in a tumor cell sample, e.g., a tumor biopsy obtained from an animal, or another sample containing material derived from the tumor (e.g. blood, serum, urine, or other bodily fluids or excretions as described herein above). The cell sample can, of course, be subjected to a variety of well-known post-collection preparative and storage techniques (e.g., nucleic acid and/or protein extraction, fixation, storage, freezing, ultrafiltration, concentration, evaporation, centrifugation, etc.) prior to assessing the amount of the marker in the sample. Likewise, tumor biopsies may also be subjected to post-collection preparative and storage techniques, e.g., fixation.

Determination of epithelial or mesenchymal biomarker levels in in vivo studies can be assessed by a number of different approaches, including direct analysis of proteins that segregate as epithelial related (e.g. E-cadherin) or mesenchymal related (e.g. vimentin, Zeb1) biomarkers. An advantage of this approach is that EMT markers are read directly, and the relative amounts of cell populations expressing epithelial or mesenchymal biomarkers can readily be examined and quantified, by for example FACS analysis (e.g. see Xu, Z. et al. (2003) Cell Research 13(5):343-350). However, this approach also requires sufficient quantities of cells or tissue in order to perform an analysis (e.g. immunohistochemistry). Sufficient quantities of tissue may be difficult to obtain from certain procedures such as FNA (fine needle aspiration). Core biopsies provide larger amounts of tissue, but are sometimes not readly available. Alternatively, these EMT biomarkers could be evaluated based upon the expression level of their encoding RNA transcripts using a quantitative PCR based approach. An advantage of this approach is that very few tumor cells are required for this measurement, and it is very likely that sufficient material may be obtained via an FNA. However, here the transcript levels for a given biomarker may be derived from both tumor cells as well as infiltrating stromal cells from the tumor. Given that stromal cells also express mesenchymal cell markers, this may obscure detection of the EMT status for tumor cells. Use of in situ hybridization (e.g. FISH) or tissue microdisection may be useful here to overcome this potential limitation.

Given that the expression level of E-cadherin is a hallmark of the EMT status for a tumor cell, EMT may also be evaluated based upon the methylation status of the E-cadherin promoter, as described herein. Methylation silences transcription, and so a high level of methylation correlates with a mesenchymal-like state. A potential benefit of this approach is that, like measurement of transcript levels, measuring the methylation status of DNA would likely require very little material. Sufficient material could likely be obtained from an FNA and would not require a core biopsy. Additionally, since this approach involves evaluation of DNA and not RNA, it is likely to be a more stable read-out over time, such as during medium or long term storage of a sample.

In the methods of the invention, one can detect expression of biomarker proteins having at least one portion which is displayed on the surface of tumor cells which express it. It is a simple matter for the skilled artisan to determine whether a marker protein, or a portion thereof, is exposed on the cell surface. For example, immunological methods may be used to detect such proteins on whole cells, or well known computer-based sequence analysis methods may be used to predict the presence of at least one extracellular domain (i.e. including both secreted proteins and proteins having at least one cell-surface domain). Expression of a marker protein having at least one portion which is displayed on the surface of a cell which expresses it may be detected without necessarily lysing the tumor cell (e.g. using a labeled antibody which binds specifically with a cell-surface domain of the protein).

Expression of a biomarkers described in this invention may be assessed by any of a wide variety of well known methods for detecting expression of a transcribed nucleic acid or protein. Non-limiting examples of such methods include immunological methods for detection of secreted, cell-surface, cytoplasmic, or nuclear proteins, protein purification methods, protein function or activity assays, nucleic acid hybridization methods, nucleic acid reverse transcription methods, and nucleic acid amplification methods.

In one embodiment, expression of a biomarker is assessed using an antibody (e.g. a radio-labeled, chromophore-labeled, fluorophore-labeled, or enzyme-labeled antibody), an antibody derivative (e.g. an antibody conjugated with a substrate or with the protein or ligand of a protein-ligand pair {e.g. biotin-streptavidin}), or an antibody fragment (e.g. a single-chain antibody, an isolated antibody hypervariable domain, etc.) which binds specifically with a biomarker protein or fragment thereof, including a biomarker protein which has undergone either all or a portion of post-translational modifications to which it is normally subjected in the tumor cell (e.g. glycosylation, phosphorylation, methylation etc.).

In another embodiment, expression of a biomarker is assessed by preparing mRNA/cDNA (i.e. a transcribed polynucleotide) from tumor cells, and by hybridizing the mRNA/cDNA with a reference polynucleotide which is a complement of a biomarker nucleic acid, or a fragment thereof cDNA can, optionally, be amplified using any of a variety of polymerase chain reaction methods prior to hybridization with the reference polynucleotide. Expression of one or more biomarkers can likewise be detected using quantitative PCR to assess the level of expression of the biomarker(s). Alternatively, any of the many known methods of detecting mutations or variants (e.g. single nucleotide polymorphisms, deletions, etc.) of a biomarker of the invention may be used to detect occurrence of a biomarker in a tumor cell.

In a related embodiment, a mixture of transcribed polynucleotides obtained from the sample is contacted with a substrate having fixed thereto a polynucleotide complementary to or homologous with at least a portion (e.g. at least 7, 10, 15, 20, 25, 30, 40, 50, 100, 500, or more nucleotide residues) of a biomarker nucleic acid. If polynucleotides complementary to or homologous with are differentially detectable on the substrate (e.g. detectable using different chromophores or fluorophores, or fixed to different selected positions), then the levels of expression of a plurality of biomarkers can be assessed simultaneously using a single substrate (e.g. a "gene chip" microarray of polynucleotides fixed at selected positions). When a method of assessing biomarker expression is used which involves hybridization of one nucleic acid with another, it is preferred that the hybridization be performed under stringent hybridization conditions.

When a plurality of biomarkers of the invention are used in the methods of the invention, the level of expression of each biomarker in tumor cells induced to undergo EMT can be compared with the level of expression of each of the plurality of biomarkers in non-induced samples of the same type, either in a single reaction mixture (i.e. using reagents, such as different fluorescent probes, for each biomarker) or in individual reaction mixtures corresponding to one or more of the biomarkers.

An exemplary method for detecting the presence or absence of a biomarker protein or nucleic acid in a biological sample involves obtaining a biological sample (e.g. a tumor-associated body fluid) from a test subject and contacting the biological sample with a compound or an agent capable of detecting the polypeptide or nucleic acid (e.g., mRNA, genomic DNA, or cDNA). The detection methods of the invention can thus be used to detect mRNA, protein, cDNA, or genomic DNA, for example, in a biological sample in vitro as well as in vivo. For example, in vitro techniques for detection of mRNA include Northern hybridizations and in situ hybridizations. In vitro techniques for detection of a biomarker protein include enzyme linked immunosorbent assays (ELISAs), Western blots, immunoprecipitations and immunofluorescence. In vitro techniques for detection of genomic DNA include Southern hybridizations. In vivo techniques for detection of mRNA include polymerase chain reaction (PCR), Northern hybridizations and in situ hybridizations. Furthermore, in vivo techniques for detection of a biomarker protein include introducing into a subject a labeled antibody directed against the protein or fragment thereof. For example, the antibody can be labeled with a radioactive marker whose presence and location in a subject can be detected by standard imaging techniques.

A general principle of such diagnostic and prognostic assays involves preparing a sample or reaction mixture that may contain a biomarker, and a probe, under appropriate conditions and for a time sufficient to allow the biomarker and probe to interact and bind, thus forming a complex that can be removed and/or detected in the reaction mixture. These assays can be conducted in a variety of ways.

For example, one method to conduct such an assay would involve anchoring the biomarker or probe onto a solid phase support, also referred to as a substrate, and detecting target biomarker/probe complexes anchored on the solid phase at the end of the reaction. In one embodiment of such a method, a sample from a subject, which is to be assayed for presence and/or concentration of biomarker, can be anchored onto a carrier or solid phase support. In another embodiment, the reverse situation is possible, in which the probe can be anchored to a solid phase and a sample from a subject can be allowed to react as an unanchored component of the assay.

There are many established methods for anchoring assay components to a solid phase. These include, without limitation, biomarker or probe molecules which are immobilized through conjugation of biotin and streptavidin. Such biotinylated assay components can be prepared from biotin-NHS (N-hydroxy-succinimide) using techniques known in the art (e.g., biotinylation kit, Pierce Chemicals, Rockford, Ill.), and immobilized in the wells of streptavidin-coated 96 well plates (Pierce Chemical). In certain embodiments, the surfaces with immobilized assay components can be prepared in advance and stored.

Other suitable carriers or solid phase supports for such assays include any material capable of binding the class of molecule to which the biomarker or probe belongs. Well-known supports or carriers include, but are not limited to, glass, polystyrene, nylon, polypropylene, nylon, polyethylene, dextran, amylases, natural and modified celluloses, polyacrylamides, gabbros, and magnetite.

In order to conduct assays with the above mentioned approaches, the non-immobilized component is added to the solid phase upon which the second component is anchored. After the reaction is complete, uncomplexed components may be removed (e.g., by washing) under conditions such that any complexes formed will remain immobilized upon the solid phase. The detection of biomarker/probe complexes anchored to the solid phase can be accomplished in a number of methods outlined herein.

In one embodiment, the probe, when it is the unanchored assay component, can be labeled for the purpose of detection and readout of the assay, either directly or indirectly, with detectable labels discussed herein and which are well-known to one skilled in the art.

It is also possible to directly detect biomarker/probe complex formation without further manipulation or labeling of either component (biomarker or probe), for example by utilizing the technique of fluorescence energy transfer (i.e. FET, see for example, Lakowicz et al., U.S. Pat. No. 5,631,169; Stavrianopoulos, et al., U.S. Pat. No. 4,868,103). A fluorophore label on the first, 'donor' molecule is selected such that, upon excitation with incident light of appropriate wavelength, its emitted fluorescent energy will be absorbed by a fluorescent label on a second 'acceptor' molecule, which in turn is able to fluoresce due to the absorbed energy. Alternately, the 'donor' protein molecule may simply utilize the natural fluorescent energy of tryptophan residues. Labels are chosen that emit different wavelengths of light, such that the 'acceptor' molecule label may be differentiated from that of the 'donor'. Since the efficiency of energy transfer between the labels is related to the distance separating the molecules, spatial relationships between the molecules can be assessed. In a situation in which binding occurs between the molecules, the fluorescent emission of the 'acceptor' molecule label in the assay should be maximal. An FET binding event can be conveniently measured through standard fluorometric detection means well known in the art (e.g., using a fluorimeter).

In another embodiment, determination of the ability of a probe to recognize a biomarker can be accomplished without labeling either assay component (probe or biomarker) by utilizing a technology such as real-time Biomolecular Interaction Analysis (BIA) (see, e.g., Sjolander, S. and Urbaniczky, C., 1991, Anal. Chem. 63:2338-2345 and Szabo et al., 1995, Curr. Opin. Struct. Biol. 5:699-705). As used herein, "BIA" or "surface plasmon resonance" is a technology for studying biospecific interactions in real time, without labeling any of the interactants (e.g., BIAcore). Changes in the mass at the binding surface (indicative of a binding event) result in alterations of the refractive index of light near the surface (the optical phenomenon of surface plasmon resonance (SPR)), resulting in a detectable signal which can be used as an indication of real-time reactions between biological molecules.

Alternatively, in another embodiment, analogous diagnostic and prognostic assays can be conducted with biomarker and probe as solutes in a liquid phase. In such an assay, the complexed biomarker and probe are separated from uncomplexed components by any of a number of standard techniques, including but not limited to: differential centrifugation, chromatography, electrophoresis and immunoprecipitation. In differential centrifugation, biomarker/probe complexes may be separated from uncomplexed assay components through a series of centrifugal steps, due to the different sedimentation equilibria of complexes based on their different sizes and densities (see, for example, Rivas, G., and Minton, A. P., 1993Trends Biochem Sci. 18(8):284-7). Standard chromatographic techniques may also be utilized to separate complexed molecules from uncomplexed ones. For example, gel filtration chromatography separates molecules based on size, and through the utilization of an appropriate gel filtration resin in a column format, for example, the relatively larger complex may be separated from the relatively smaller uncomplexed components. Similarly, the relatively different charge properties of the biomarker/probe complex as compared to the uncomplexed components may be exploited to differentiate the complex from uncomplexed components, for example through the utilization of ion-exchange chromatography resins. Such resins and chromatographic techniques are well known to one skilled in the art (see, e.g., Heegaard, N. H., 1998J. Mol. Recognit. Winter 11(1-6):141-8; Hage, D. S., and Tweed, S. A. J. Chromatogr B Biomed Sci Appl Oct. 10, 1997; 699(1-2):499-525). Gel electrophoresis may also be employed to separate complexed assay components from unbound components (see, e.g., Ausubel et al., ed., Current Protocols in Molecular Biology, John Wiley & Sons, New York, 1987-1999). In this technique, protein or nucleic acid complexes are separated based on size or charge, for example. In order to maintain the binding interaction during the electrophoretic process, non-denaturing gel matrix materials and conditions in the absence of reducing agent are typically preferred. Appropriate conditions to the particular assay and components thereof will be well known to one skilled in the art.

In a particular embodiment, the level of biomarker mRNA can be determined both by in situ and by in vitro formats in a biological sample using methods known in the art. The term "biological sample" is intended to include tissues, cells, biological fluids and isolates thereof, isolated from a subject, as well as tissues, cells and fluids present within a subject. Many expression detection methods use isolated RNA. For in vitro methods, any RNA isolation technique that does not select against the isolation of mRNA can be utilized for the purification of RNA from tumor cells (see, e.g., Ausubel et al., ed., Current Protocols in Molecular Biology, John Wiley & Sons, New York 1987-1999). Additionally, large numbers of tissue samples can readily be processed using techniques well known to those of skill in the art, such as, for example, the single-step RNA isolation process of Chomczynski (1989, U.S. Pat. No. 4,843,155).

The isolated mRNA can be used in hybridization or amplification assays that include, but are not limited to, Southern or Northern analyses, polymerase chain reaction analyses and probe arrays. One preferred diagnostic method for the detection of mRNA levels involves contacting the isolated mRNA with a nucleic acid molecule (probe) that can hybridize to the mRNA encoded by the gene being detected. The nucleic acid probe can be, for example, a full-length cDNA, or a portion thereof, such as an oligonucleotide of at least 7, 15, 30, 50, 100, 250 or 500 nucleotides in length and sufficient to specifically hybridize under stringent conditions to a mRNA or genomic DNA encoding a biomarker of the present invention. Other suitable probes for use in the diagnostic assays of the invention are described herein. Hybridization of an mRNA with the probe indicates that the biomarker in question is being expressed.

In one format, the mRNA is immobilized on a solid surface and contacted with a probe, for example by running the isolated mRNA on an agarose gel and transferring the mRNA from the gel to a membrane, such as nitrocellulose. In an alternative format, the probe(s) are immobilized on a solid surface and the mRNA is contacted with the probe(s), for example, in an Affymetrix gene chip array. A skilled artisan can readily adapt known mRNA detection methods for use in detecting the level of mRNA encoded by the biomarkers of the present invention.

An alternative method for determining the level of mRNA biomarker in a sample involves the process of nucleic acid amplification, e.g., by RT-PCR (the experimental embodiment set forth in Mullis, 1987 U.S. Pat. No. 4,683,202), ligase chain reaction (Barany, 1991, Proc. Natl. Acad. Sci. USA, 88:189-193), self sustained sequence replication (Guatelli et al., 1990, Proc. Natl. Acad. Sci. USA 87:1874-1878), transcriptional amplification system (Kwoh et al., 1989, Proc. Natl. Acad. Sci. USA 86:1173-1177), Q-Beta Replicase (Lizardi et al., 1988, Bio/Technology 6:1197), rolling circle replication (Lizardi et al., U.S. Pat. No. 5,854,033) or any other nucleic acid amplification method, followed by the detection of the amplified molecules using techniques well known to those of skill in the art. These detection schemes are especially useful for the detection of nucleic acid molecules if such molecules are present in very low numbers. As used herein, amplification primers are defined as being a pair of nucleic acid molecules that can anneal to 5' or 3' regions of a gene (plus and minus strands, respectively, or vice-versa) and contain a short region in between. In general, amplification primers are from about 10 to 30 nucleotides in length and flank a region from about 50 to 200 nucleotides in length. Under appropriate conditions and with appropriate reagents, such primers permit the amplification of a nucleic acid molecule comprising the nucleotide sequence flanked by the primers.

For in situ methods, mRNA does not need to be isolated from the tumor cells prior to detection. In such methods, a cell or tissue sample is prepared/processed using known histological methods. The sample is then immobilized on a support, typically a glass slide, and then contacted with a probe that can hybridize to mRNA that encodes the biomarker.

As an alternative to making determinations based on the absolute expression level of the biomarker, determinations may be based on the normalized expression level of the biomarker. Expression levels are normalized by correcting the absolute expression level of a biomarker by comparing its expression to the expression of a gene that is not a biomarker, e.g., a housekeeping gene that is constitutively expressed. Suitable genes for normalization include housekeeping genes such as the actin gene, or epithelial cell-specific genes. This normalization allows the comparison of the expression level in one sample, e.g., a tumor cell sample, to another sample, e.g., a non-tumor sample, or between samples from different sources, or between samples before and after induction of EMT.

Alternatively, the expression level can be provided as a relative expression level. To determine a relative expression level of a biomarker (e.g. a mesenchymal biomarker), the level of expression of the biomarker is determined for 10 or more samples of normal versus cancer cell isolates, preferably 50 or more samples, prior to the determination of the expression level for the sample in question. The mean expression level of each of the genes assayed in the larger number of samples is determined and this is used as a baseline expression level for the biomarker. The expression level of the biomarker determined for the test sample (absolute level of expression) is then divided by the mean expression value obtained for that biomarker. This provides a relative expression level.

In another embodiment of the present invention, a biomarker protein is detected. A preferred agent for detecting biomarker protein of the invention is an antibody capable of binding to such a protein or a fragment thereof, preferably an antibody with a detectable label. Antibodies can be polyclonal, or more preferably, monoclonal. An intact antibody, or a fragment or derivative thereof (e.g., Fab or F(ab').sub.2) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin.

Proteins from tumor cells can be isolated using techniques that are well known to those of skill in the art. The protein isolation methods employed can, for example, be such as those described in Harlow and Lane (Harlow and Lane, 1988, Antibodies: A Laboratory Manual, Cold Spring Harbor Laboratory Press, Cold Spring Harbor, N.Y.).

A variety of formats can be employed to determine whether a sample contains a protein that binds to a given antibody. Examples of such formats include, but are not limited to, enzyme immunoassay (EIA), radioimmunoassay (RIA), Western blot analysis and enzyme linked immunoabsorbent assay (ELISA). A skilled artisan can readily adapt known protein/antibody detection methods for use in determining whether tumor cells express a biomarker of the present invention.

In one format, antibodies, or antibody fragments or derivatives, can be used in methods such as Western blots or immunofluorescence techniques to detect the expressed proteins. In such uses, it is generally preferable to immobilize either the antibody or proteins on a solid support. Suitable solid phase supports or carriers include any support capable of binding an antigen or an antibody. Well-known supports or carriers include glass, polystyrene, polypropylene, polyethylene, dextran, nylon, amylases, natural and modified celluloses, polyacrylamides, gabbros, and magnetite.

One skilled in the art will know many other suitable carriers for binding antibody or antigen, and will be able to adapt such support for use with the present invention. For example, protein isolated from tumor cells can be run on a polyacrylamide gel electrophoresis and immobilized onto a solid phase support such as nitrocellulose. The support can then be washed with suitable buffers followed by treatment with the detectably labeled antibody. The solid phase support can then be washed with the buffer a second time to remove unbound antibody. The amount of bound label on the solid support can then be detected by conventional means.

For ELISA assays, specific binding pairs can be of the immune or non-immune type. Immune specific binding pairs are exemplified by antigen-antibody systems or hapten/anti-hapten systems. There can be mentioned fluorescein/anti-fluorescein, dinitrophenyl/anti-dinitrophenyl, biotin/anti-biotin, peptide/anti-peptide and the like. The antibody member of the specific binding pair can be produced by customary methods familiar to those skilled in the art. Such methods involve immunizing an animal with the antigen member of the specific binding pair. If the antigen member of the specific binding pair is not immunogenic, e.g., a hapten, it can be covalently coupled to a carrier protein to render it immunogenic. Non-immune binding pairs include systems wherein the two components share a natural affinity for each other but are not antibodies. Exemplary non-immune pairs are biotin-streptavidin, intrinsic factor-vitamin $B_{12}$, folic acid-folate binding protein and the like.

A variety of methods are available to covalently label antibodies with members of specific binding pairs. Methods are selected based upon the nature of the member of the specific binding pair, the type of linkage desired, and the tolerance of the antibody to various conjugation chemistries. Biotin can be covalently coupled to antibodies by utilizing commercially available active derivatives. Some of these are biotin-N-hydroxy-succinimide which binds to amine groups on proteins; biotin hydrazide which binds to carbohydrate moieties, aldehydes and carboxyl groups via a carbodiimide coupling; and biotin maleimide and iodoacetyl biotin which bind to sulfhydryl groups. Fluorescein can be coupled to protein amine groups using fluorescein isothiocyanate. Dinitrophenyl groups can be coupled to protein amine groups using 2,4-dinitrobenzene sulfate or 2,4-dinitrofluorobenzene. Other standard methods of conjugation can be employed to couple monoclonal antibodies to a member of a specific binding pair including dialdehyde, carbodiimide coupling, homofunctional crosslinking, and heterobifunctional crosslinking. Carbodiimide coupling is an effective method of coupling carboxyl groups on one substance to amine groups on another. Carbodiimide coupling is facilitated by using the commercially available reagent 1-ethyl-3-(dimethyl-aminopropyl)-carbodiimide (EDAC).

Homobifunctional crosslinkers, including the bifunctional imidoesters and bifunctional N-hydroxysuccinimide esters, are commercially available and are employed for coupling amine groups on one substance to amine groups on another. Heterobifunctional crosslinkers are reagents which possess different functional groups. The most common commercially available heterobifunctional crosslinkers have an amine reactive N-hydroxysuccinimide ester as one functional group, and a sulfhydryl reactive group as the second functional group. The most common sulfhydryl reactive groups are maleimides, pyridyl disulfides and active halogens. One of the functional groups can be a photoactive aryl nitrene, which upon irradiation reacts with a variety of groups.

The detectably-labeled antibody or detectably-labeled member of the specific binding pair is prepared by coupling to a reporter, which can be a radioactive isotope, enzyme, fluorogenic, chemiluminescent or electrochemical materials. Two commonly used radioactive isotopes are $^{125}I$ and $^{3}H$. Standard radioactive isotopic labeling procedures include the chloramine T, lactoperoxidase and Bolton-Hunter methods for $^{125}I$ and reductive methylation for $^{3}H$. The term "detectably-labeled" refers to a molecule labeled in such a way that it can be readily detected by the intrinsic enzymic activity of the label or by the binding to the label of another component, which can itself be readily detected.

Enzymes suitable for use in this invention include, but are not limited to, horseradish peroxidase, alkaline phosphatase, β-galactosidase, glucose oxidase, luciferases, including firefly and *renilla*, β-lactamase, urease, green fluorescent protein (GFP) and lysozyme. Enzyme labeling is facilitated by using dialdehyde, carbodiimide coupling, homobifunctional crosslinkers and heterobifunctional crosslinkers as described above for coupling an antibody with a member of a specific binding pair.

The labeling method chosen depends on the functional groups available on the enzyme and the material to be labeled, and the tolerance of both to the conjugation conditions. The labeling method used in the present invention can be one of, but not limited to, any conventional methods currently employed including those described by Engvall and Pearlmann, Immunochemistry 8, 871 (1971), Avrameas and Ternynck, Immunochemistry 8, 1175 (1975), Ishikawa et al., J. Immunoassay 4(3):209-327 (1983) and Jablonski, Anal. Biochem. 148:199 (1985).

Labeling can be accomplished by indirect methods such as using spacers or other members of specific binding pairs. An example of this is the detection of a biotinylated antibody with unlabeled streptavidin and biotinylated enzyme, with streptavidin and biotinylated enzyme being added either sequentially or simultaneously. Thus, according to the present invention, the antibody used to detect can be detectably-labeled directly with a reporter or indirectly with a first member of a specific binding pair. When the antibody is coupled to a first member of a specific binding pair, then detection is effected by reacting the antibody-first member of a specific binding complex with the second member of the binding pair that is labeled or unlabeled as mentioned above.

Moreover, the unlabeled detector antibody can be detected by reacting the unlabeled antibody with a labeled antibody specific for the unlabeled antibody. In this instance "detectably-labeled" as used above is taken to mean containing an epitope by which an antibody specific for the unlabeled antibody can bind. Such an anti-antibody can be labeled directly or indirectly using any of the approaches discussed above. For example, the anti-antibody can be coupled to biotin which is detected by reacting with the streptavidin-horseradish peroxidase system discussed above.

In one embodiment of this invention biotin is utilized. The biotinylated antibody is in turn reacted with streptavidin-horseradish peroxidase complex. Orthophenylenediamine, 4-chloro-naphthol, tetramethylbenzidine (TMB), ABTS, BTS or ASA can be used to effect chromogenic detection.

In one immunoassay format for practicing this invention, a forward sandwich assay is used in which the capture reagent has been immobilized, using conventional techniques, on the surface of a support. Suitable supports used in assays include synthetic polymer supports, such as polypropylene, polystyrene, substituted polystyrene, e.g. aminated or carboxylated polystyrene, polyacrylamides, polyamides, polyvinylchloride, glass beads, agarose, or nitrocellulose.

Agents, or compositions comprising such agents, that inhibit tumor cells from undergoing an epithelial to mesenchymal transition, inhibit tumor cells that have undergone an epithelial to mesenchymal transition, or stimulate mesenchymal-like tumor cells to undergo a mesenchymal to epithelial transition, identified by the methods described herein, can be used in methods for treating tumors or tumor metastases in a patient.

As used herein, the term "patient" preferably refers to a human in need of treatment with an anti-cancer agent for any purpose, and more preferably a human in need of such a treatment to treat cancer, or a precancerous condition or lesion. However, the term "patient" can also refer to non-human animals, preferably mammals such as dogs, cats, horses, cows, pigs, sheep and non-human primates, among others, that are in need of treatment with an anti-cancer agent.

Anti-cancer agents identified by any of the methods described herein (or compositions comprising them) can be used to treat any of the following tumors or cancers: NSCL, breast, colon, or pancreatic cancer, lung cancer, bronchioloalveolar cell lung cancer, bone cancer, skin cancer, cancer of the head or neck, cutaneous or intraocular melanoma, uterine cancer, ovarian cancer, rectal cancer, cancer of the anal region, stomach cancer, gastric cancer, uterine cancer, carcinoma of the fallopian tubes, carcinoma of the endometrium, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, cancer of the bladder, cancer of the ureter, cancer of the kidney, renal cell carcinoma, carcinoma of the renal pelvis, mesothelioma, hepatocellular cancer, biliary cancer, chronic or acute leukemia, lymphocytic lymphomas, neoplasms of the central nervous system (CNS), spinal axis tumors, brain stem glioma, glioblastoma multiforme, astrocytomas, schwannomas, ependymomas, medulloblastomas, meningiomas, squamous cell carcinomas, pituitary adenomas, including refractory versions of any of the above cancers, or a combination of one or more of the above cancers.

The term "refractory" as used herein is used to define a cancer for which treatment (e.g. chemotherapy drugs, biological agents, and/or radiation therapy) has proven to be ineffective. A refractory cancer tumor may shrink, but not to the point where the treatment is determined to be effective. Typically however, the tumor stays the same size as it was before treatment (stable disease), or it grows (progressive disease).

Anti-cancer agents identified by any of the methods described herein (or compositions comprising them) can be used to treat abnormal cell growth.

It will be appreciated by one of skill in the medical arts that the exact manner of administering to said patient of a therapeutically effective amount of the identified agent, e.g. in a combination of an EGFR kinase inhibitor and said agent, will be at the discretion of the attending physician. The mode of administration, including dosage, combination with other anti-cancer agents, timing and frequency of administration, and the like, may be affected by e.g. a diagnosis of a patient's likely responsiveness to an EGFR or IGFR kinase inhibitor, as well as the patient's condition and history. Thus, even patients diagnosed with tumors predicted to be relatively sensitive to e.g. an EGFR or IGFR kinase inhibitor as a single agent may still benefit from treatment with a combination of such a kinase inhibitor and the identified agent, optionally in combination with other anti-cancer agents, or other agents that may alter a tumor's sensitivity to kinase inhibitors.

In the context of this invention, an "effective amount" of an agent or therapy is as defined above. A "sub-therapeutic amount" of an agent or therapy is an amount less than the effective amount for that agent or therapy, but when combined with an effective or sub-therapeutic amount of another agent or therapy can produce a result desired by the physician, due to, for example, synergy in the resulting efficacious effects, or reduced side effects.

Additionally, the present invention provides a pharmaceutical composition comprising a combination of for example an EGFR or IGFR kinase inhibitor and the identified agent in a pharmaceutically acceptable carrier.

The invention also encompasses a pharmaceutical composition prepared by any of the methods described herein, that is comprised of an agent that inhibits tumor cells from undergoing an epithelial to mesenchymal transition, inhibit tumor cells that have undergone an epithelial to mesenchymal transition, or stimulate mesenchymal-like tumor cells to undergo a mesenchymal to epithelial transition, identified by any of the methods described herein (i.e. "the identified agent"), in combination with a pharmaceutically acceptable carrier, and optionally in combination with one or more other anti-cancer agents (e.g. an EGFR, IGF-1R, RON or MET receptor tyrosine kinase inhibitor).

Methods of preparing pharmaceutical compositions are well known in the art, as for example described in references such as Remington's Pharmaceutical Sciences, Mack Publishing Company, Easton, Pa., 18$^{th}$ edition (1990).

Preferably the composition is comprised of a pharmaceutically acceptable carrier and a non-toxic therapeutically effective amount of the identified agent (including pharmaceutically acceptable salts of each component thereof).

Moreover, within this preferred embodiment, the invention encompasses a pharmaceutical composition for the treatment of disease, the use of which results in the inhibition of growth of neoplastic cells, benign or malignant tumors, or metastases, comprising a pharmaceutically acceptable carrier and a non-toxic therapeutically effective amount of the identified agent (including pharmaceutically acceptable salts of each component thereof).

The term "pharmaceutically acceptable salts" refers to salts prepared from pharmaceutically acceptable non-toxic bases or acids. When a compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (cupric and cuprous), ferric, ferrous, lithium, magnesium, manganese (manganic and manganous), potassium, sodium, zinc and the like salts. Particularly preferred are the ammonium, calcium, magnesium, potassium and sodium salts. Salts derived from pharmaceutically acceptable organic non-toxic bases include salts of primary, secondary, and tertiary amines, as well as cyclic amines and substituted amines such as naturally occurring and synthesized substituted amines. Other pharmaceutically acceptable organic non-toxic bases from which salts can be formed include ion exchange resins such as, for example, arginine, betaine, caffeine, choline, N',N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

When a compound of the present invention is basic, its corresponding salt can be conveniently prepared from pharmaceutically acceptable non-toxic acids, including inorganic and organic acids. Such acids include, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Particularly preferred are citric, hydrobromic, hydrochloric, maleic, phosphoric, sulfuric and tartaric acids.

The pharmaceutical compositions of the present invention comprise the identified agent (including pharmaceutically acceptable salts thereof) as active ingredient, a pharmaceutically acceptable carrier and optionally other therapeutic ingredients or adjuvants. Other therapeutic agents may include those cytotoxic, chemotherapeutic or anti-cancer agents, or agents which enhance the effects of such agents, as listed above. The compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions may be conveniently presented in unit dosage form and prepared by any of the methods well known in the art of pharmacy.

In practice, the compounds represented by the identified agent (including pharmaceutically acceptable salts thereof) of this invention can be combined as the active ingredient in intimate admixture with a pharmaceutical carrier according to conventional pharmaceutical compounding techniques. The carrier may take a wide variety of forms depending on the form of preparation desired for administration, e.g. oral or parenteral (including intravenous). Thus, the pharmaceutical compositions of the present invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion, or as a water-in-oil liquid emulsion. In addition to the common dosage forms set out above, the identified agent (including pharmaceutically acceptable salts thereof) may also be administered by controlled release means and/or delivery devices. The combination compositions may be prepared by any of the methods of pharmacy. In general, such methods include a step of bringing into association the active ingredients with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

Thus, the pharmaceutical compositions of this invention may include a pharmaceutically acceptable carrier and a combination of the identified agent (including pharmaceutically acceptable salts thereof). The identified agent (including pharmaceutically acceptable salts thereof), can also be included in pharmaceutical compositions in combination with one or more other therapeutically active compounds. Other therapeutically active compounds may include those cytotoxic, chemotherapeutic or anti-cancer agents, or agents which enhance the effects of such agents, as listed above.

Thus in one embodiment of this invention, a pharmaceutical composition can comprise the identified agent in combination with an anticancer agent, wherein said anti-cancer agent is a member selected from the group consisting of alkylating drugs, antimetabolites, microtubule inhibitors, podophyllotoxins, antibiotics, nitrosoureas, hormone therapies, kinase inhibitors, activators of tumor cell apoptosis, and antiangiogenic agents.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In preparing the compositions for oral dosage form, any convenient pharmaceutical media may be employed. For example, water, glycols, oils, alcohols, flavoring agents, preservatives, coloring agents, and the like may be used to form oral liquid preparations such as suspensions, elixirs and solutions; while carriers such as starches, sugars, microcrystalline cellulose, diluents, granulating agents, lubricants, binders, disintegrating agents, and the like may be used to form oral solid preparations such as powders, capsules and tablets. Because of their ease of administration, tablets and capsules are the preferred oral dosage units whereby solid pharmaceutical carriers are employed. Optionally, tablets may be coated by standard aqueous or nonaqueous techniques.

A tablet containing the composition of this invention may be prepared by compression or molding, optionally with one or more accessory ingredients or adjuvants. Compressed tablets may be prepared by compressing, in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Each tablet preferably contains from about 0.05 mg to about 5 g of the active ingredient and each cachet or capsule preferably contains from about 0.05 mg to about 5 g of the active ingredient.

For example, a formulation intended for the oral administration to humans may contain from about 0.5 mg to about 5 g of active agent, compounded with an appropriate and convenient amount of carrier material that may vary from about 5 to about 95 percent of the total composition. Unit dosage forms will generally contain between from about 1 mg to about 2 g of the active ingredient, typically 25 mg, 50 mg, 100 mg, 200 mg, 300 mg, 400 mg, 500 mg, 600 mg, 800 mg, or 100 mg.

Pharmaceutical compositions of the present invention suitable for parenteral administration may be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), vegetable oils, and suitable mixtures thereof.

Pharmaceutical compositions of the present invention can be in a form suitable for topical sue such as, for example, an aerosol, cream, ointment, lotion, dusting powder, or the like. Further, the compositions can be in a form suitable for use in transdermal devices. These formulations may be prepared, utilizing the identified agent (including pharmaceutically acceptable salts thereof) of this invention, via conventional processing methods. As an example, a cream or ointment is prepared by admixing hydrophilic material and water, together with about 5 wt % to about 10 wt % of the compound, to produce a cream or ointment having a desired consistency.

Pharmaceutical compositions of this invention can be in a form suitable for rectal administration wherein the carrier is a solid. It is preferable that the mixture forms unit dose suppositories. Suitable carriers include cocoa butter and other materials commonly used in the art. The suppositories may be conveniently formed by first admixing the composition with the softened or melted carrier(s) followed by chilling and shaping in molds.

In addition to the aforementioned carrier ingredients, the pharmaceutical formulations described above may include, as appropriate, one or more additional carrier ingredients such as diluents, buffers, flavoring agents, binders, surface-active agents, thickeners, lubricants, preservatives (including anti-oxidants) and the like. Furthermore, other adjuvants can be included to render the formulation isotonic with the blood of the intended recipient. Compositions containing the identified agent (including pharmaceutically acceptable salts thereof) may also be prepared in powder or liquid concentrate form.

In the context of this invention, other anticancer agents includes, for example, other cytotoxic, chemotherapeutic or anti-cancer agents, or compounds that enhance the effects of such agents, anti-hormonal agents, angiogenesis inhibitors, tumor cell pro-apoptotic or apoptosis-stimulating agents, signal transduction inhibitors, anti-proliferative agents, anti-HER2 antibody or an immunotherapeutically active fragment thereof, anti-proliferative agents, COX II (cyclooxygenase II) inhibitors, and agents capable of enhancing antitumor immune responses.

In the context of this invention, other cytotoxic; chemotherapeutic or anti-cancer agents, or compounds that enhance the effects of such agents, include, for example: alkylating agents or agents with an alkylating action, such as cyclophosphamide (CTX; e.g. CYTOXAN®), chlorambucil (CHL; e.g. LEUKERAN®), cisplatin (CisP; e.g. PLATINOL®) busulfan (e.g. MYLERAN®), melphalan, carmustine (BCNU), streptozotocin, triethylenemelamine (TEM), mitomycin C, and the like; anti-metabolites, such as methotrexate (MTX), etoposide (VP16; e.g. VEPESID®), 6-mercaptopurine (6MP), 6-thioguanine (6TG), cytarabine (Ara-C), 5-fluorouracil (5-FU), capecitabine (e.g. XELODA®), dacarbazine (DTIC), and the like; antibiotics, such as actinomycin D, doxorubicin (DXR; e.g. ADRIAMYCIN®), daunorubicin (daunomycin), bleomycin, mithramycin and the like; alkaloids, such as vinca alkaloids such as vincristine (VCR), vinblastine, and the like; and other antitumor agents, such as paclitaxel (e.g. TAXOL®) and pactitaxel derivatives, the cytostatic agents, glucocorticoids such as dexamethasone (DEX; e.g. DECADRON®) and corticosteroids such as prednisone, nucleoside enzyme inhibitors such as hydroxyurea, amino acid depleting enzymes such as asparaginase, leucovorin and other folic acid derivatives, and similar, diverse antitumor agents. The following agents may also be used as additional agents: amifostine (e.g. ETHYOL®), dactinomycin, mechlorethamine (nitrogen mustard), streptozocin, cyclophosphamide, lomustine (CCNU), doxorubicin lipo (e.g. DOXIL®), gemcitabine (e.g. GEMZAR®), daunorubicin lipo (e.g. DAUNOXOME®), procarbazine, mitomycin, docetaxel (e.g. TAXOTERE®), aldesleukin, carboplatin, oxaliplatin, cladribine, camptothecin, CPT 11 (irinotecan), 10-hydroxy 7-ethyl-camptothecin (SN38), floxuridine, fludarabine, ifosfamide, idarubicin, mesna, interferon beta, interferon alpha, mitoxantrone, topotecan, leuprolide, megestrol, melphalan, mercaptopurine, plicamycin, mitotane, pegaspargase, pentostatin, pipobroman, plicamycin, tamoxifen, teniposide, testolactone, thioguanine, thiotepa, uracil mustard, vinorelbine, chlorambucil.

As used herein, the term "anti-hormonal agent" includes natural or synthetic organic or peptidic compounds that act to regulate or inhibit hormone action on tumors. Antihormonal agents include, for example: steroid receptor antagonists, anti-estrogens such as tamoxifen, raloxifene, aromatase inhibiting 4(5)-imidazoles, other aromatase inhibitors, 42-hydroxytamoxifen, trioxifene, keoxifene, LY 117018, onapristone, and toremifene (e.g. FARESTON®); anti-androgens such as flutamide, nilutamide, bicalutamide, leuprolide, and goserelin; and pharmaceutically acceptable salts, acids or derivatives of any of the above; agonists and/or antagonists of glycoprotein hormones such as follicle stimulating hormone (FSH), thyroid stimulating hormone (TSH), and luteinizing hormone (LH) and LHRH (leuteinizing hormone-releasing hormone); the LHRH agonist goserelin acetate, commercially available as ZOLADEX® (AstraZeneca); the LHRH antagonist D-alaninamide N-acetyl-3-(2-naphthalenyl)-D-alanyl-4-chloro-D-phenylalanyl-3-(3-pyridinyl)-D-alanyl-L-seryl-N6-(3-pyridinylcarbonyl)-L-lysyl-N6-(3-pyridinylcarbonyl)-D-lysyl-L-leucyl-N6-(1-methylethyl)-L-lysyl-L-proline (e.g ANTIDE®, Ares-Serono); the LHRH antagonist ganirelix acetate; the steroidal anti-androgens cyproterone acetate (CPA) and megestrol acetate, commercially available as MEGACE®(Bristol-Myers Oncology); the nonsteroidal anti-androgen flutamide (2-methyl-N-[4, 20-nitro-3-(trifluoromethyl)phenylpropanamide), commercially available as EULEXIN®(Schering Corp.); the non-steroidal anti-androgen nilutamide, (5,5-dimethyl-3-[4-nitro-3-(trifluoromethyl-4'-nitrophenyl)-4,4-dimethyl-imidazolidine-dione); and antagonists for other nonpermissive receptors, such as antagonists for RAR, RXR, TR, VDR, and the like.

Anti-angiogenic agents include, for example: VEGFR inhibitors, such as SU-5416 and SU-6668 (Sugen Inc. of South San Francisco, Calif., USA), or as described in, for example International Application Nos. WO 99/24440, WO 99/62890, WO 95/21613, WO 99/61422, WO 98/50356, WO 99/10349, WO 97/32856, WO 97/22596, WO 98/54093, WO 98/02438, WO 99/16755, and WO 98/02437, and U.S. Pat. Nos. 5,883,113, 5,886,020, 5,792,783, 5,834,504 and 6,235,764; VEGF inhibitors such as IM862 (Cytran Inc. of Kirkland, Wash., USA); angiozyme, a synthetic ribozyme from Ribozyme (Boulder, Colo.) and Chiron (Emeryville, Calif.); and antibodies to VEGF, such as bevacizumab (e.g. AVASTIN™, Genentech, South San Francisco, Calif.), a recombinant humanized antibody to VEGF; integrin receptor antagonists and integrin antagonists, such as to $\alpha_v\beta_3$, $\alpha_v\beta_5$ and $\alpha_v\beta_6$ integrins, and subtypes thereof, e.g. cilengitide (EMD 121974), or the anti-integrin antibodies, such as for example $\alpha_v\beta_3$ specific humanized antibodies (e.g. VITAXIN®); factors such as IFN-alpha (U.S. Pat. Nos. 4,530,901, 4,503,035 and 5,231,176); angiostatin and plasminogen fragments (e.g. kringle 1-4, kringle 5, kringle 1-3 (O'Reilly, M. S. et al. (1994) Cell 79:315-328; Cao et al. (1996) J. Biol. Chem. 271: 29461-29467; Cao et al. (997) J. Biol. Chem. 272:22924-22928); endostatin (O'Reilly, M. S. et al. (1997) Cell 88:277; and International Patent Publication No. WO 97/15666); thrombospondin (TSP-1; Frazier, (1991) Curr. Opin. Cell Biol. 3:792); platelet factor 4 (PF4); plasminogen activator/urokinase inhibitors; urokinase receptor antagonists; heparinases; fumagillin analogs such as TNP-4701; suramin and suramin analogs; angiostatic steroids; bFGF antagonists; flk-1 and flt-1 antagonists; anti-angiogenesis agents such as MMP-2 (matrix-metalloproteinase 2) inhibitors and MMP-9 (matrix-metalloproteinase 9) inhibitors. Examples of useful matrix metalloproteinase inhibitors are described in International Patent Publication Nos. WO 96/33172, WO 96/27583, WO 98/07697, WO 98/03516, WO 98/34918, WO 98/34915, WO 98/33768, WO 98/30566, WO 90/05719, WO 99/52910, WO 99/52889, WO 99/29667, and WO 99/07675, European Patent Publication Nos. 818,442, 780,386, 1,004,578, 606, 046, and 931,788; Great Britain Patent Publication No. 9912961, and U.S. Pat. Nos. 5,863,949 and 5,861,510. Preferred MMP-2 and MMP-9 inhibitors are those that have little or no activity inhibiting MMP-1. More preferred, are those that selectively inhibit MMP-2 and/or MMP-9 relative to the other matrix-metalloproteinases (i.e. MMP-1, MMP-3, MMP-4, MMP-5, MMP-6, MMP-7, MMP-8, MMP-10, MMP-11, MMP-12, and MMP-13).

Signal transduction inhibitors include, for example: erbB2 receptor inhibitors, such as organic molecules, or antibodies that bind to the erbB2 receptor, for example, trastuzumab (e.g. HERCEPTIN®); inhibitors of other protein tyrosine-kinases, e.g. imitinib (e.g. GLEEVEC®); ras inhibitors; raf inhibitors; MEK inhibitors; mTOR inhibitors; cyclin dependent kinase inhibitors; protein kinase C inhibitors; and PDK-1 inhibitors (see Dancey, J. and Sausville, E. A. (2003) Nature Rev. Drug Discovery 2:92-313, for a description of several examples of such inhibitors, and their use in clinical trials for the treatment of cancer).

ErbB2 receptor inhibitors include, for example: ErbB2 receptor inhibitors, such as GW-282974 (Glaxo Wellcome plc), monoclonal antibodies such as AR-209 (Aronex Pharmaceuticals Inc. of The Woodlands, Tex., USA) and 2B-1 (Chiron), and erbB2 inhibitors such as those described in International Publication Nos. WO 98/02434, WO 99/35146, WO 99/35132, WO 98/02437, WO 97/13760, and WO 95/19970, and U.S. Pat. Nos. 5,587,458, 5,877,305, 6,465,449 and 6,541,481.

Antiproliferative agents include, for example: Inhibitors of the enzyme farnesyl protein transferase and inhibitors of the receptor tyrosine kinase PDGFR, including the compounds disclosed and claimed in U.S. Pat. Nos. 6,080,769, 6,194,438, 6,258,824, 6,586,447, 6,071,935, 6,495,564, 6,150,377, 6,596,735 and 6,479,513, and International Patent Publication WO 01/40217. Antiproliferative agents also include inhibitors of the receptor tyrosine kinases IGF-1R and FGFR.

Examples of useful COX-II inhibitors include alecoxib (e.g. CELEBREX™), valdecoxib, and rofecoxib. Agents capable of enhancing antitumor immune responses include, for example: CTLA4 (cytotoxic lymphocyte antigen 4) antibodies (e.g. MDX-CTLA4), and other agents capable of blocking CTLA4. Specific CTLA4 antibodies that can be used in the present invention include those described in U.S. Pat. No. 6,682,736.

The present invention further provides a method for treating tumors or tumor metastases in a patient, comprising administering to the patient simultaneously or sequentially a therapeutically effective amount of the identified agent described herein above and optionally one or more other anticancer agents.

Dosage levels for the identified agents of this invention will be as described herein, but will depend upon a variety of factors including the age, body weight, general health, sex, diet, time of administration, route of administration, rate of excretion, drug combination and the severity of the particular disease undergoing therapy.

The use of the cytotoxic and other anticancer agents described above in chemotherapeutic regimens is generally well characterized in the cancer therapy arts, and their use herein falls under the same considerations for monitoring tolerance and effectiveness and for controlling administration routes and dosages, with some adjustments. For example, the actual dosages of the cytotoxic agents may vary depending upon the patient's cultured cell response determined by using histoculture methods. Generally, the dosage will be reduced compared to the amount used in the absence of additional other agents.

Typical dosages of an effective cytotoxic agent can be in the ranges recommended by the manufacturer, and where indicated by in vitro responses or responses in animal models, can be reduced by up to about one order of magnitude concentration or amount. Thus, the actual dosage will depend upon the judgment of the physician, the condition of the patient, and the effectiveness of the therapeutic method based on the in vitro responsiveness of the primary cultured malignant cells or histocultured tissue sample, or the responses observed in the appropriate animal models.

As used herein, the term "EGFR kinase inhibitor" refers to any EGFR kinase inhibitor that is currently known in the art or that will be identified in the future, and includes any chemical entity that, upon administration to a patient, results in inhibition of a biological activity associated with activation of the EGF receptor in the patient, including any of the downstream biological effects otherwise resulting from the binding to EGFR of its natural ligand. Such EGFR kinase inhibitors include any agent that can block EGFR activation or any of the downstream biological effects of EGFR activation that are relevant to treating cancer in a patient. Such an inhibitor can act by binding directly to the intracellular domain of the receptor and inhibiting its kinase activity. Alternatively, such an inhibitor can act by occupying the ligand binding site or a portion thereof of the EGF receptor, thereby making the receptor inaccessible to its natural ligand so that its normal biological activity is prevented or reduced. Alternatively, such an inhibitor can act by modulating the dimerization of EGFR polypeptides, or interaction of EGFR polypeptide with other proteins, or enhance ubiquitination and endocytotic degradation of EGFR. EGFR kinase inhibitors include but are not limited to low molecular weight inhibitors, antibodies or antibody fragments, peptide or RNA aptamers, antisense constructs, small inhibitory RNAs (i.e. RNA interference by dsRNA; RNAi), and ribozymes. In a preferred embodiment, the EGFR kinase inhibitor is a small organic molecule or an antibody that binds specifically to the human EGFR.

EGFR kinase inhibitors include, for example quinazoline EGFR kinase inhibitors, pyrido-pyrimidine EGFR kinase inhibitors, pyrimido-pyrimidine EGFR kinase inhibitors, pyrrolo-pyrimidine EGFR kinase inhibitors, pyrazolo-pyrimidine EGFR kinase inhibitors, phenylamino-pyrimidine EGFR kinase inhibitors, oxindole. EGFR kinase inhibitors, indolocarbazole EGFR kinase inhibitors, phthalazine EGFR kinase inhibitors, isoflavone EGFR kinase inhibitors, quinalone EGFR kinase inhibitors, and tyrphostin EGFR kinase inhibitors, such as those described in the following patent publications, and all pharmaceutically acceptable salts and solvates of said EGFR kinase inhibitors: International Patent Publication Nos. WO 96/33980, WO 96/30347, WO 97/30034, WO 97/30044, WO 97/38994, WO 97/49688, WO 98/02434, WO 97/38983, WO 95/19774, WO 95/19970, WO 97/13771, WO 98/02437, WO 98/02438, WO 97/32881, WO 98/33798, WO 97/32880, WO 97/3288, WO 97/02266, WO 97/27199, WO 98/07726, WO 97/34895, WO 96/31510, WO 98/14449, WO 98/14450, WO 98/14451, WO 95/09847, WO 97/19065, WO 98/17662, WO 99/35146, WO 99/35132, WO 99/07701, and WO 92/20642; European Patent Application Nos. EP 520722, EP 566226, EP 787772, EP 837063, and EP 682027; U.S. Pat. Nos. 5,747,498, 5,789,427, 5,650,415, and 5,656,643; and German Patent Application No. DE 19629652. Additional non-limiting examples of low molecular weight EGFR kinase inhibitors include any of the EGFR kinase inhibitors described in Traxler, P., 1998 Exp. Opin. Ther. Patents 8(12):1599-1625.

Specific preferred examples of low molecular weight EGFR kinase inhibitors that can be used according to the present invention include [6,7-bis(2-methoxyethoxy)-4-quinazolin-4-yl]-(3-ethynylphenyl)amine (also known as OSI-774, erlotinib, or TARCEVA®(erlotinib HC1); OSI Pharmaceuticals/Genentech/Roche) (U.S. Pat. No. 5,747,498; International Patent Publication No. WO 01/34574, and Moyer, J. D. et al. (1997) Cancer Res. 57:4838-4848); CI-1033 (formerly known as PD183805; Pfizer) (Sherwood et al., 1999, Proc. Am. Assoc. Cancer Res. 40:723); PD-158780 (Pfizer); AG-1478 (University of California); CGP-59326 (Novartis); PKI-166 (Novartis); EKB-569 (Wyeth); GW-2016 (also known as GW-572016 or lapatinib ditosylate; GSK); and gefitinib (also known as ZD1839 or IRESSA™; Astrazeneca) (Woodburn et al., 1997, Proc. Am. Assoc. Cancer Res. 38:633). A particularly preferred low molecular weight EGFR kinase inhibitor that can be used according to the present invention is [6,7-bis(2-methoxyethoxy)-4-quinazolin-4-yl]-(3-ethynylphenyl)amine (i.e. erlotinib), its hydrochloride salt (i.e. erlotinib HC1, TARCEVA®), or other salt forms (e.g. erlotinib mesylate).

EGFR kinase inhibitors also include, for example multikinase inhibitors that have activity on EGFR kinase, i.e. inhibitors that inhibit EGFR kinase and one or more additional kinases. Examples of such compounds include the EGFR and HER2 inhibitor CI-1033 (formerly known as PD183805; Pfizer); the EGFR and HER2 inhibitor GW-2016 (also known as GW-572016 or lapatinib ditosylate; GSK); the EGFR and JAK 2/3 inhibitor AG490 (a tyrphostin); the EGFR and HER2 inhibitor ARRY-334543 (Array BioPharma); BIBW-2992, an irreversible dual EGFR/HER2 kinase inhibitor (Boehringer Ingelheim Corp.); the EGFR and HER2 inhibitor EKB-569 (Wyeth); the VEGF-R2 and EGFR inhibitor ZD6474 (also known as ZACTIMA™; AstraZeneca Pharmaceuticals), and the EGFR and HER2 inhibitor BMS-599626 (Bristol-Myers Squibb).

Antibody-based EGFR kinase inhibitors include any anti-EGFR antibody or antibody fragment that can partially or completely block EGFR activation by its natural ligand. Non-limiting examples of antibody-based EGFR kinase inhibitors include those described in Modjtahedi, H., et al., 1993Br. J. Cancer 67:247-253; Teramoto, T., et al., 1996, Cancer 77:639-645; Goldstein et al., 1995Clin. Cancer Res. 1:1311-1318; Huang, S. M., et al., 1999, Cancer Res. 15:59(8):1935-40; and Yang, X., et al., 1999, Cancer Res. 59:1236-1243. Thus, the EGFR kinase inhibitor can be the monoclonal antibody Mab E7.6.3 (Yang, X. D. et al. (1999) Cancer Res. 59:1236-43), or Mab C225 (ATCC Accession No. HB-8508), or an antibody or antibody fragment having the binding specificity thereof. Suitable monoclonal antibody EGFR kinase inhibitors include, but are not limited to, IMC-C225 (also known as cetuximab or ERBITUX™; Imclone Systems), ABX-EGF (Abgenix), EMD 72000 (Merck KgaA, Darmstadt), RH3 (York Medical Bioscience Inc.), and MDX-447 (Medarex/Merck KgaA).

EGFR kinase inhibitors for use in the present invention can alternatively be peptide or RNA aptamers. Such aptamers can for example interact with the extracellular or intracellular domains of EGFR to inhibit EGFR kinase activity in cells. An aptamer that interacts with the extracellular domain is preferred as it would not be necessary for such an aptamer to cross the plasma membrane of the target cell. An aptamer could also interact with the ligand for EGFR (e.g. EGF, TGF-α), such that its ability to activate EGFR is inhibited. Methods for selecting an appropriate aptamer are well known in the art. Such methods have been used to select both peptide and RNA aptamers that interact with and inhibit EGFR family members (e.g. see Buerger, C. et al. et al. (2003) J. Biol. Chem. 278: 37610-37621; Chen, C-H. B. et al. (2003) Proc. Natl. Acad. Sci. 100:9226-9231; Buerger, C. and Groner, B. (2003) J. Cancer Res. Clin. Oncol. 129(12):669-675. Epub Sep. 11, 2003).

EGFR kinase inhibitors for use in the present invention can alternatively be based on antisense oligonucleotide constructs. Anti-sense oligonucleotides, including anti-sense RNA molecules and anti-sense DNA molecules, would act to directly block the translation of EGFR mRNA by binding thereto and thus preventing protein translation or increasing mRNA degradation, thus decreasing the level of EGFR kinase protein, and thus activity, in a cell. For example, antisense oligonucleotides of at least about 15 bases and complementary to unique regions of the mRNA transcript sequence encoding EGFR can be synthesized, e.g., by conventional phosphodiester techniques and administered by e.g., intravenous injection or infusion. Methods for using antisense techniques for specifically inhibiting gene expression of genes whose sequence is known are well known in the art (e.g. see U.S. Pat. Nos. 6,566,135; 6,566,131; 6,365,354; 6,410,323; 6,107,091; 6,046,321; and 5,981,732).

Small inhibitory RNAs (siRNAs) can also function as EGFR kinase inhibitors for use in the present invention. EGFR gene expression can be reduced by contacting the tumor, subject or cell with a small double stranded RNA (dsRNA), or a vector or construct causing the production of a small double stranded RNA, such that expression of EGFR is specifically inhibited (i.e. RNA interference or RNAi). Methods for selecting an appropriate dsRNA or dsRNA-encoding vector are well known in the art for genes whose sequence is known (e.g. see Tuschi, T., et al. (1999) Genes Dev. 13(24): 3191-3197; Elbashir, S. M. et al. (2001) Nature 411:494-498; Hannon, G. J. (2002) Nature 418:244-251; McManus, M. T. and Sharp, P. A. (2002) Nature Reviews Genetics 3:737-747; Bremmelkamp, T. R. et al. (2002) Science 296:550-553; U.S. Pat. Nos. 6,573,099 and 6,506,559; and International Patent Publication Nos. WO 01/36646, WO99/32619, and WO 01/68836).

Ribozymes can also function as EGFR kinase inhibitors for use in the present invention. Ribozymes are enzymatic RNA molecules capable of catalyzing the specific cleavage of RNA. The mechanism of ribozyme action involves sequence specific hybridization of the ribozyme molecule to complementary target RNA, followed by endonucleolytic cleavage. Engineered hairpin or hammerhead motif ribozyme molecules that specifically and efficiently catalyze endonucleolytic cleavage of EGFR mRNA sequences are thereby useful within the scope of the present invention. Specific ribozyme cleavage sites within any potential RNA target are initially identified by scanning the target molecule for ribozyme cleavage sites, which typically include the following sequences, GUA, GUU, and GUC. Once identified, short RNA sequences of between about 15 and 20 ribonucleotides corresponding to the region of the target gene containing the cleavage site can be evaluated for predicted structural features, such as secondary structure, that can render the oligonucleotide sequence unsuitable. The suitability of candidate targets can also be evaluated by testing their accessibility to hybridization with complementary oligonucleotides, using, e.g., ribonuclease protection assays.

Both antisense oligonucleotides and ribozymes useful as EGFR kinase inhibitors can be prepared by known methods. These include techniques for chemical synthesis such as, e.g., by solid phase phosphoramadite chemical synthesis. Alternatively, anti-sense RNA molecules can be generated by in vitro or in vivo transcription of DNA sequences encoding the RNA molecule. Such DNA sequences can be incorporated into a wide variety of vectors that incorporate suitable RNA polymerase promoters such as the T7 or SP6 polymerase promoters. Various modifications to the oligonucleotides of the invention can be introduced as a means of increasing intracellular stability and half-life. Possible modifications include but are not limited to the addition of flanking sequences of ribonucleotides or deoxyribonucleotides to the 5' and/or 3' ends of the molecule, or the use of phosphorothioate or 2'-O-methyl rather than phosphodiesterase linkages within the oligonucleotide backbone.

As used herein, the term "IGF-1R kinase inhibitor" refers to any IGF-1R kinase inhibitor that is currently known in the art or that will be identified in the future, and includes any chemical entity that, upon administration to a patient, results in inhibition of a biological activity associated with activation of the IGF-1 receptor in the patient, including any of the downstream biological effects otherwise resulting from the binding to IGF-1R of its natural ligand. Such IGF-1R kinase inhibitors include any agent that can block IGF-1R activation or any of the downstream biological effects of IGF-1R activation that are relevant to treating cancer in a patient. Such an inhibitor can act by binding directly to the intracellular domain of the receptor and inhibiting its kinase activity. Alternatively, such an inhibitor can act by occupying the ligand binding site or a portion thereof of the IGF-1 receptor, thereby making the receptor inaccessible to its natural ligand so that its normal biological activity is prevented or reduced. Alternatively, such an inhibitor can act by modulating the dimerization of IGF-1R polypeptides, or interaction of IGF-1R polypeptide with other proteins, or enhance ubiquitination and endocytotic degradation of IGF-1R. An IGF-1R kinase inhibitor can also act by reducing the amount of IGF-1 available to activate IGF-1R, by for example antagonizing the binding of IGF-1 to its receptor, by reducing the level of IGF-1, or by promoting the association of IGF-1 with proteins other than IGF-1R such as IGF binding proteins (e.g. IGFBP3). IGF-1R kinase inhibitors include but are not limited to low molecular weight inhibitors, antibodies or antibody fragments, antisense constructs, small inhibitory RNAs (i.e. RNA interference by dsRNA; RNAi), and ribozymes. In a preferred embodiment, the IGF-1R kinase inhibitor is a small organic molecule or an antibody that binds specifically to the human IGF-1R.

IGF-1R kinase inhibitors include, for example imidazopyrazine IGF-1R kinase inhibitors, azabicyclic amine inhibitors, quinazoline IGF-1R kinase inhibitors, pyrido-pyrimidine IGF-1R kinase inhibitors, pyrimido-pyrimidine IGF-1R kinase inhibitors, pyrrolo-pyrimidine IGF-1R kinase inhibitors, pyrazolo-pyrimidine IGF-1R kinase inhibitors, phenylamino-pyrimidine IGF-1R kinase inhibitors, oxindole IGF-1R kinase inhibitors, indolocarbazole IGF-1R kinase inhibitors, phthalazine IGF-1R kinase inhibitors, isoflavone IGF-1R kinase inhibitors, quinalone IGF-1R kinase inhibitors, and tyrphostin IGF-1R kinase inhibitors, and all pharmaceutically acceptable salts and solvates of such IGF-1R kinase inhibitors.

Examples of IGF-1R kinase inhibitors include those in International Patent Publication No. WO 05/097800, that describes azabicyclic amine derivatives, International Patent Publication No. WO 05/037836, that describes imidazopyrazine IGF-1R kinase inhibitors, International Patent Publication Nos. WO 03/018021 and WO 03/018022, that describe pyrimidines for treating IGF-1R related disorders, International Patent Publication Nos. WO 02/102804 and WO 02/102805, that describe cyclolignans and cyclolignans as IGF-1R inhibitors, International Patent Publication No. WO 02/092599, that describes pyrrolopyrimidines for the treatment of a disease which responds to an inhibition of the IGF-1R tyrosine kinase, International Patent Publication No. WO 01/72751, that describes pyrrolopyrimidines as tyrosine kinase inhibitors, and in International Patent Publication No. WO 00/71129, that describes pyrrolotriazine inhibitors of kinases, and in International Patent Publication No. WO 97/28161, that describes pyrrolo[2,3-d]pyrimidines and their use as tyrosine kinase inhibitors, Parrizas, et al., which describes tyrphostins with in vitro and in vivo IGF-1R inhibitory activity (Endocrinology, 138:1427-1433 (1997)), International Patent Publication No. WO 00/35455, that describes heteroaryl-aryl ureas as IGF-1R inhibitors, International Patent Publication No. WO 03/048133, that describes pyrimidine derivatives as modulators of IGF-1R, International Patent Publication No. WO 03/024967, WO 03/035614, WO 03/035615, WO 03/035616, and WO 03/035619, that describe chemical compounds with inhibitory effects towards kinase proteins, International Patent Publication No. WO 03/068265, that describes methods and compositions for treating hyperproliferative conditions, International Patent Publication No. WO 00/17203, that describes pyrrolopyrimidines as protein kinase inhibitors, Japanese Patent Publication No. JP 07/133280, that describes a cephem compound, its production and antimicrobial composition, Albert, A. et al., *Journal of the Chemical Society,* 11: 1540-1547 (1970), which describes pteridine studies and pteridines unsubstituted in the 4-position, and A. Albert et al., *Chem. Biol. Pteridines Proc. Int. Symp.,* 4th 4: 1-5 (1969) which describes a synthesis of pteridines (unsubstituted in the 4-position) from pyrazines, via 3-4-dihydropteridines.

Additional, specific examples of IGF-1R kinase inhibitors that can be used according to the present invention include h7C10 (Centre de Recherche Pierre Fabre), an IGF-1 antagonist; EM-164 (ImmunoGen Inc.), an IGF-1R modulator; CP-751871 (Pfizer Inc.), an IGF-1 antagonist; lanreotide (Ipsen), an IGF-1 antagonist; IGF-1R oligonucleotides (Lynx Therapeutics Inc.); IGF-1 oligonucleotides (National Cancer Institute); IGF-1R protein-tyrosine kinase inhibitors in development by Novartis (e.g. NVP-AEW541, Garcia-Echeverria, C. et al. (2004) Cancer Cell 5:231-239; or NVP- ADW742Mitsiades, C. S. et al. (2004) Cancer Cell 5:221-230); IGF-1R protein-tyrosine kinase inhibitors (Ontogen Corp); OSI-906 (OSI Pharmaceuticals); AG-1024 (Camirand, A. et al. (2005) Breast Cancer Research 7:R570-R579 (DOI 10.1186/bcr1028); Camirand, A. and Pollak, M. (2004) Brit. J. Cancer 90:1825-1829; Pfizer Inc.), an IGF-1 antagonist; the tyrphostins AG-538 and I-OMe-AG 538; BMS-536924, a small molecule inhibitor of IGF-1R; PNU-145156E (Pharmnacia & Upjohn SpA), an IGF-1 antagonist; BMS 536924, a dual IGF-1R and IR kinase inhibitor (Bristol-Myers Squibb); AEW541 (Novartis); GSK621659A (Glaxo Smith-Kline); INSM-18 (Insmed); and XL-228 (Exelixis).

Antibody-based IGF-1R kinase inhibitors include any anti-IGF-1R antibody or antibody fragment that can partially or completely block IGF-1R activation by its natural ligand. Antibody-based IGF-1R kinase inhibitors also include any anti-IGF-1 antibody or antibody fragment that can partially or completely block IGF-1R activation. Non-limiting examples of antibody-based IGF-1R kinase inhibitors include those described in Larsson, O. et al (2005) Brit. J. Cancer 92:2097-2101 and Ibrahim, Y. H. and Yee, D. (2005) Clin. Cancer Res. 11:944s-950s; or being developed by Imclone (e.g. IMC-A12), or AMG-479, an anti-IGF-1R antibody (Amgen); R1507, an anti-IGF-1R antibody (Genmab/Roche); AVE-1642, an anti-IGF-1R antibody (Immunogen/Sanofi-Aventis); MK 0646 or h7C10, an anti-IGF-1R antibody (Merck); or antibodies being develop by Schering-Plough Research Institute (e.g. SCH 717454 or 19D12; or as described in US Patent Application Publication Nos. US 2005/0136063 A1 and US 2004/0018191 A1). The IGF-1R kinase inhibitor can be a monoclonal antibody, or an antibody or antibody fragment having the binding specificity thereof.

As used herein, the term "PDGFR kinase inhibitor" refers to any PDGFR kinase inhibitor that is currently known in the art or that will be identified in the future, and includes any chemical entity that, upon administration to a patient, results in inhibition of a biological activity associated with activation of the PDGF receptor in the patient, including any of the downstream biological effects otherwise resulting from the binding to PDGFR of its natural ligand. Such PDGFR kinase inhibitors include any agent that can block PDGFR activation or any of the downstream biological effects of PDGFR activation that are relevant to treating cancer in a patient. Such an inhibitor can act by binding directly to the intracellular domain of the receptor and inhibiting its kinase activity. Alternatively, such an inhibitor can act by occupying the ligand binding site or a portion thereof of the PDGF receptor, thereby making the receptor inaccessible to its natural ligand so that its normal biological activity is prevented or reduced. Alternatively, such an inhibitor can act by modulating the dimerization of PDGFR polypeptides, or interaction of PDGFR polypeptide with other proteins, or enhance ubiquitination and endocytotic degradation of PDGFR. PDGFR kinase inhibitors include but are not limited to low molecular weight inhibitors, antibodies or antibody fragments, antisense constructs, small inhibitory RNAs (i.e. RNA interference by dsRNA; RNAi), and ribozymes. PDGFR kinase inhibitors include anti-PDGF or anti-PDGFR aptamers, anti-PDGF or anti-PDGFR antibodies, or soluble PDGF receptor decoys that prevent binding of a PDGF to its cognate receptor. In a preferred embodiment, the PDGFR kinase inhibitor is a small organic molecule or an antibody that binds specifically to the human PDGFR. The ability of a compound or agent to serve as a PDGFR kinase inhibitor may be determined according to the methods known in art and, further, as set forth in, e.g., Dai et al., (2001) Genes & Dev. 15: 1913-25; Zippel, et al., (1989) Eur. J. Cell Biol. 50(2):428-34; and Zwiller, et al., (1991) Oncogene 6: 219-21.

The invention includes PDGFR kinase inhibitors known in the art as well as those supported below and any and all equivalents that are within the scope of ordinary skill to create. For example, inhibitory antibodies directed against PDGF are known in the art, e.g., those described in U.S. Pat. Nos. 5,976,534, 5,833,986, 5,817,310, 5,882,644, 5,662,904, 5,620,687, 5,468,468, and PCT WO 2003/025019, the contents of which are incorporated by reference in their entirety. In addition, the invention includes N-phenyl-2-pyrimidine-amine derivatives that are PDGFR kinase inhibitors, such as those disclosed in U.S. Pat. No. 5,521,184, as well as WO2003/013541, WO2003/078404, WO2003/099771, WO2003/015282, and WO2004/05282 which are hereby incorporated in their entirety by reference.

Small molecules that block the action of PDGF are known in the art, e.g., those described in U.S. Pat. or Published Application Nos. 6,528,526 (PDGFR tyrosine kinase inhibitors), 6,524,347 (PDGFR tyrosine kinase inhibitors), 6,482,834 (PDGFR tyrosine kinase inhibitors), 6,472,391 (PDGFR tyrosine kinase inhibitors), 6,949,563, 6,696,434, 6,331,555, 6,251,905, 6,245,760, 6,207,667, 5,990,141, 5,700,822, 5,618,837, 5,731,326, and 2005/0154014, and International Published Application Nos. WO 2005/021531, WO 2005/021544, and WO 2005/021537, the contents of which are incorporated by reference in their entirety.

Proteins and polypeptides that block the action of PDGF are known in the art, e.g., those described in U.S. Pat. Nos. 6,350,731 (PDGF peptide analogs), 5,952,304, the contents of which are incorporated by reference in their entirety.

Bis mono- and bicyclic aryl and heteroaryl compounds which inhibit EGF and/or PDGF receptor tyrosine kinase are known in the art, e.g., those described in, e.g. U.S. Pat. Nos. 5,476,851, 5,480,883, 5,656,643, 5,795,889, and 6,057,320, the contents of which are incorporated by reference in their entirety.

Antisense oligonucleotides for the inhibition of PDGF are known in the art, e.g., those described in U.S. Pat. Nos. 5,869,462, and 5,821,234, the contents of each of which are incorporated by reference in their entirety.

Aptamers (also known as nucleic acid ligands) for the inhibition of PDGF are known in the art, e.g., those described in, e.g., U.S. Pat. Nos. 6,582,918, 6,229,002, 6,207,816, 5,668,264, 5,674,685, and 5,723,594, the contents of each of which are incorporated by reference in their entirety.

Other compounds for inhibiting PDGF known in the art include those described in U.S. Pat. Nos. 5,238,950, 5,418,135, 5,674,892, 5,693,610, 5,700,822, 5,700,823, 5,728,726, 5,795,910, 5,817,310, 5,872,218, 5,932,580, 5,932,602, 5,958,959, 5,990,141, 6,358,954, 6,537,988, and 6,673,798, the contents of each of which are incorporated by reference in their entirety.

A number of types of tyrosine kinase inhibitors that are selective for tyrosine kinase receptor enzymes such as PDGFR are known (see, e.g., Spada and Myers ((1995) Exp. Opin. Ther. Patents, 5: 805) and Bridges ((1995) Exp. Opin. Ther. Patents, 5: 1245). Additionally Law and Lydon have summarized the anticancer potential of tyrosine kinase inhibitors ((1996) Emerging Drugs: The Prospect For Improved Medicines, 241-260). For example, U.S. Pat. No. 6,528,526 describes substituted quinoxaline compounds that selectively inhibit platelet-derived growth factor-receptor (PDGFR) tyrosine kinase activity. The known inhibitors of PDGFR tyrosine kinase activity includes quinoline-based inhibitors reported by Maguire et al., ((1994) J. Med. Chem., 37: 2129), and by Dolle, et al., ((1994) J. Med. Chem., 37:

2627). A class of phenylamino-pyrimidine-based inhibitors was recently reported by Traxler, et al., in EP 564409 and by Zimmerman et al., ((1996) *Biorg. Med. Chem. Lett.*, 6: 1221-1226) and by Buchdunger, et al., ((1995) *Proc. Nat. Acad. Sci.* (USA), 92: 2558). Quinazoline derivatives that are useful in inhibiting PDGF receptor tyrosine kinase activity include bismono- and bicyclic aryl compounds and heteroaryl compounds (see, e.g., WO 92/20642), quinoxaline derivatives (see (1994) *Cancer Res.*, 54: 6106-6114), pyrimidine derivatives (Japanese Published Patent Application No. 87834/94) and dimethoxyquinoline derivatives (see *Abstracts of the 116th Annual Meeting of the Pharmaceutical Society of Japan* (Kanazawa), (1996), 2, p. 275, 29(C2) 15-2).

Specific preferred examples of low molecular weight PDGFR kinase inhibitors that can be used according to the present invention include Imatinib (GLEEVEC®; Novartis); SU-12248 (sunitib malate, SUTENT®; Pfizer); Dasatinib (SPRYCEL®; BMS; also known as BMS-354825); Sorafenib (NEXAVAR®; Bayer; also known as Bay-43-9006); AG-13736 (Axitinib; Pfizer); RPR127963 (Sanofi-Aventis); CP-868596 (Pfizer/OSI Pharmaceuticals); MLN-518 (tandutinib; Millennium Pharmaceuticals); AMG-706 (Motesanib; Amgen); ARAVA® (leflunomide; Sanofi-Aventis; also known as SU101), and OSI-930 (OSI Pharmaceuticals); Additional preferred examples of low molecular weight PDGFR kinase inhibitors that are also FGFR kinase inhibitors that can be used according to the present invention include XL-999 (Exelixis); SU6668 (Pfizer); CHIR-258/TKI-258 (Chiron); R04383596 (Hoffmann-La Roche) and BIBF-1120 (Boehringer Ingelheim).

As used herein, the term "FGFR kinase inhibitor" refers to any FGFR kinase inhibitor that is currently known in the art or that will be identified in the future, and includes any chemical entity that, upon administration to a patient, results in inhibition of a biological activity associated with activation of the FGF receptor in the patient, including any of the downstream biological effects otherwise resulting from the binding to FGFR of its natural ligand. Such FGFR kinase inhibitors include any agent that can block FGFR activation or any of the downstream biological effects of FGFR activation that are relevant to treating cancer in a patient. Such an inhibitor can act by binding directly to the intracellular domain of the receptor and inhibiting its kinase activity. Alternatively, such an inhibitor can act by occupying the ligand binding site or a portion thereof of the FGF receptor, thereby making the receptor inaccessible to its natural ligand so that its normal biological activity is prevented or reduced. Alternatively, such an inhibitor can act by modulating the dimerization of FGFR polypeptides, or interaction of FGFR polypeptide with other proteins, or enhance ubiquitination and endocytotic degradation of FGFR. FGFR kinase inhibitors include but are not limited to low molecular weight inhibitors, antibodies or antibody fragments, antisense constructs, small inhibitory RNAs (i.e. RNA interference by dsRNA; RNAi), and ribozymes. FGFR kinase inhibitors include anti-FGF or anti-FGFR aptamers, anti-FGF or anti-FGFR antibodies, or soluble FGFR receptor decoys that prevent binding of a FGFR to its cognate receptor. In a preferred embodiment, the FGFR kinase inhibitor is a small organic molecule or an antibody that binds specifically to the human FGFR. Anti-FGFR antibodies include FR1-H7 (FGFR-1) and FR3-D11 (FGFR-3) (Imclone Systems, Inc.).

FGFR kinase inhibitors also include compounds that inhibit FGFR signal transduction by affecting the ability of heparan sulfate proteoglycans to modulate FGFR activity. Heparan sulfate proteoglycans in the extracellular matrix can mediate the actions of FGF, e.g., protection from proteolysis, localization, storage, and internalization of growth factors (Faham, S. et al. (1998) Curr. Opin. Struct. Biol., 8:578-586), and may serve as low affinity FGF receptors that act to present FGF to its cognate FGFR, and/or to facilitate receptor oligomerization (Galzie, Z. et al. (1997) Biochem. Cell. Biol., 75:669-685).

The invention includes FGFR kinase inhibitors known in the art (e.g. PD173074) as well as those supported below and any and all equivalents that are within the scope of ordinary skill to create.

Examples of chemicals that may antagonize FGF action, and can thus be used as FGFR kinase inhibitors in the methods described herein, include suramin, structural analogs of suramin, pentosan polysulfate, scopolamine, angiostatin, sprouty, estradiol, carboxymethylbenzylamine dextran (CMDB7), suradista, insulin-like growth factor binding protein-3, ethanol, heparin (e.g., 6-O-desulfated heparin), low molecular weight heparin, protamine sulfate, cyclosporin A, or RNA ligands for bFGF.

Other agents or compounds for inhibiting FGFR kinase known in the art include those described in U.S. Pat. Nos. 7,151,176 (Bristol-Myers Squibb Company; Pyrrolotriazine compounds); 7,102,002 (Bristol-Myers Squibb Company; pyrrolotriazine compounds); 5,132,408 (Salk Institute; peptide FGF antagonists); and 5,945,422 (Warner-Lambert Company; 2-amino-substituted pyrido[2,3-d]pyrimidines); U.S. published Patent application Nos. 2005/0256154 (4-amino-thieno[3,2-c]pyridine-7-carboxylic acid amide compounds); and 2004/0204427 (pyrimidino compounds); and published International Patent Applications WO-2007019884 (Merck Patent GmbH; N-(3-pyrazolyl)-N'-4-(4-pyridinyloxy)phenyl)urea compounds); WO-2007009773 (Novartis AG; pyrazolo[1,5-a]pyrimidin-7-ylamine derivatives); WO-2007014123 (Five Prime Therapeutics, Inc.; FGFR fusion proteins); WO-2006134989 (Kyowa Hakko Kogyo Co., Ltd.; nitrogenous heterocycle compounds); WO-2006112479 (Kyowa Hakko Kogyo Co., Ltd.; azaheterocycles); WO-2006108482 (Merck Patent GmbH; 9-(4-ureidophenyl)purine compounds); WO-2006105844 (Merck Patent GmbH; N-(3-pyrazolyl)-N'-4-(4-pyridinyloxy)phenyl)urea compounds); WO-2006094600 (Merck Patent GmbH; tetrahydropyrroloquinoline derivatives); WO-2006050800 (Merck Patent GmbH; N,N'-diarylurea derivatives); WO-2006050779 (Merck Patent GmbH; N,N'-diarylurea derivatives); WO-2006042599 (Merck Patent GmbH; phenylurea derivatives); WO-2005066211 (Five Prime Therapeutics, Inc.; anti-FGFR antibodies); WO-2005054246 (Merck Patent GmbH; heterocyclyl amines); WO-2005028448 (Merck Patent GmbH; 2-amino-1-benzyl-substituted benzimidazole derivatives); WO-2005011597 (Irm L1c; substituted heterocyclic derivatives); WO-2004093812 (Irm L1c/Scripps; 6-phenyl-7H-pyrrolo[2,3-d]pyrimidine derivatives); WO-2004046152 (F. Hoffmann La Roche AG; pyrimido[4,5-e]oxadiazine derivatives); WO-2004041822 (F. Hoffmann La Roche AG; pyrimido[4,5-d]pyrimidine derivatives); WO-2004018472 (F. Hoffmann La Roche AG; pyrimido[4,5-d]pyrimidine derivatives); WO-2004013145 (Bristol-Myers Squibb Company; pyrrolotriazine derivatives); WO-2004009784 (Bristol-Myers Squibb Company; pyrrolo[2,1-f][1,2,4]triazin-6-yl compounds); WO-2004009601 (Bristol-Myers Squibb Company; azaindole compounds); WO-2004001059 (Bristol-Myers Squibb Company; heterocyclic derivatives); WO-02102972 (Prochon Biotech Ltd./Morphosys AG; anti-FGFR antibodies); WO-02102973 (Prochon Biotech Ltd.; anti-FGFR antibodies); WO-00212238 (Warner-Lambert Company; 2-(pyridin-4-ylamino)-6-dialkoxyphenyl-pyrido

[2,3-d]pyrimidin-7-one derivatives); WO-00170977 (Amgen, Inc.; FGFR-L and derivatives); WO-00132653 (Cephalon, Inc.; pyrazolone derivatives); WO-00046380 (Chiron Corporation; FGFR-Ig fusion proteins); and WO-00015781 (Eli Lilly; polypeptides related to the human SPROUTY-1 protein).

Specific preferred examples of low molecular weight FGFR kinase inhibitors that can be used according to the present invention include RO-4396686 (Hoffmann-La Roche); CHIR-258 (Chiron; also known as TKI-258); PD 173074 (Pfizer); PD 166866 (Pfizer); ENK-834 and ENK-835 (both Enkam Pharmaceuticals A/S); and SU5402 (Pfizer). Additional preferred examples of low molecular weight FGFR kinase inhibitors that are also PDGFR kinase inhibitors that can be used according to the present invention include XL-999 (Exelixis); SU6668 (Pfizer); CHIR-258/TKI-258 (Chiron); RO4383596 (Hoffmann-La Roche), and BIBF-1120 (Boehringer Ingelheim).

The present invention also provides a method of identifying an agent that inhibits epithelial cells from undergoing an epithelial to mesenchymal transition, comprising contacting a sample of cells of the epithelial cell line H358 with a test agent to be screened, contacting the sample with a single or dual protein ligand preparation that induces an epithelial-to-mesenchymal transition in H358 cells, determining whether the test agent inhibits the epithelial cells in the sample from undergoing an epithelial to mesenchymal transition, by comparing the level of a biomarker whose level is indicative of the EMT status of the sample cells to the level of the same biomarker in an identical sample of H358 cells not contacted with the test agent, and thus determining whether the test agent is an agent that inhibits cells from undergoing an epithelial to mesenchymal transition. Agents that inhibit epithelial cells from undergoing an epithelial to mesenchymal transition are useful for the treatment of fibrotic disorders resulting in part from EMT transitions, including but not limited to renal fibrosis, hepatic fibrosis, pulmonary fibrosis, and mesotheliomas. In one embodiment, the single protein ligand that induces an epithelial-to-mesenchymal transition in H358 cells is selected from EGF; TGFbeta; TNFalpha; and IL-4. In another embodiment, the dual protein ligands that induce an epithelial-to-mesenchymal transition in H358 cells are oncostatin-M plus HGF.

The present invention also provides a method of identifying an agent that inhibits cells that have undergone an epithelial to mesenchymal transition, comprising contacting a sample of cells of the epithelial cell line H358 with a single or dual protein ligand preparation to induce an epithelial-to-mesenchymal transition in the H358 cells, contacting the sample of cells with a test agent to be screened, determining whether the test agent inhibits mesenchymal-like H358 cell growth, and thus determining whether it is an agent that inhibits the growth of cells that have undergone an epithelial to mesenchymal transition. Agents that inhibit mesenchymal-like cells are useful for the treatment of fibrotic disorders resulting in part from EMT transitions, including but not limited to renal fibrosis, hepatic fibrosis, pulmonary fibrosis, and mesotheliomas. In one embodiment, the single protein ligand that induces an epithelial-to-mesenchymal transition in H358 cells is selected from EGF; TGFbeta; TNFalpha; and IL-4. In another embodiment, the dual protein ligands that induce an epithelial-to-mesenchymal transition in H358 cells are oncostatin-M plus HGF. An alternative embodiment of this method comprises, after the step of determining whether the test agent inhibits the growth of cells that have undergone an epithelial to mesenchymal transition, the additional steps of determining whether an agent that inhibits mesenchymal-like H358 tumor cell growth, also inhibits epithelial H358 tumor cell growth, and thus determining whether it is an agent that specifically inhibits the growth of cells that have undergone an epithelial to mesenchymal transition. In an embodiment of the above methods, an agent that inhibits the growth of cells that have undergone an epithelial to mesenchymal transition is determined to do so by stimulating apoptosis of said cells. In another embodiment of the above methods, an agent that inhibits the growth of cells that have undergone an epithelial to mesenchymal transition is determined to do so by inhibiting proliferation of said cells.

The present invention also provides a method of identifying an agent that stimulates mesenchymal-like cells to undergo a mesenchymal to epithelial transition, comprising contacting a sample of cells of the epithelial cell line H358 with a single or dual protein ligand preparation to induce an epithelial-to-mesenchymal transition in the H358 cells, contacting the sample of cells with a test agent to be screened, determining whether the test agent stimulates the mesenchymal-like H358 cells in the sample to undergo a mesenchymal to epithelial transition, by comparing the level of a biomarker whose level is indicative of the EMT status of the sample cells to the level of the same biomarker in an identical sample of mesenchymal-like H358 cells not contacted with the test agent, and thus determining whether the test agent is an agent that stimulates mesenchymal-like cells to undergo a mesenchymal to epithelial transition. Agents that stimulate mesenchymal-like cells to undergo a mesenchymal to epithelial transition are useful for the treatment of fibrotic disorders resulting in part from EMT transitions, including but not limited to renal fibrosis, hepatic fibrosis, pulmonary fibrosis, and mesotheliomas. In one embodiment, the single protein ligand that induces an epithelial-to-mesenchymal transition in H358 cells is selected from EGF; TGFbeta; TNFalpha; and IL-4. In another embodiment, the dual protein ligands that induce an epithelial-to-mesenchymal transition in H358 cells are oncostatin-M plus HGF.

The present invention also provides a method of identifying an agent that inhibits cells from undergoing an epithelial to mesenchymal transition, comprising contacting a sample of cells of the epithelial cell line H358, which have been engineered to inducibly express a protein that stimulates an epithelial to mesenchymal transition in H358 cells, with a test agent to be screened, contacting the sample with a compound that induces the expression of said protein that stimulates an epithelial to mesenchymal transition in the engineered H358 cells, determining whether the test agent inhibits the cells in the sample from undergoing an epithelial to mesenchymal transition, by comparing the level of a biomarker whose level is indicative of the EMT status of the sample cells to the level of the same biomarker in an identical sample of engineered H358 cells not contacted with the test agent, and thus determining whether the test agent is an agent that inhibits cells from undergoing an epithelial to mesenchymal transition.

The present invention also provides a method of identifying an agent that inhibits cells that have undergone an epithelial to mesenchymal transition, comprising: contacting a sample of cells of the epithelial cell line H358, which have been engineered to inducibly express a protein that stimulates an epithelial to mesenchymal transition in H358 cells, with a compound that induces the expression of said protein such that an epithelial-to-mesenchymal transition is induced in the cells, contacting the sample of cells with a test agent to be screened, determining whether the test agent inhibits mesenchymal-like H358 cell growth, and thus determining whether it is an agent that inhibits the growth of cells that have undergone an epithelial to mesenchymal transition. An alternative embodiment of this method comprises, after the step of determining whether the test agent inhibits the growth of cells that have undergone an epithelial to mesenchymal transition, the additional steps of determining whether an agent that inhibits mesenchymal-like H358 cell growth, also inhibits epithelial H358 cell growth, and thus determining whether it is an agent that specifically inhibits the growth of cells that have undergone an epithelial to mesenchymal transition. In an embodiment of the above methods, an agent that inhibits the growth of cells that have undergone an epithelial to mesenchymal transition is determined to do so by stimulating apoptosis of said cells. In another embodiment of the above methods, an agent that inhibits the growth of cells that have undergone an epithelial to mesenchymal transition is determined to do so by inhibiting proliferation of said cells.

The present invention also provides a method of identifying an agent that stimulates mesenchymal-like cells to undergo a mesenchymal to epithelial transition, comprising contacting a sample of cells of the epithelial cell line H358, which have been engineered to inducibly express a protein that stimulates an epithelial to mesenchymal transition in H358 cells, with a compound that induces the expression of said protein such that an epithelial-to-mesenchymal transition is induced in the cells, contacting the sample of cells with a test agent to be screened, determining whether the test agent stimulates the mesenchymal-like H358 cells in the sample to undergo a mesenchymal to epithelial transition, by comparing the level of a biomarker whose level is indicative of the EMT status of the sample cells to the level of the same biomarker in an identical sample of mesenchymal-like H358 cells not contacted with the test agent, and thus determining whether the test agent is an agent that stimulates mesenchymal-like cells to undergo a mesenchymal to epithelial transition.

This invention will be better understood from the Experimental Details that follow. However, one skilled in the art will readily appreciate that the specific methods and results discussed are merely illustrative of the invention as described more fully in the claims which follow thereafter, and are not to be considered in any way limited thereto.

Experimental Details:

Introduction

Models for the identification of targeted anti-cancer agents and the rational design of specific combinations of anti-cancer agents are clearly needed to advance such agents to clinical testing. Here we describe model systems for both epithelial and mesenchymal tumor cell components. The ability to target both epithelial and mesenchymal cell types within tumors will be critical to a therapeutic impact on long term patient survival. The models described enable evaluation of anti-cancer compounds, antibodies, aptamers and other therapeutic nucleic acids toward the tumors cell types in vitro and in animal models.

Materials and Methods

Cell Culture Conditions

The human line H358 was cultured in the appropriate ATCC recommended supplemented media. Growth factor and cytokine induced EMT was monitored over a 7-14 day period. Growth factors and cytokines were obtained from commercial sources and included TGFβ 10 ng/ml, Endothelin 100 nM, IL-4 5 ng/ml, IL-6 5 ng/ml, IL-8 5 ng/ml, VEGF 10 ng/ml, Stromal derived factor, 100 ng/ml, Epidermal derived factor 10 ng/ml, MMP2, 100 ng/ml, MMP7, 100 ng/ml, MMP9, 100 ng/ml, Collagen-I, 5 μg/cm2, Collagen-IV, 5 μg/cm2, Fibronectin, 1 μg/cm2, Laminin-I, 1 μg/cm2, Vitronectin, 0.1 μg/cm2, Polylysine, 100 mg/mL, HGF, 100 ng/mL, MSP, 100 ng/ml, IGF-1, 50 ng/mL, CSF-1, 100 ng/mL, ET1, 100 nM, SDF-1alpha, 100 ng/ml PGE2, 500 nM, LPA, 10 μM, S1P, 1 μM, TGFbeta1, 2.5 ng/mL, TNFalpha, 25 ng/mL, IL1beta, 2.5 ng/mL, IL6, 2 ng/mL, IL8, 0.5 ng/mL, WNT-1, 5 ng/mL, CTGF, 20 ng/ml, Trance, 50 ng/ml, FGF1, 10 ng/ml, FGF2, 10 ng/ml, BMP4, 100 ng/ml, BMP7, 100 ng/ml, IGF2, 100 ng/ml, Oncostatin M, 100 ng/ml, NRG1, 50 ng/ml, PDGF-AA, 50 ng/ml, PDGF-BB, 30 ng/ml, WISP1, 20 ng/ml, Fulvestrant, 1 μM, LIF, 20 ng/ml, IFN g, 50 ng/ml, HMG-B1, 50 ng/ml, M-CSF, 50 ng/ml, PTHrP, 50 ng/ml, MCP1, 50 ng/ml, IL-1a, 10 ng/ml, IL-33, 50 ng/ml, IL-31, 50 ng/ml, GM-CSF, 25 ng/ml, Angiopoeitin 2, 400 ng/ml, PAR1, 100 μM, PAR2, 100 μM, PAR4, 100 μM, Wnt5a, 200 ng/ml, G-CSF, 50 ng/ml, Amphiregulin, 100 ng/ml, CNTF, 25 ng/mL, Pleiotrophin, 25 ng/ml, Prolactin, 100 ng/ml, TRAIL, 100 ng/ml.

Pharmacological Inhibitors

MEK inhibitor 1 ("MEKi"; EMD Biosciences #444937), JAK inhibitor 1 ("JAKi"; EMD Biosciences #420099), and LY294002 (PI3K inhibitor (PI3Ki); EMD Biosciences #440202) were used in the concentrations indicated. Cells were treated with inhibitor 30 minutes prior to ligand stimulation. Medium, inhibitor and ligand were refreshed on experimental day 3 to 4.

3-Dimensional matrigel culture: Tissue culture wells were coated with a layer of matrigel of 1 mm depth or greater. H358 cells were plated on top of this in 2% matrigel with seeding density of 2,500-5000 cells/cm$^2$. Once the cell/matrigel layer had solidified, media was added and cultures were allowed to incubate overnight at 37° C. in a CO$_2$ incubator before treatment of cells with ligand with and without addition of 10 μM SB431542 (Sigma-Aldrich, St. Louis, Mo.; product #S4317). Culture media, ligand with and without addition of 10 μM SB431542 was replenished every 3-4 days during the duration of the experiment.

Immunoblot Analysis of Cell Line Extracts

Cell lines were treated as indicated in the text and figure legends. Cell lysates were prepared in RIPA buffer (Sigma, #R0278) containing protease (Sigma #P8340) and phosphatase (Sigma, #P5726) inhibitors. Protein concentration was determined by micro-BCA assay (Pierce, #23227). Protein immunodetection was performed by electrophoretic transfer of SDS-PAGE separated proteins to nitrocellulose, incubation with antibody and chemiluminescent second step detection (PicoWest; Pierce, #34078). The antibodies used were: E-cadherin (sc21791), N-cadherin (#7939), ErbB3 (sc285), GAPDH (#25778) and Zeb1 (#25388), all from Santa Cruz Biotechnology; vimentin (BD550513) and fibronectin (BD610077; both from BD Biosciences); β-actin (Sigma, #A5441).

Generation of TET-Responsive Cell Lines

H358 cells were seeded in 90 mm TC dish at a density to ensure 80% confluence after 24 hours of growth. The plasmids ptTS and prTA were transected into the cells at a 10:1 ratio using Fugene HD transfection-reagent (Fugene). After 4 hours the media was removed and replaced with normal growth media and the cells allowed to grow for a further 48 hours. The cells were then split at different ratios (1:25, 1:50 and 1:100) into 150 mm TC dishes and allowed to grow for 24 hours. Drug (blasticidin, 100 μg/ml) was then added to the media and cell colonies selected over a 3-4 week period with the Bsd concentration being gradually reduced to 10 ug/ml. Colonies arising from single cells were picked from the plates using cell colony filters and expanded. The clones were screened for those which showed a tightly regulated inducible expression of a transiently introduced TET-responsive luciferase expression plasmid, as assayed by a luciferase assay (Steady Glo, Promega). A >10 fold induction of luciferase expression in response to doxycycline expression was considered adequate for further cell line construction.

Generation of TET-Inducible Target Gene Cell Lines

Plasmids containing full length cDNAs encoding Snail, Zeb1, or TGFbeta (constitutively active) (Snail mRNA sequence, Genbank NM_005985, product of GeneID: 6615; Zeb1 mRNA sequence, Genbank NM_030751, product of GeneID: 6935; TGFbeta sequence encoding constitutively active Ser223/S225 human TGF-beta-1 (i.e. Genbank NP_000651 (product of GeneID: 7040), with cysteines 223 and 225 mutated to serine) under the control of a Tet-regulated promoter (pTRE2; Invitrogen) were constructed using standard methods. The TET-ON cell lines were plated and transfected with a pTRE2-Snail, pTRE2-Zeb1, or pTRE2-TGFbeta plasmid as described above. Once plated into 150 mm dishes the single cells were selected using puromycin (0.5 µg/ml). Colonies were selected over a 3-4 weeks period with puromycin concentration being reduced to a final concentration of 0.1 µg/ml. Colonies were picked using colony filters and screened for TET-dependent expression of the target gene by western blot analysis. In some cases multiple cDNAs were cotransfected into a given cell line. These methods enable the generation of cell lines which undergo EMT in response to tetracycline or analogs thereof, driven by the cDNAs listed above.

Measurement of Cell Proliferation: Cell proliferation was determined using the Cell Titer Glo assay (Promega Corporation, Madison, Wis.). Cell lines were seeded at a density of 3000 cells per well in a 96-well plate. 24 hours after plating cells were dosed with varying concentrations of drug, either as a single agent or in combination. The signal for Cell Titer Glo was determined 72 hours after dosing.

Measurement of apoptosis: Induction of apoptosis as measured by increased Caspase 3/7 activity was determined using the CASPASE-GLO® 3/7 assay (Promega Corporation, Madison, Wis.). Cell lines were seeded at a density of 3000 cells per well in a 96-well plate. 24 hours after plating cells were dosed with varying concentrations of drug, either as a single agent or in combination. The signal for CASPASE-GLO®3/7 was determined 24 hours after dosing. The caspase 3/7 activity was normalized to cell number per well, using a parallel plate treated with Cell Titer Glo (Promega Corporation, Madison, Wis.). Signal for each well was normalized using the following formula: CASPASE-GLO®3/7 luminescence units/Cell Titer Glo fraction of DMSO control. All graphs were generated using PRISM® software (Graphed Software, San Diego, Calif.).

Immunofluorescence and Confocal Microscopy

Cells were plated on coverslips on experimental day 0, stimulated with ligand on day 1 and refreshed with medium and ligand on day 3-4. On day 7, cells were fixed at room temperature for 10 minutes in 4% paraformaldehyde (EMS #15701)/PBS (Gibco #14190). Cells were blocked in 3% BSA/PBS and incubated with primary antibody (E-cadherin, Santa Cruz #sc21791 and Vimentin, Chemicon #AB5733) diluted in blocking buffer for two hours at room temperature. Cells were washed and incubated in secondary antibody (Invitrogen #A11029 and Chemicon #AP194R) followed by nuclear counterstain TO-PRO3 (Invitrogen #T3605). Coverslips were mounted on slides with Pro-Long Gold anti-fade reagent (Invitrogen P36934). Images were captured on a Leica DMRXE microcope with SP2 scanner using Leica Confocal Software.

Measurement of Cell Migration and Invasion

Cells treated with ligand for 6 days were serum-starved overnight with ligand. The following day, assays were performed in modified Boyden chambers (Trevigen Cultrex #3458-096-K) with cells in serum-free medium in the upper chamber. Serum with 10% FBS±3× concentration of ligand was used in the lower chamber as chemo-attractant. Migration was measured using uncoated membranes and quantified after 24 hours following manufacturer's instructions. Invasion was measured with Collagen IV-coated membranes and quantified after 48 hours.

Reversion of EMT Morphology and Phenotype

Cells were treated with or without ligand for 7 days, then passaged to fresh plates without ligand. Cells were harvested for protein on the indicated days and immunoblotted for EMT markers to monitor reversion. For migration and invasion assays, cells were allowed to revert for 14 days with the last day being under serum-free conditions. The assays were then performed as described above.

Additional Materials and Methods for H358 HGF OSM EMT Model Microarray and Proteomic Profiling Cell Culture and Treatments:

H358 cells were grown in RPMI 1650 medium (Gibco #21870) supplemented with 10% fetal bovine serum (Sigma), 2 mM L-Glutamate (Gibco), 1 mM sodium pyruvate (Gibco) and 0.1 mM HEPES. Cells were grown at 37° C. with 5% $CO_2$. Cells were seeded on experimental day 0, stimulated with ligand on day 1 in complete medium and allowed to grow for 7 days. Ligand and medium were replenished on experimental days 3 and 6. HGF (Peprotech #100-39) and OSM (R&D Systems #295-OM) were both used at 100 ng/ml.

Affymetrix Arrays:

On experimental day 7, the cells were trypsinized, washed, pelleted, and snap frozen. Cell pellets were sent to Genome Explorations for mRNA isolation and analysis by Affymetrix Human Genome 133 Plus 2.0 Array.

Proteomics:

On experimental day 7, cells were harvested for protein. For analysis of total protein, nuclear, membrane and cytosol fractions were prepared using PROTEOEXTRACT® reagent (EMD #444810). Proteins were then precipitated using trichloroacetic acid/deoxycholate co-precipitation. 2% deoxycholate was added to samples and incubated for 30 min on ice. 100% TCA was then added to samples in a 1:1 ratio (vol/vol). Samples were vortexed and incubated overnight (10° C.), then centrifuged at 15,000×g for 10 minutes (4° C.). The precipitate was washed with 5 ml cold acetone, vortexed, reprecipitated twice and air dried. Precipitated samples were resuspended in 8 M urea, reduced with 5 mM tributylphosphine (Sigma-Aldrich #T7567; 1 hour at RT), alkylated with iodoacetamide (15 mM for 1.5 hours at RT), diluted to 1 M urea and subject to proteolysis with 20 ug trypsin (Sigma-Aldrich #T6567; 37oC, 18 hours). Peptides were acidified with trifluoroacetic acid (TFA) and desalted using C18 Sep-Pak Plus Cartridges (Waters Corp. #WAT020515). Protein concentration was determined using bicinchoninic acid (MICROBCA™, Pierce). Anti-phosphotyrosine affinity selection was performed as previously described (Thelemann et al; Petti et al).

Peptide Identification and Quantification by Stable Isotope Labeling and Liquid Chromatography-Electrospray Ionization Tandem Mass Spectrometry.

Protein reduction, alkylation, trypsin digestion and stable isotope labeling were performed as previously described {Petti, 2005 #95; Ross, 2004 #94} using a different isobaric tag to label peptides following stimulation. Both 4plex (Ross, 2004) and 8plex iTRAQ strategies were used. After labeling, the peptides were further purified by cation exchange chromatography and C18 desalting steps. Strong cation exchange (SCX) chromatography was performed using a 4.6×5 mm cation exchange cartridge packed with polysulfoethyl A resin (OptimizeTechnologies, Oregon City, Oreg.). Peptides were desalted prior to on-line LC-MS/MS by gradient C18 reverse phase chromatography (3×5 mm trap #11-02872-TA; Optimize Technologies) in 0.1% TFA, 4-60% acetonitrile over 5 minutes with UV detection at 214 nm. An 8plex iTRAQ labeling strategy with MSMS tags of m/z 113, 114, 115, 116, 117, 118, 119, 121 (Applied Biosystems, Foster City, Calif.) used LC-MS/MS conditions were identical to those described above for 4plex samples.

Peptide masses, peptide sequence information and peptide quantitation were obtained by liquid chromatography-electrospray ionization tandem mass spectrometry (LC-MS/MS) and protein database searching {Petti, 2005 #95}. Peptides were introduced into the quadrupole time of flight mass spectrometer by reverse-phase (C18) HPLC. C18 columns were self-packed 75ux~10 cm (3 u MagicC18; Michrom Bioresources, Auburn, Calif.) in PicoFrit (New Objective, Cambridge, Mass.) fritted fused silica tubing (15 u ID), developed by gradient elution with acetonitrile, 0.1% formic acid (0.39%/min) at 200 nl/minute using a spray voltage of ~2.7 kV. Information-dependent MS and MS-MS acquisitions were made on an orthogonal quadrapole-TOF (Qq-TOF) instrument (SCIEX, Toronto, Canada) using a 0.3 second survey scan (m/z 400-1600) followed typically by 3 consecutive second product ion scans of 0.5 seconds each (m/z 60-1200). Parent ion with charge states of 2+, 3+ and 4+ were selected with a 2 minute exclusion period. Ions were stored in the second quadrupole and released in synchrony with the 'pulsing' of ions in time-of-flight (TOF) detector. MS data was collected using Analyst QS (Version:1.1; Applied Biosystems Inc., Foster City, Calif.). Eightfold data binning was used. Proteins were identified at >95% confidence from survey and product ion spectra data, searching human sequences within the UniProt protein database (releases from October 2005 to January 2007) using the Paragon algorithm of ProteinPilot (Version 2.0; Builds 44649beta and 50861; Applied Biosystems/MDS Sciex). When multiple isoforms were detected, only peptides specific to each detected form were used, which factored in ion counts for weighting in the protein ratio calculation {Shilov, 2007 #101}. Protein identification complied with the guidelines of {Bradshaw, 2006 #99} where 2 or more unique isoform-specific peptides were required for inclusion. Parsimony of protein results was assured by rigorous protein inference with the ProGroup algorithm. Proteins identified with ≧95% confidence with relative abundances between cell or cell states in the upper and lower distribution quartiles (>75% or <25%) with a t-test p value (for any difference between cell line or biological condition) of <0.05 were further considered. Proteins with relative abundances between cell or cell states in the upper and lower distribution quartiles (>75% or <25%) was used to correctly bin previously defined benchmark proteins, E-cadherin, α catenin, β catenin and vimentin {Thomson, 2005 #44}, to epithelial and mesenchymal cell states. It should be noted that similar to DNA microarray studies, data compression underestimates changes in protein abundance, when compared with ELISA or immunoblot approaches. In DNA array studies this is due to 'on spot' hybridization noise, while in mammalian cell fractionation experiments this is due to MS/MS noise associated with complex peptide mixtures.

Additional Materials and Methods for H358 in Vivo Studies.

To better understand the role of EMT in cancer progression and drug resistance in vivo, three doxycycline inducible cell lines were created to express either an activated form of TGFβ (tet-on TGFβ), Zeb1 (tet-on Zeb1), or Snail (tet-on Snail) in the epithelial-like H358 NSCLC cell line. These stable cell lines were also luciferase labeled using lentivirus for use in vivo studies. These inducible cell lines undergo an EMT-like transition in vitro. These models were characterized in vivo by evaluating the ability of these genes to cause an EMT-like transition in subcutaneous xenografts. To induce the tet-responsive gene, the mice were offered drinking water with 0.5 mg/ml doxycycline, and the tumors allowed to grow. At selected time points, the mice were sacrificed and the tumors excised. Tumors were fixed for immuno-histochemical analysis and tumor lysates were made for western blotting analysis to examine changes in the hallmark EMT markers E-cadherin and vimentin. Additionally, tumor growth was monitored and pathological changes were noted where applicable.

Imaging of Epithelial-Mesenchymal Transition in Vivo.

Luciferase expressing tumor cells may be monitored in mice implanted with such cells. Tet-inducible lines were transfected with CMV-luciferase to monitor tumor size and metastasis in flank and orthotopic xenograft tumor models. Alternatively the epithelial gene promoter sequences upstream of the human E-cadherin gene (Genbank Corenucleotide Locus DQ335132, human E-cadherin gene, promoter and 5' UTR, 1112 bp DNA; Liu, Y—N. et al. (2005) Oncogene 24:8277-8290) were linked 5' to the luciferase gene and transfected into the Tet-inducible cell lines so as to monitor tumor cells in the epithelial state in vivo. Similarly the mesenchymal gene promoter sequences upstream of the human vimentin gene (bases 2347 to 3952 (promoter sequence) of Genbank Corenucleotide Locus EF445046, human vimentin gene with total 15123 bp DNA) were linked 5' to the luciferase gene and transfected into the Tet-inducible cell lines so as to monitor tumor cells in the mesenchymal state in vivo. Multiple epithelial and mesenchymal promoter sequences can be used.

Because non-invasive bioluminescent imaging permits repetitive measurements of the same animal over time (longitudinal studies), it offers the ability to observe and measure dynamic biological processes without interfering with those processes. Non-invasive bioluminescent imaging allows multiple analyses of several components of cancer: 1) location, 2) size, 3) time, and 4) type, or state of disease. These components, when integrated, allow a reasonable interpretation of the dynamic process of tumor development and/or progression. In order to visualize and track cancer cells in vivo, the cells need to first be engineered to express a bioloumuninescent reporter gene that allows the emission of light in the presence of a substrate such as the luciferin catalyzing enzyme from *Photinus pyralis*; commonly known as Firefly Luciferase. To accomplish this, the H358 engineered cell lines were transduced with lentivirus containing Firefly Luciferase driven by the hEF1α/HTLV promoter (cat# LV 198, Lentigen). A pooled population of cells for each cell line was made by transducing $1*10^6$ cells with $1"10e^7$ lentivirus particles in the presence of 6 ng/ml Polybrene in normal growth media overnight. After validation of bioluminescent activity in vitro, these cell lines were propagated as a stable cell line, and implanted into nude mice either subcutaneously or orthotopically into the appropriate local, where they were readily imaged using the Xenogen IVIS® Spectrum system (FIG. 15). In the case of studies pertaining to EMT, cells engineered to undergo EMT in vivo can be tracked repeatedly over time to determine tumor growth, locale, spread, and metastatic ability. In addition, monitoring bioluminescence serves as a normalizing factor for tumor cell quantity when using various in vivo assays.

Western Blotting of Induced Tumors

Doxycycline is added to the drinking water to induce gene induction and concomitant EMT marker changes in subcutaneous tumors of H358 tet-inducible EMT models in SCID mice. The subcutaneous tumors were removed after 7 days of doxycyline administration and flash frozen in liquid nitrogen. Tumors were homogenized in RIPA buffer containing protease and phosphatase inhibitors using a bead homogenizer. The lysates were analyzed using standard western blotting techniques. The blots were incubated with primary antibody overnight and detected using chemiluminescence in the presence of secondary HRP conjugated antibodies (Cell Signaling Technologies cat #7074,7076; Amersham ECL Plus cat# RPN1232). The following primary antibodies were used for protein detection: E-cadherin-Cell Signaling Technologies catalogue #4605, 1:1000; vimentin-BD Pharmingen cat #550513, 1:5000; TGFβ-Cell Signaling Technologies cat#3709, 1:1000; Snail-AbCam cat#17732, 1:1000; Zeb1-Santa Cruz cat#10570, 1:1000. The slides were examined by a pathologist and notable changes reported. The slides were scanned using the Aperio SCANSCOPE® and pictures acquired using the Aperio ImageScan software.

Immunohistochemistry of Induced Tumors

Doxycycline is added to the drinking water to induce gene induction and concomitant EMT marker changes in the tumors of H358 tet-inducible EMT models in SCID mice. Subcutaneous tumors were removed after 7 days of doxycyline administration and fixed in neutral-buffered formalin. After fixation, the tissues were embedded in paraffin and cut into 8 μm sections. For immunohistochemical staining, the common practice of citrate buffer antigen retrieval was utilized, followed by primary antibody incubation, detected with HRP-conjugated secondary antibody with 3'-diaminobenzidine (DAB) substrate, and hematoxylin counterstain. The primary antibodies that were used for protein detection were: E-cadherin-Cell Signaling Technologies catalogue #4605, 1:50; vimentin-Chemicon/Millipore cat #AB5733, 1:6400; Snail-Santa Cruz cat #10433, 1:400; Zeb1-Santa Cruz cat #10570, 1:50.

Growth of Induced Tumors

SCID mice were implanted with $1*10^7$ H358 tet-on (with gene of interest) cells mixed 1:1 with Matrigel (BD Pharmingen). Doxycycline (0.5 mg/ml in drinking water) was administered at the time of implantation, and tumor growth was followed for 21 days and tumor volume recorded using caliper measurements. The mean and standard deviation for each group (n=8 each group) are reported.

Results

EMT Ligand Driven Cell Models

The ability of cell lines to undergo epithelial to mesenchymal transition (EMT) was investigated using different extracellular ligand drivers. Five NSCLC cell lines, including H358, were treated with individual growth factors and cytokines to assess their capacity to induce an EMT-like transition. Only H358 (FIG. 1) was capable of a full transition (i.e. the loss of epithelial markers, for example E-cadherin or ErbB3, and the gain of mesenchymal markers, for example vimentin, fibronectin and/or Zeb1). These growth factors and cytokines were chosen to mimic the inflammatory stimuli thought to promote tumor cell EMT in vivo.

The following conclusions were made. TGFβ induces the most complete EMT in H358 cells, not observed in other NSCLC lines. Partial EMT was observed in some other cell lines treated with TGFβ. TNFα also was able to induce EMT in H358 cells. EGF and IL-4 induced EMT to a lesser extent.

A panel of NSCLC cell lines was screened by treatment of cells for 7 days in presence of respective ligands, either singly or in combination. Initial screening determined the ability of the ligand to cause morphology change, to down-regulate the epithelial marker, E-cadherin or to up-regulate a mesenchymal marker such as vimentin. Potential EMT cell models should up-regulate a mesenchymal marker and display morphology change. More robust models would show a down-regulation of E-cadherin expression. For those models where protein levels of E-cadherin were not substantially down-regulated, it is postulated that the E-cadherin is mislocalized.

The NSCLC cell line H358 was shown to have the ability to display marker changes that suggests the ability to undergo the EMT process. Seven day treatment of H358 with TGFβ alone or with the dual ligand combination of HGF and OSM (FIG. 2) produced a marked decrease in E-cadherin and a robust increase in vimentin, both hallmarks of an EMT. While repression of E-cadherin expression by TGF-beta was very substantial, it was not complete. However, addition of either HGF or OSM to the TGF-beta produced a more complete repression of E-cadherin expression, despite the fact that neither HGF or OSM as single agents produced significant E-cadherin repression or vimentin induction. Additionally, it is anticipated that other combinations of dual ligands that act via the same signal transduction pathways as HGF and OSM will similarly impact the EMT process, and will also work in the H358 cell line. Activation of the oncostatin M pathway acts via a JAK-Stat pathway. The ligand, HGF, acts through the tyrosine kinase receptor c-MET, which signals via the PI3K and MAPK pathways. It is thus anticipated that ligand stimulation of H358 cells through other tyrosine kinase receptors that signal through PI3K and MAPK would act as part of a dual ligand system in combination with oncostatin M to activate EMT; for example, ligand stimulation of IGF1-R, FGFR, RON, EGFR, VEGFR and PDGFR.

Figure 9B:
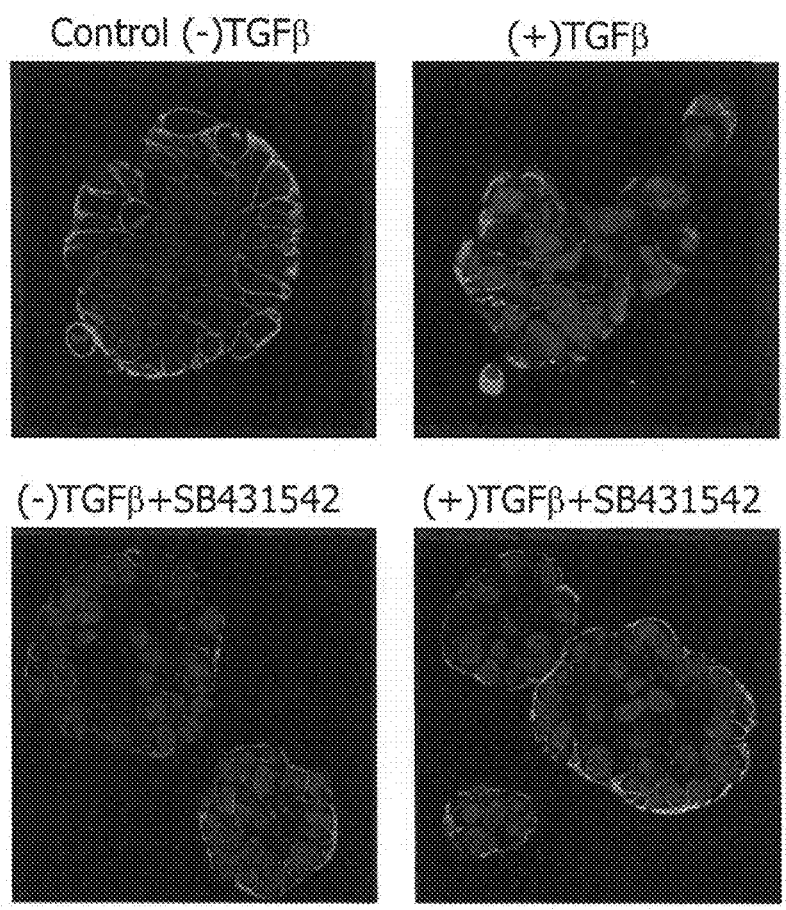

The ability to use an in vitro H358 cell model for testing inhibitors is demonstrated in 3-dimensional (3D) matrigel culture with H358 cells treated with the ligand, TGFβ in the presence and absence of the TGFβ small molecule inhibitor, SB431542. In the presence of the ligand TGFβ, the H358 cells were able to undergo an epithelial to mesenchymal transition exemplified by the appearance of the mesenchymal biomarker, vimentin (FIG. 9). In the presence of the TGFβ small molecule inhibitor, SB431542, the epithelial to mesenchymal transition was abrogated, exemplified by the absence of the mesenchymal biomarker, vimentin and the retention of the epithelial biomarker, E-cadherin.

Imaging of EMT in Vitro

We examined expression and localization of E-cadherin and vimentin in ligand-treated cells to determine the extent of EMT at the single cell level (FIG. 10). The two incomplete models of EMT, H358 cells treated with HGF or OSM, both result in a mixed population of cells. Some cells appear epithelial with functional, membrane-localized E-cadherin and no vimentin, while others express cytosolic E-cadherin and vimentin simultaneously, indicating a partial EMT. TGFβ induced a more complete EMT in H358 cells, with most cells expressing vimentin, and little functional E-cadherin. The dual-ligand or TGFβ multiple ligand (i.e. TGFβ, with OSM or HGF) models show more uniform populations of cells with near-complete loss of E-cadherin and strong expression of vimentin.

Analysis of Ligand-Induced EMT Signaling

Figure 11A:
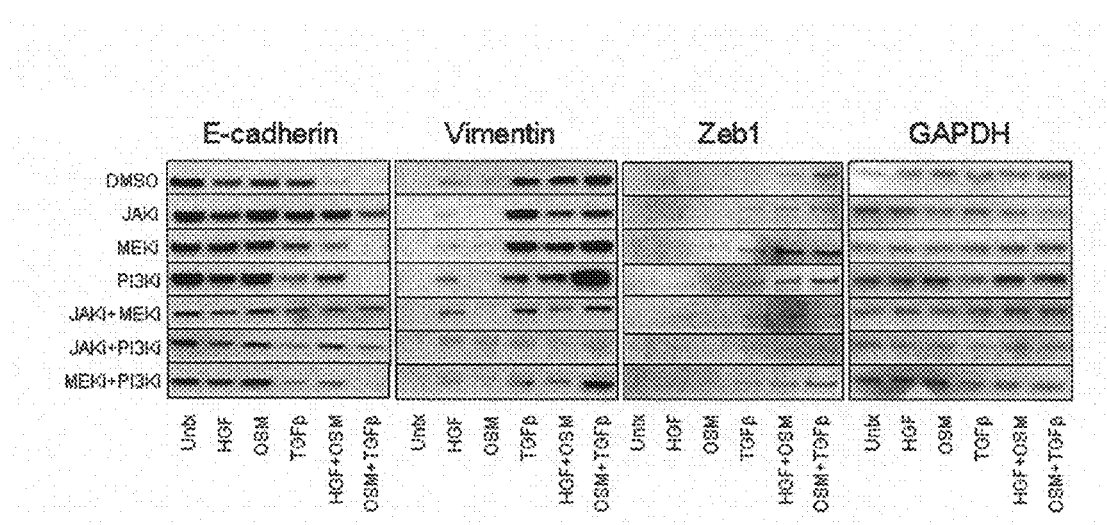
FIGS. 11A-B: OSM-induced EMT requires JAK and PI3K signaling. Cells were treated with inhibitor and ligand for 7 days. Cultures were harvested for protein, and Western blots were performed as described (A). Cells were imaged prior to harvesting on day 7 (B). The JAKi (JAK inhibitor) blocks EMT with OSM alone or in combination by morphology and markers. The PI3Ki (PI3 inhibitor) blocks morphology changes induced by HGF+OSM, and marker changes induced by all OSM ligand treatments.
Figure 11B:
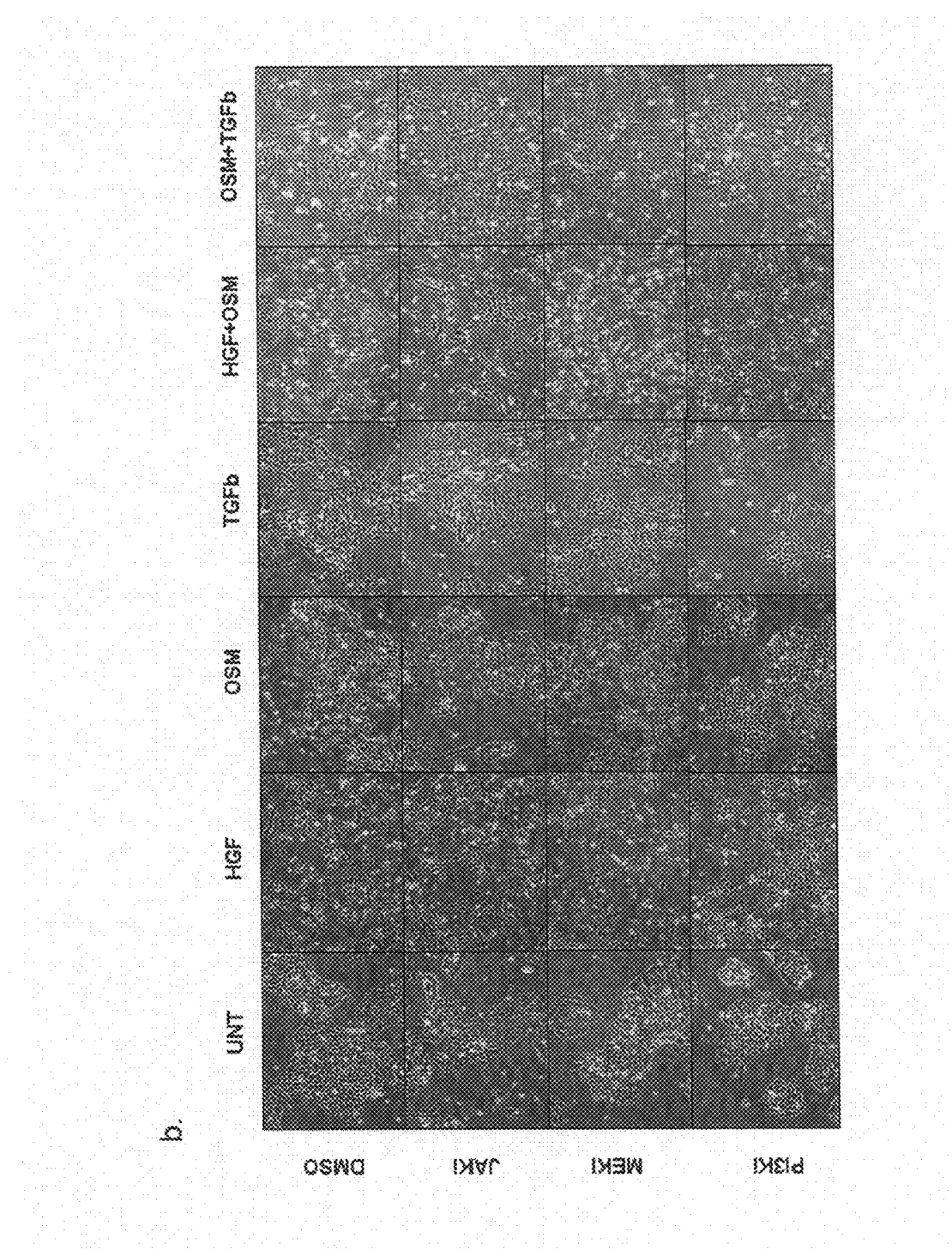

To determine the signaling downstream of HGF, OSM and TGFβ that is required for EMT in H358 cells, we monitored the effects of pharmacological inhibitors on the progress of ligand-induced EMT (FIG. 11). The MEK/ERK, JAK/STAT and PI3 Kinase pathways were inhibited individually and in combination, since these are well-characterized effectors of HGF, OSM and TGFβ. FIG. 11A shows inhibition of the JAK pathway blocked EMT in all OSM-induced models. The JAK inhibitor blocked downregulation of E-cadherin induced by OSM, TGFβ, HGF+OSM and TGFβ+OSM, and attenuated upregulation of vimentin by OSM, HGF+OSM and TGFβ+OSM. The morphological changes reflected the changes in markers (FIG. 11B). In contrast, inhibition of the MEK/ERK pathway had no effect on marker or morphological changes induced by any ligand. Inhibition of the PI3 kinase pathway resulted in a partial block of HGF+OSM marker and morphological changes. In addition, morphological changes induced by OSM and OSM+TGFβ were blocked by the PI3 kinase inhibitor without corresponding changes to E-cadherin or vimentin. These results indicate JAK and PI3 kinase signaling pathways are necessary for OSM-induced EMT in H358 cells.

EMT Increases Cell Migration and Invasion

Figure 12A:
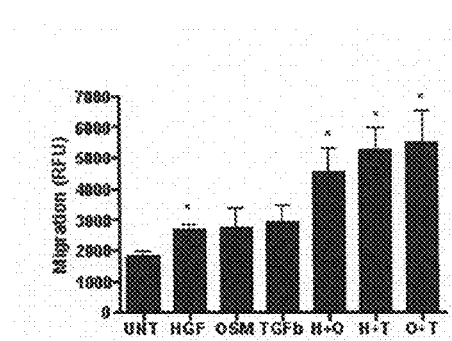
FIGS. 12A-B: EMT correlates with increased migration and invasion. Cells were treated for 7 days with ligand and assayed for migration (A) and invasion (B) in a modified Boyden chamber as described. (*) indicates p<0.05 by T-test. Migration and invasion progressively increase as cells transition from partial to complete EMT.
Figure 12B:
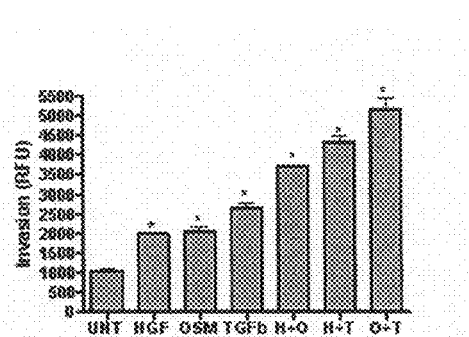

The morphological and marker changes induced by ligand in H358 cells correlated with increased ability to migrate and invade, as measured by a modified Boyden chamber assay (FIGS. 12A and 12B). Cells that had undergone complete EMT (i.e. treated with HGF+OSM, or TGFβ+OSM) were more motile than cells that had only partially transitioned (i.e. treated with HGF or OSM singly), suggesting the ability of a cell to migrate or invade is based on its status in the EMT program.

Ligand-Induced EMT is Reversible

Figure 13A:
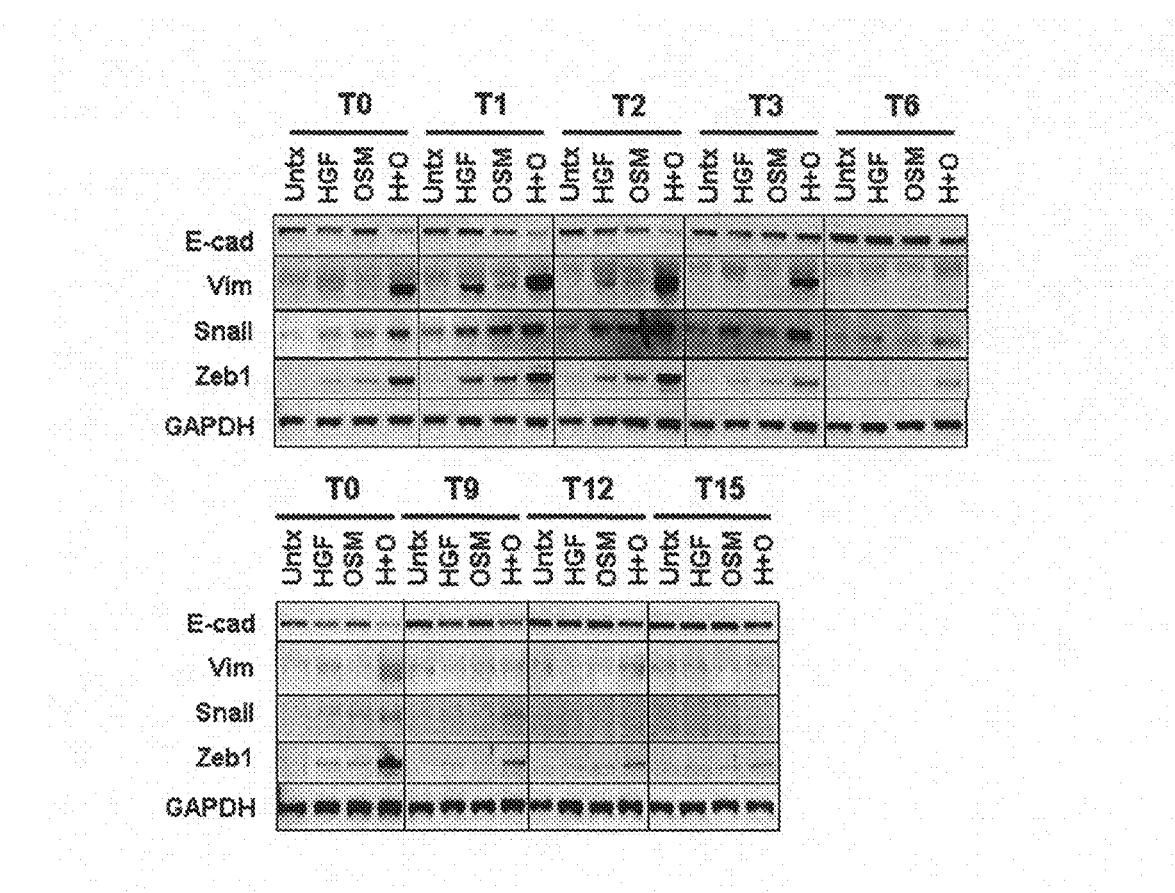
FIGS. 13A-C: H358 ligand-induced EMT is reversible. Cells were treated for 7 days with ligand and then reverted for 14 days upon ligand withdrawal. Markers (a.) and morphology (b.) were monitored over the 14 day reversion. Migration and invasion were evaluated after reversion for 14 days (c.) (*) indicates p<0.05 by T-test. Reversion to the epithelial phenotype is nearly complete by all three criteria, but notably with the dual ligand models, the cells do not achieve complete reversion. (Key: Untx, untreated; HGF, hepatocyte growth factor; OSM, oncostatin M; H+O, HGF plus OSM; Ecad, E-cadherin; Vim, vimentin).
Figure 13B:
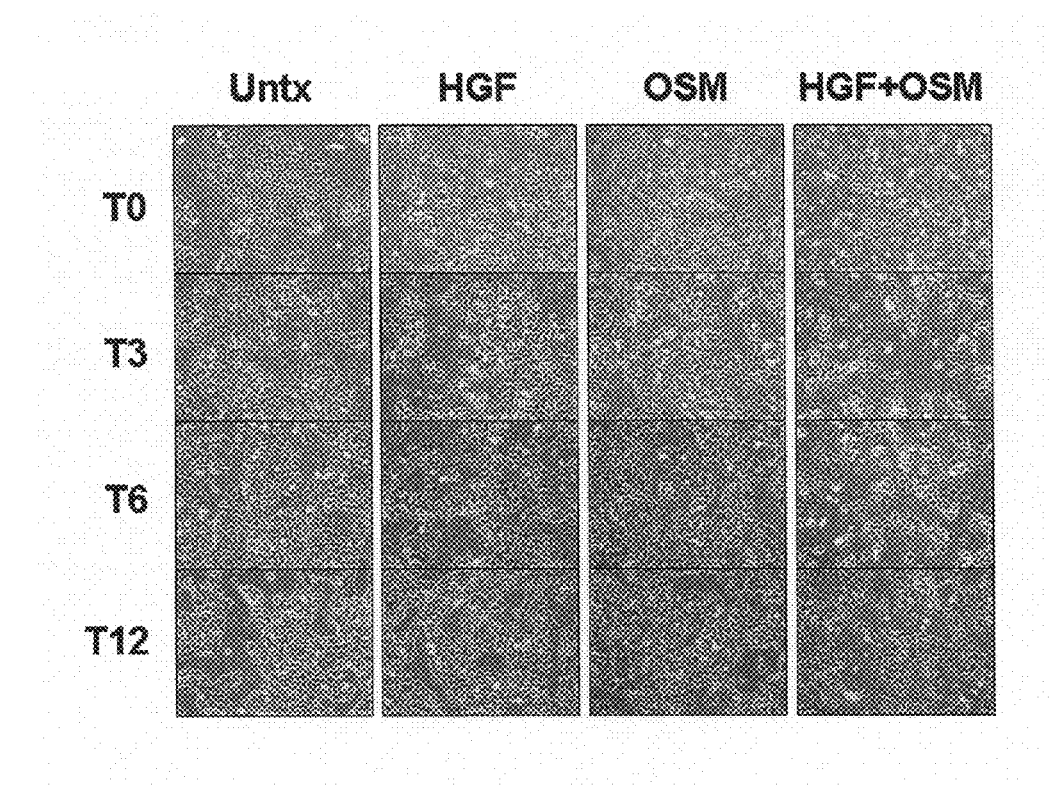
Figure 13C:
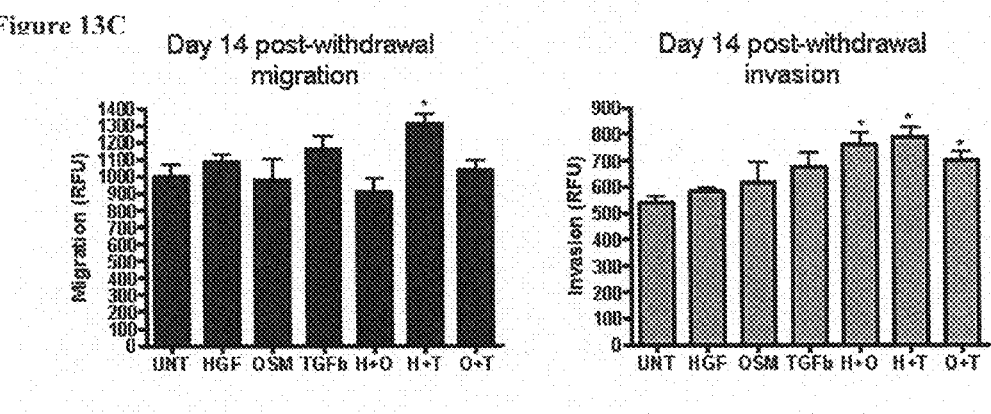

The cells in this model of EMT are in a metastable state and revert to the epithelial phenotype when the stimulus is withdrawn. FIGS. 13A and 13B show that when ligand-treated mesenchymal cells are cultured after the ligand is withdrawn both marker and morphology revert to the epithelial state. In the incomplete EMT models (HGF or OSM), reversion is near completion by 6 days, but the more complete dual-ligand or TGFβ multiple ligand models require more time (12 days) to revert to a comparable epithelial phenotype. Reverted cells also resemble epithelial cells in migration and invasion assays (FIG. 13C), however the reversion is not complete with the dual ligand models.

Inducible EMT Models

In order to create EMT models suitable for in vivo selection of anti-cancer agents and combinations thereof, specific EMT inducers were placed under the control of tetracycline analog inducible promoters and stably transfected into tumor lines shown capable of undergoing an EMT-like transition. This scheme is illustrated below in FIG. 3:

In the presence of doxycyclin, the H358-Snail stable transfectant (S4) showed induction of Snail, the loss or epithelial markers (eg. ErbB3) and the gain of mesenchymal markers (eg. Vimentin). GAPDH was used as a loading control (FIGS. 4 and 5). Snail and ZEB1 expression induced a more scattered, motile phenotype on H358 cells. The Snail phenotype was more pronounced than the ZEB phenotype.

TGFβ is one of the most potent inducers of EMT in cancer cells (see above). We generated a cell line containing a TET-inducible constitutively active TGFβ1 (a TGFβ1) gene. Induction of a TGFβ1 by doxycycline treatment of the cells for 7 days results in a downregulation of E-cadherin and an upregulation of vimentin expression, hallmark changes of an EMT. Three separate stable cell clones are shown in FIG. 6 below.

Imaging EMT in Vivo, and Other H358 in Vivo Studies.

In order to image tumor growth and invasion in vivo, luciferase readouts of cell number and location as well as epithelial and mesenchymal cell states were established. For example using the mesenchymal vimentin promoter fused 5' of the luciferase gene the mesenchymal state of tet-inducible cells may be measured. In H358 Tet-Snail cells transfected with the vimentin promoter-luciferase plasmid, luciferase expression was only observed in the mesenchymal state, i.e. when cells were exposed to doxycyclin, as shown herein (FIG. 7). Mesenchymal-specific promoter cells are useful in visualizing EMT in vivo both at the primary tumor site and metastatic sites, and important in measuring the activity in vivo of drugs which target EMT processes.

Luciferase expression allowed in for in vivo imaging in orthotopic implants of H358tetO-CMV-luci cells, as shown herein. Thus the location and number of cells can readily be measured in a non-invasive manner enabling anti-cancer agent evaluation, as shown for example in FIG. 8. H358 cells expressing luciferase can be imaged using CCD cameras in real-time in both orthotopic lung models (shown) and in more conventional flank injection models (not shown).

EMT is characterized by the loss of cell polarity and the induction of certain phenotypes more characteristic of mesenchymal cells; such as an altered, more fibroblast like morphology and increased cell motility. Consistent with these changes, the loss of E-cadherin and the gain of vimentin are well established hallmarks which can be used to identify the process of EMT (Thiery, J. P. (2002) Nat. Rev. Cancer 2:442-454; Savagner, P. (2001) Bioessays 23:912-923; Kang Y. and Massague, J. (2004) Cell 118:277-279; Julien-Grille, S., et al. Cancer Research 63:2172-2178; Bates, R. C. et al. (2003) Current Biology 13:1721-1727; Lu Z., et al. (2003) Cancer Cell. 4(6):499-515; Hugo H (2007) J Cell Physiol. 213(2):374-83; Lee J M (2006) J Cell Biol. 172(7):973-81.). As such, the epithelial (Epi) biomarker E-cadherin, and the mesenchymal (Mes) biomarker vimentin expression levels were evaluated after gene induction in xenografts from SCID mice bearing H358 inducible (a TGFβ, Zeb1, or Snail) subcutaneous tumors. Expression of the inducible gene product and protein biomarkers of EMT were analyzed by immunoblotting analysis of the lysates from the whole tumor following 7 days of doxycyline treatment.

Figure 16:
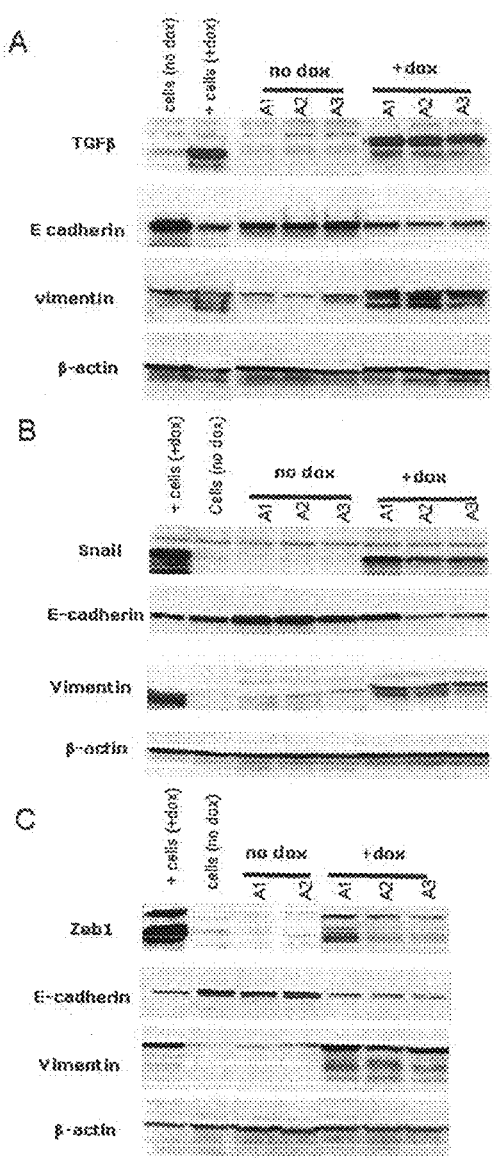
FIGS. 16A-C: Gene induction and EMT marker change in vivo. (A) Tumor lysates are probed for induction of constitutively active TGF-beta as well as expression of E-cadherin, vimentin and B-actin in the absence or presence of doxycycline (dox) treatment. (B) Tumor lysates are probed for induction of Snail as well as expression of E-cadherin, vimentin and B-actin in the absence or presence of doxycycline (dox) treatment. (C) Tumor lysates are probed for induction of Zeb-1 as well as expression of E-cadherin, vimentin and B-actin in the absence or presence of doxycycline (dox) treatment.

In the H358 tet-on a TGFβ (constitutively active) model, the secreted protein is induced when the animals are given doxycyline water (0.5 mg/ml). It is well established that in response to TGFβ signaling, cells may transcriptionally down-regulate E-cadherin, and upregulate mesenchymal genes such as vimentin (Zavadil J (2005) Oncogene 24(37):5764-74; Moustakas A (2007) Cancer Sci. 98(10):1512-20; Pennison S M. (2007) Curr Opin Oncol. 19(6):579-85; Leivonen S K (2007) Int J Cancer. 15; 121(10):2119-24; Yang J. (2008) Dev Cell. (6):818-29; Kim J H (2007) J Korean Med Sci.:898-904; Rees J. (2006) Cancer Research: 66(19): 9583-90). Western blotting of the H358 Tet-on a TGFβ tumors from animals exposed to doxycycline demonstrated induction of the TGFβ gene, with a concomitant decrease in E-cadherin and an increase in vimentin compared to control tumors of the same type from non-doxycycline treated animals (FIG. 16A). To normalize for loading, the housekeeping gene β-actin was utilized. In an identical manner, Snail was induced in H358 tet-on Snail tumors when the animals are given doxycyline water (0.5 mg/ml). Snail is a transcriptional repressor which directly down-regulates transcription of many epithelial genes, including E-cadherin, by binding to the E-cadherin gene promoter and preventing transcription. This loss of E-cadherin allows an increase in B-catenin mediated signaling and induction of several mesenchymal related genes such as vimentin. (Peinado H (2007) Nat Rev Cancer. 7(6):415-28; Moreno-Bueno G. (2008) Oncogene: 24; 27(55):6958-69; Becker K F (2007) Cells Tissues Organs. 85(1-3):204-12). Consistent with this biology, induction of the Snail protein in tumors consisting of the H358 tet-on Snail cells caused marked reduction in levels of the E-cadherin protein, and a marked increase in the expression of vimentin, compared to tumors of the same type from animals not adminstered doxycycline (FIG. 16B). As before, the housekeeping gene β-actin was utilized to normalize for protein loading. Finally, in an identical manner, Zeb1 was induced in H358 tet-on Zeb1 tumors when the animals are given doxycyline water (0.5 mg/ml). Analogous to Snail, Zeb1 is also a repressor E-cadherin transcription and inducer of mesenchymal genes (Peinado H (2007) Nat Rev Cancer. 7(6):415-28; Moreno-Bueno G. (2008) Oncogene: 24; 27(55):6958-69; Becker K F (2007) Cells Tissues Organs. 85(1-3):204-12). As in the Snail model, induction of Zeb1 caused the expected alteration in the classical EMT hallmarks E-cadherin and vimentin (FIG. 16C). To normalize for loading, the housekeeping gene β-actin was again utilized. These changes, observed in all three models, are consistent with the gene expression changes which occur during EMT.

In EMT, the loss of cell-cell contact is also characterized by morphological changes. In order to verify the EMT marker changes observed through western blotting of H358 tumors, formalin-fixed, paraffin embedded (FFPE) sections of the H358 inducible tumors were generated and EMT marker expression through immuno-histochemistry (IHC) were assayed. In addition, this methodology permits examination any EMT related pathological differences in the tumors when the gene of interest is induced by doxycycline. With this methodology, the hallmark EMT markers E-cadherin and vimentin can readily be examined after tet-inducible genes are expressed. As indicated by the western blotting data, dramatic changes in expression of these proteins are obvious by the IHC methodology in all three models when compared to identical tumors in animals not given doxycycline water (FIG. 17).

Figure 17A:
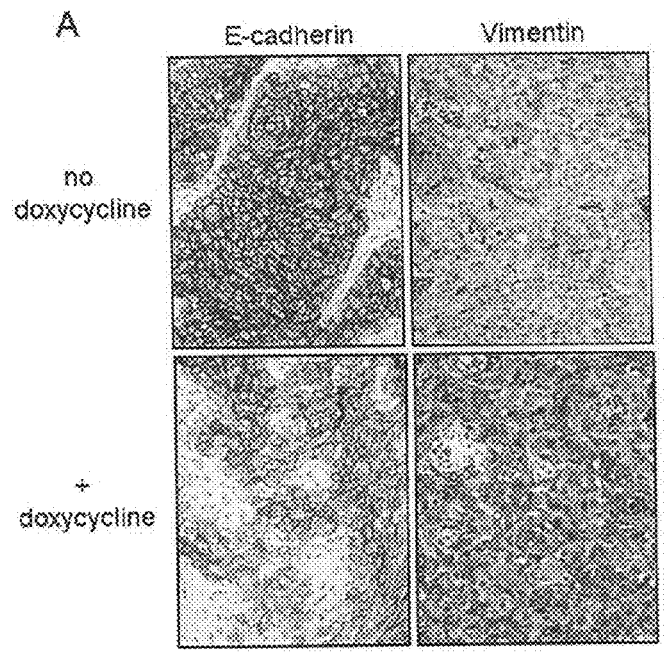
FIGS. 17A-C: Analysis of in vivo EMT phenotypes by IHC. (A) FFPE tumors from H358tetO-aTGF-beta xenografts are evaluated for expression of E-cadherin and vimentin in the absence or presence of doxycycline treatment. (B) FFPE tumors from H358tetO-Snail xenografts are evaluated for induction of Snail expression as well as expression of E-cadherin and vimentin in the absence or presence of doxycycline treatment. (C) FFPE tumors from H358tetO-Zeb-1 xenografts are evaluated for induction of Snail expression as well as expression of E-cadherin and vimentin in the absence or presence of doxycycline treatment. (A) When compared to identical tumors in animals not given doxyxycline water, it is clear that aTGFIβ expression caused down-regulation of E-cadherin. The cells in the control tumors consist of compact, well defined epithelial cell morphology. In contrast, in the tumors where aTGFIβ is induced (bottom panels) show significantly increased stroma, disrupted tumor architecture, and frequent spindle-shaped cells. As expected, autocrine TGFIβ caused upregulation of vimentin, characterized by the increased staining intensity in the perinuclear area of the epithelial cells. In contrast, only the stromal cells show vimentin staining in the un-induced tumors. (B) Snail is induced in H358 tet-on Snail tumors when the animals are given doxycyline water (bottom panels). Strong nuclear Snail staining is observed in all the cells in tumors from animals given doxyxycline. Snail expression caused a clear down-regulation of E-cadherin and up-regulation of vimentin as described above. (C) Zeb1 is induced in H358 tet-on Zeb1 tumors when the animals are given doxycyline water. Although most cells expressed Zeb1 with doxycycline administration, it was not detectable in every cell (bottom panels). Similar to the other models, E-cadherin was down-regulated and vimentin was up-regulated compared to similar tumors in animals not given doxycycline water. The pattern of Ecadherin and vimentin expression was not consistent throughout the tumor, and may correlate with pockets of cells that do or do not express Zeb1.

Because it is a secreted, soluble protein, it is likely not possible to directly examine expression of TGFβ in the H358 tet-on a TGFβ tumors by IHC. However, from the histological readout, it is apparent that a TGFβ expression caused down-regulation of E-cadherin (FIG. 17A, top panel). Untreated tumors (top panels) show strong membrane E-cadherin and form compact, well defined epithelial cell beds with well defined regions of epithelial cells, supported by pockets of stroma spaced throughout the tumor. Expression of vimentin is limited to the stromal cells (FIG. 17A, top panel). In contrast, in the tumors where a TGFβ is induced (FIG. 17A, bottom panels), there is a marked alteration in the makeup of the tumor. There is a significant decrease in the number of epithelial cells and significantly increased stroma, creating an abnormal, disrupted tumor architecture. Additionally, the epithelial cells do not form as well defined cell beds as the control tumors, and there is significantly increased infiltration of fibroblasts within the epithelial cell beds. Notably, there is an increase in the presence of spindle-shaped cells, suggesting morphological changes characteristic to EMT. The epithelial cells show a general loss in cell surface E-cadherin expression, and a large percentage of the cells gain expression of perinuclear vimentin compared to untreated tumors. This alteration in EMT marker change and cell morphology is consistent with the effects of TGFβ signaling on epithelial cells. The overall changes in tumor architecture may be due to the ability of TGFβ to recruit stroma, or as a consequence of decreased epithelial cell aggregation and enhanced motility; or even a combination of both. All of these phenomena are consistent with the phenotypic changes seen with EMT caused by TGFβ signaling in tumors (TseJC (2007) J Cell Biochem. 101(4):816-29; De Wever O. (2008) Histochem Cell Biol:130(3):481-94).

Figure 17B:
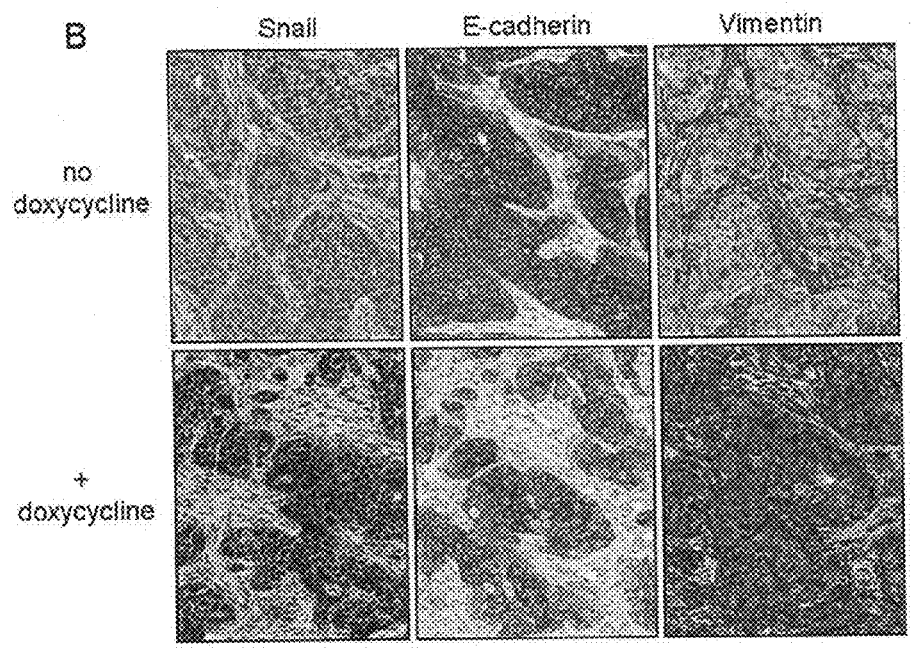

When Snail is induced in H358 tet-on Snail tumors, strong nuclear Snail staining is observed in all the cells (FIG. 17B, bottom panel). Comparatively, the control tumors show diffuse background staining, which is likely an artifact of non-specific binding of the primary antibody to an unrelated similar epitope (FIG. 17B, top panel). Similar to a TGFβ, Snail expression caused a clear down-regulation of membrane E-cadherin and up-regulation of vimentin in the tumor cells. Likewise to the a TGFβ model, in tumors where Snail was induced, there was a general disruption in the tumor architecture, as the ratio of tumor to stroma is significantly decreased. However, this appears to be different than the a TGFβ model, as the cells still form well defined epithelial beds, and the stroma does not seem to be recruited nor does it infiltrate into these epithelial beds. The loss of tumor cell content in these tumors may be due to the anti-proliferative effect of Snail, allowing the stromal content to exist in a higher ratio than normal, untreated tumors (FIG. 17B, top panel).

Figure 17C:
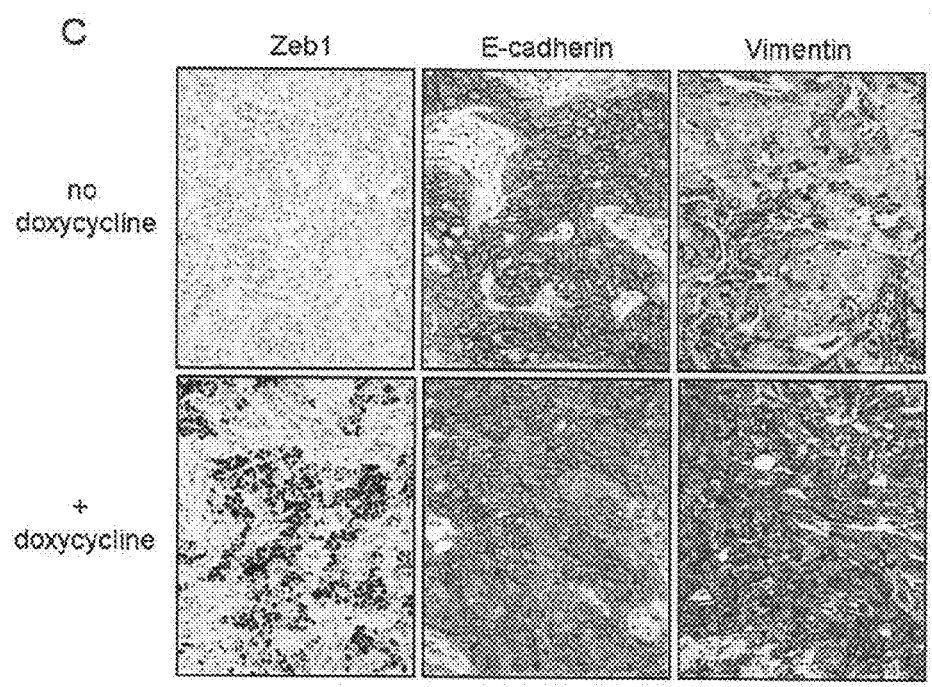

As well, when Zeb1 is induced in H358 tet-on Zeb1 tumors, most cells expressed Zeb1, but it was not detectable in every cell (FIG. 17C, bottom panels). Similar to the other models, E-cadherin was down-regulated and vimentin was up-regulated in the tumor cells compared to similar tumors in animals not given doxycycline. The pattern of E-cadherin and vimentin expression was not consistent throughout the tumor; there were groupings of cells that frequently cells that expressed no Ecadherin whatsoever; or had mislocalized (cytoplasmic) E-cadherin. The pattern of vimentin staining was similar, in that there were groupings which expressed perinuclear vimentin. Although double immuno-staining of Zeb and E-cadherin or Zeb1 and vimentin were not performed, alignment of serial sections suggested that these regions correlated with pockets of cells that do or do not express Zeb1 (data not shown). These observations are consistent with the role of Zeb1 as a repressor of E-cadherin transcription, and also as a direct regulator of microRNAs (MiRs) that regulate EMT processes (Shirakihara T (2007) Mol Biol Cell: 3533-44; Gregory P A (2008) Cell Cycle 7(20):3112-8; Gregory P A (2008) Nat Cell Biol 10(5):593-601; Park S M (2008) Genes Dev. 22(7):894-907; Burk U (2008) EMBO. Rep. 9(6): 582-9).

Figure 18:
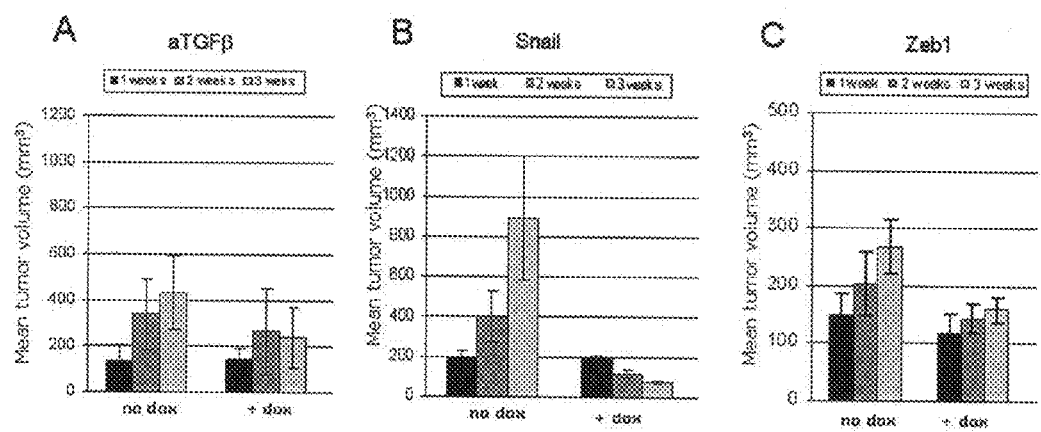
FIGS. 18A-C: Growth effects of EMT gene induction in vivo. Doxycycline dependent EMT-like transitions induced by aTGFβ, Snail, and Zeb expression in H358 cells slow tumor cell proliferation to varying degrees in subcutaneous xenografts. (A) Mean tumor volume of H358tet on-aTGFβ xenografts at 1 (black bars), 2 (dark grey bars) or 3 (light grey bars) weeks of growth in the absence or presence of doxycycline (dox) treatment (B) Mean tumor volume of H358tet on-Snail xenografts at 1 (black bars), 2 (dark grey bars) or 3 (light grey bars) weeks of growth in the absence or presence of doxycycline (dox) treatment. (C) Mean tumor volume of H358tet on-Zeb1 xenografts at 1 (black bars), 2 (dark grey bars) or 3 (light grey bars) weeks of growth in the absence or presence of doxycycline (dox) treatment.

TGFβ is known to have growth suppressive or growth promoting effects, depending on the makeup of TGFβ receptors on the cells. As well, alterations in the expression of other BMP family members and SMAD signaling determines whether or not TGFβ has a growth inhibitory effect on tumor epithelial cells (Pardali K (2007) Biochim Biophys Acta. 1775(1):21-62; Rahimi R A (2007), J Cell Biochem. 102(3): 593-608). As repressors of transcriptional activity, Snail and Zeb1 are also known to cause growth suppressive effects on epithelial cells (Zavadil J (2005) Oncogene 24(37):5764-74; Moustakas A (2007) Cancer Sci. 98(10):1512-20; Pennison M. (2007) Curr Opin Oncol. 19(6):579-85; Leivonen S K (2007) Int J Cancer. 15; 121(10):2119-24; Yang J. (2008) Dev Cell. (6):818-29; Rees J. (2006) Cancer Research: 66(19): 9583-90). Therefore, differences in subcutaneous tumor volumes over time in the H358 tet-on (a TGFβ, Snail, Zeb1) models were compared when the animals were administered 0.5 mg/ml doxycycline in the drinking water. To this end, growth suppressive effects of the gene induced in all three models were noted to varying degrees (FIG. 18). In all 3 cases, there was minimal tumor growth inhibition after 7 days of doxycycline treatment compared to the untreated groups. However, the a TGFβ model only showed modest growth inhibition up to 21 days upon gene induction (FIG. 12A). The Zeb1 model showed growth stasis up to 21 days following gene induction (FIG. 18B). In contrast, the tumors in the Snail model regressed upon gene induction up to 21 days (FIG. 18C). Although this result was unexpected, it is consistent with the known growth suppressive effects of these genes.

The apparent loss of epithelial cell content and abnormal architecture within these models as seen in the immunohistochemistry evaluations suggests that the induction of these genes may cause apoptosis and/or cell cycle arrest. Although not examined, this concept would also be in line with the established effects of these gene products on cells. This growth suppressive effect may be specific to context of the tumor microenvironment, or may be overcome over time as the cells continue to progress through EMT. Elucidation of this will require further studies examining the roles of the induced gene and EMT in specific disease states.

In conclusion, it is found that in all models, doxycycline induced gene expression resulted in a significant decrease in E-cadherin, a gain of vimentin, and a reduction in cell proliferation as measured by overall tumor growth. In addition, noticeable alteration in tumor architecture and individual cell morphology was observed in the EMT-induced tumors. These concomitant changes in transcription, protein expression, morphology and proliferation are consistent with the overall process of EMT. Thus, these H358 NSCLC models represent suitable in vivo, inducible systems for evaluating the effect of EMT on tumor pathology. These models are therefore useful for better evaluating the role of EMT in cancer progression, drug resistance, and the identification of novel drug targets related to EMT and pharmaceuticals acting thereon.

Genomic and Proteomic EMT Model Analysis

EMT contributes to loss of erlotinib sensitivity in tumors as well as metastatic efficiency of disseminating tumor cells, which combined may result in a significant reduction in patient survival. In vitro models of EMT facilitate drug discovery aimed at discovering targets that control this process. Characterization of transcriptional and signaling changes in EMT models will result in a better understanding of the EMT process and will identify critical points of regulation that may indicate druggable targets.

Figure 14:
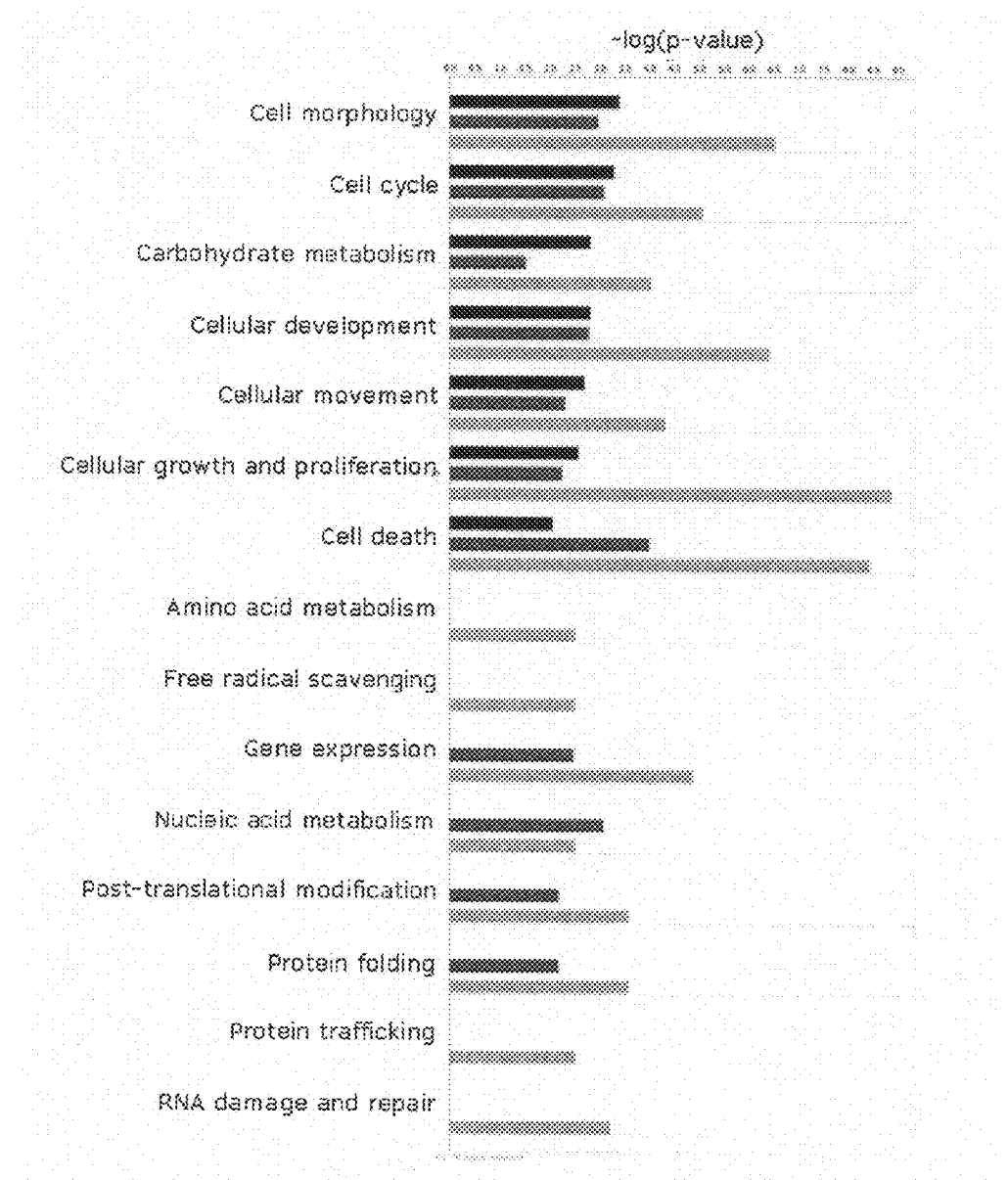
FIG. 14: Changes in cell functions by 7 day EMT ligand treatment in H358 cells. A list of 60 genes altered by ligand treatment in both Affymetrix microarray and proteomics analysis was analyzed using IPA software (Ingenuity). Changes in genes associated with cell functions are indicated above (black=HGF; dark grey=OSM; light grey=HGF+OSM).

To characterize the ligand-driven H358 EMT models, global changes to both mRNA and protein were profiled under conditions that induce incomplete EMT (HGF or OSM single ligand) or complete EMT (HGF+OSM dual ligand). Changes to mRNA transcripts were identified using Affymetrix human expression microarrays, and identified changes to protein expression and tyrosine phosphorylation by mass spectrometry proteomics. Analysis of the data revealed synergistic signaling with the combination treatment of HGF and OSM, resulting in distinct patterns of regulation of a broad array of cell functions. There was a significant increase in the number and magnitude of changes to mRNA, protein expression and tyrosine phosphorylation when cells underwent complete EMT compared to incomplete EMT. When cell functions influenced by these gene changes were examined, we found multiple patterns of regulation, but two of particular interest (FIG. 14). First, some cell functions were changed by both incomplete and complete EMT, but complete EMT had a more significant effect. Cell morphology, cell growth and cell death exhibited this pattern of regulation. Second, some cell functions were unaffected by treatments which resulted in incomplete EMT, but were affected when the cells underwent complete EMT. Amino acid metabolism, free radical scavenging, and RNA damage and repair fell under this pattern of regulation. Overall, the changes in specific cell functions induced by complete EMT in H358 cells indicate possible mechanisms of tumor cell survival, and the signaling pathways that control these functions.

Abbreviations:

EGF, epidermal growth factor; EGFR, epidermal growth factor receptor; EGFR-TKI, Epidermal Growth Factor Receptor Tyrosine Kinase Inhibitor; EMT, epithelial-to-mesenchymal transition; MET, mesenchymal-to-epithelial transition; NSCL, non-small cell lung; NSCLC, non-small cell lung cancer; HNSCC, head and neck squamous cell carcinoma; CRC, colorectal cancer; MBC, metastatic breast cancer; Brk, Breast tumor kinase (also known as protein tyrosine kinase 6 (PTK6)); FCS, fetal calf serum; LC, liquid chromatography; MS, mass spectrometry; IGF-1, insulin-like growth factor-1; TGFα, transforming growth factor alpha; HB-EGF, heparin-binding epidermal growth factor; LPA, lysophosphatidic acid; $IC_{50}$, half maximal inhibitory concentration; pY, phosphotyrosine; wt, wild-type; PI3K, phosphatidyl inositol-3 kinase; GAPDH, glyceraldehyde 3-phosphate dehydrogenase; MAPK, mitogen-activated protein kinase; PDK-1,3-Phosphoinositide-Dependent Protein Kinase 1; Akt, also known as protein kinase B, is the cellular homologue of the viral oncogene v-Akt; mTOR, mammalian target of rapamycin; 4EBP1, eukaryotic translation initiation factor-4E (mRNA cap-binding protein) Binding Protein-1, also known as PHAS-I; p70S6K, 70 kDa ribosomal protein-S6 kinase; eIF4E, eukaryotic translation initiation factor-4E (mRNA cap-binding protein); Raf, protein kinase product of Raf oncogene; MEK, ERK kinase, also known as mitogen-activated protein kinase; ERK, Extracellular signal-regulated protein kinase, also known as mitogen-activated protein kinase; PTEN, "Phosphatase and Tensin homologue deleted on chromosome 10", a phosphatidylinositol phosphate phosphatase; pPROTEIN, phospho-PROTEIN, "PROTEIN" can be any protein that can be phosphorylated, e.g. EGFR, ERK, S6 etc; PBS, Phosphate-buffered saline; TGI, tumor growth inhibition; WFI, Water for Injection; SDS, sodium dodecyl sulfate; ErbB2, "v-erb-b2 erythroblastic leukemia viral oncogene homolog 2", also known as HER-2; ErbB3, "v-erb-b2 erythroblastic leukemia viral oncogene homolog 3", also known as HER-3; ErbB4, "v-erb-b2 erythroblastic leukemia viral oncogene homolog 4", also known as HER-4; FGFR, Fibroblast Growth Factor Receptor; DMSO, dimethyl sulfoxide.

INCORPORATION BY REFERENCE

All patents, published patent applications and other references disclosed herein are hereby expressly incorporated herein by reference.

EQUIVALENTS

Those skilled in the art will recognize, or be able to ascertain, using no more than routine experimentation, many equivalents to specific embodiments of the invention described specifically herein. Such equivalents are intended to be encompassed in the scope of the following claims.

What is claimed is:

1. A method of identifying an agent that inhibits tumor cells from undergoing an epithelial-to-mesenchymal transition (EMT), comprising contacting a sample of cells of the epithelial tumor cell line H358 with a test agent to be screened,
   contacting the sample with a single- or dual-protein ligand preparation that induces an epithelial-to-mesenchymal transition in H358 cells,
   determining whether the test agent inhibits the tumor cells in the sample from undergoing an epithelial-to-mesenchymal transition, by comparing the level of a biomarker whose level is indicative of the EMT status of the sample tumor cells to the level of the same biomarker in an identical sample of H358 cells not contacted with the test agent, and thus determining whether the test agent is an agent that inhibits tumor cells from undergoing an epithelial-to-mesenchymal transition.

2. The method of claim 1, wherein the single-protein ligand that induces an epithelial-to-mesenchymal transition in H358 cells is selected from any of the protein ligands that bind to and activate the EGF receptor, TGF-beta receptor II, TNF receptor, or the IL-4 receptor.

3. The method of claim 2, wherein the single-protein ligand that induces an epithelial-to-mesenchymal transition in H358 cells is selected from EGF, TGF-beta, TNF-alpha, IL-4, TGF-α, HB-EGF, amphiregulin, betacellulin, epiregulin, epigen, TNF-beta, TGFbeta-1, TGFbeta-2, TGFbeta-3, a TGFbeta hererodimer, or IL-13.

4. The method of claim 3, wherein the single-protein ligand that induces an epithelial-to-mesenchymal transition in H358 cells is selected from EGF, TGFbeta, TNFalpha, or IL-4.

5. The method of claim 1, wherein the dual-protein ligands that induce an epithelial-to-mesenchymal transition in H358 cells are oncostatin-M to its receptor oncostatin-M plus one ligand that binds to a tyrosine kinase receptor and activates the same signal transduction pathways that are activated by the binding of HGF to its receptor.

6. The method of claim 5, wherein the dual-protein ligands that induce an epithelial-to-mesenchymal transition in H358 cells are oncostatin-M receptor oncostatin-M plus one ligand that binds to and activates IGF1-R, FGFR1, FGFR2, FGFR3, FGFR4, a heterodimer FGF receptor, RON, EGFR, HER-4, a heterodimers HER receptor, VEGFR-1, VEGFR-2, VEGFR-3, PDGFRαα, PDGFRββ, or PDGFRαβ.

7. The method of claim 6, wherein the dual-protein ligands that induce an epithelial-to-mesenchymal transition in H358 cells are oncostatin-M; plus HGF, IGF-1, IGF-2, FGF1, FGF2, FGF3, FGF4, FGF5, FGF6, FGF7, FGF8, FGF8, FGF10, MSP, TGF-α, HB-EGF, amphiregulin, betacellulin, epiregulin, epigen, Heregulin, NRG-2, NRG-3, NRG-4, VEGF-A, VEGF-B, VEGF-C, VEGF-D, VEGF-E, PDGF-AA, PDGF-AB, PDGF-BB, PDGF-CC, or PDGF-DD.

8. The method of claim 7, wherein the dual-protein ligands that induce an epithelial-to-mesenchymal transition in H358 cells are oncostatin-M plus HGF.

9. The method of claim 1, wherein the biomarker whose level is indicative of the EMT status of the sample tumor cells is an epithelial cell biomarker.

10. The method of claim 9, wherein the epithelial cell biomarker is E-cadherin, CDH1 promoter activity, cytokeratin 8, cytokeratin 18, P-cadherin or erbB3.

11. The method of claim 1, wherein the biomarker whose level is indicative of the EMT status of the sample tumor cells is a mesenchymal cell biomarker.

12. The method of claim 11, wherein the mesenchymal cell biomarker is vimentin, fibronectin, N-cadherin, CDH1 methylation, zeb1, twist, FOXC2 or snail.

13. A method of identifying an agent that inhibits tumor cells that have undergone an epithelial-to-mesenchymal transition, comprising contacting a sample of cells of the epithelial tumor cell line H358 with a single- or dual-protein ligand preparation to induce an epithelial-to-mesenchymal transition in the H358 cells,
contacting the sample of cells with a test agent to be screened,
determining whether the test agent inhibits mesenchymal-like H358 cell growth,
and thus determining whether it is an agent that inhibits the growth of tumor cells that have undergone an epithelial-to-mesenchymal transition.

14. The method of claim 13, wherein the single-protein ligand that induces an epithelial-to-mesenchymal transition in H358 cells is selected from any of the protein ligands that bind to and activate the EGF receptor, TGF-beta receptor II, TNF receptor, or the IL-4 receptor.

15. The method of claim 14, wherein the single-protein ligand that induces an epithelial-to-mesenchymal transition in H358 cells is selected from EGF, TGF-beta, TNF-alpha, IL-4, TGF-α, HB-EGF, amphiregulin, betacellulin, epiregulin, epigen, TNF-beta, TGFbeta-1, TGFbeta-2, TGFbeta-3, a TGFbeta hererodimer, or IL-13.

16. The method of claim 15, wherein the single-protein ligand that induces an epithelial-to-mesenchymal transition in H358 cells is selected from EGF, TGFbeta, TNFalpha, or IL-4.

17. The method of claim 13, wherein the dual-protein ligands that induce an epithelial-to-mesenchymal transition in H358 cells are oncostatin-M plus one ligand that binds to a tyrosine kinase receptor and activates the same signal transduction pathways that are activated by the binding of HGF to its receptor.

18. The method of claim 17, wherein the dual-protein ligands that induce an epithelial-to-mesenchymal transition in H358 cells are oncostatin-M plus one ligand that binds to and activates IGF1-R, FGFR1, FGFR2, FGFR3, FGFR4, a heterodimer FGF receptor, RON, EGFR, HER-4, a heterodimers HER receptor, VEGFR-1, VEGFR-2, VEGFR-3, PDGFRαα, PDGFRββ, or PDGFRαβ.

19. The method of claim 18, wherein the dual-protein ligands that induce an epithelial-to-mesenchymal transition in H358 cells are oncostatin-M; plus HGF, IGF-1, IGF-2, FGF1, FGF2, FGF3, FGF4, FGF5, FGF6, FGF7, FGF8, FGF8, FGF10, MSP, TGF-α, HB-EGF, amphiregulin, betacellulin, epiregulin, epigen, Heregulin, NRG-2, NRG-3, NRG-4, VEGF-A, VEGF-B, VEGF-C, VEGF-D, VEGF-E, PDGF-AA, PDGF-AB, PDGF-BB, PDGF-CC, or PDGF-DD.

20. The method of claim 19, wherein the dual-protein ligands that induce an epithelial-to-mesenchymal transition in H358 cells are oncostatin-M plus HGF.

21. The method of claim 13, comprising, after the step of determining whether the test agent inhibits the growth of tumor cells that have undergone an epithelial-to-mesenchymal transition, the additional steps of
determining whether an agent that inhibits mesenchymal-like H358 tumor cell growth, also inhibits epithelial H358 tumor cell growth,
and thus determining whether it is an agent that specifically inhibits the growth of tumor cells that have undergone an epithelial-to-mesenchymal transition.

22. The method of claim 13, wherein in the step of determining whether the test agent inhibits mesenchymal-like H358 tumor cell growth, it is determined that the test agent does so by stimulating apoptosis of said tumor cells.

23. The method of claim 13, wherein in the step of determining whether the test agent inhibits mesenchymal-like H358 tumor cell growth, it is determined that the test agent does so by inhibiting proliferation of said tumor cells.

24. A method of identifying an agent that stimulates mesenchymal-like tumor cells to undergo a mesenchymal-to-epithelial transition, comprising
contacting a sample of cells of the epithelial tumor cell line H358 with a single- or dual-protein ligand preparation to induce an epithelial-to-mesenchymal transition in the H358 cells,
contacting the sample of cells with a test agent to be screened, determining whether the test agent stimulates the mesenchymal-like H358 cells in the sample to undergo a mesenchymal to epithelial transition, by comparing the level of a biomarker whose level is indicative of the EMT status of the sample tumor cells to the level of the same biomarker in an identical sample of mesenchymal-like H358 cells not contacted with the test agent, and thus determining whether the test agent is an agent that stimulates mesenchymal-like tumor cells to undergo a mesenchymal-to-epithelial transition.

25. The method of claim 24, wherein the single-protein ligand that induces an epithelial-to-mesenchymal transition in H358 cells is selected from any of the protein ligands that bind to and activate the EGF receptor, TGF-beta receptor II, TNF receptor, or the IL-4 receptor.

26. The method of claim 25, wherein the single-protein ligand that induces an epithelial-to-mesenchymal transition in H358 cells is selected from, EGF, TGF-beta, TNF-alpha, IL-4, TGF-α, HB-EGF, amphiregulin, betacellulin, epiregulin, epigen, TNF-beta, TGFbeta-1, TGFbeta-2, TGFbeta-3, a TGFbeta hererodimer, or IL-13.

27. The method of claim 26, wherein the single-protein ligand that induces an epithelial-to-mesenchymal transition in H358 cells is selected from EGF, TGFbeta, TNFalpha, or IL-4.

28. The method of claim 24, wherein the dual-protein ligands that induce an epithelial-to-mesenchymal transition in H358 cells are oncostatin-M plus one ligand that binds to a tyrosine kinase receptor and activates the same signal transduction pathways that are activated by the binding of HGF to its receptor.

29. The method of claim 28, wherein the dual-protein ligands that induce an epithelial-to-mesenchymal transition in H358 cells are oncostatin-M plus one ligand that binds to and activates IGF1-R, FGFR1, FGFR2, FGFR3, FGFR4, a heterodimer FGF receptor, RON, EGFR, HER-4, a heterodimers HER receptor, VEGFR-1, VEGFR-2, VEGFR-3, PDGFRαα, PDGFRββ, or PDGFRαβ.

30. The method of claim 29, wherein the dual-protein ligands that induce an epithelial-to-mesenchymal transition in H358 cells are oncostatin-M; plus HGF, IGF-1, IGF-2, FGF1, FGF2, FGF3, FGF4, FGF5, FGF6, FGF7, FGF8, FGF8, FGF10, MSP, TGF-α, HB-EGF, amphiregulin, betacellulin, epiregulin, epigen, Heregulin, NRG-2, NRG-3, NRG-4, VEGF-A, VEGF-B, VEGF-C, VEGF-D, VEGF-E, PDGF-AA, PDGF-AB, PDGF-BB, PDGF-CC, or PDGF-DD.

31. The method of claim 30, wherein the dual-protein ligands that induce an epithelial-to-mesenchymal transition in H358 cells are oncostatin-M plus HGF.

32. The method of claim 24, wherein the biomarker whose level is indicative of the EMT status of the sample tumor cells is an epithelial cell biomarker.

33. The method of claim 32, wherein the epithelial cell biomarker is E-cadherin, CDH1 promoter activity, cytokeratin 8, cytokeratin 18, P-cadherin or erbB3.

34. The method of claim 24, wherein the biomarker whose level is indicative of the EMT status of the sample tumor cells is a mesenchymal cell biomarker.

35. The method of claim 34, wherein the mesenchymal cell biomarker is vimentin, fibronectin, N-cadherin, CDH1 methylation, zeb1, twist, FOXC2 or snail.

36. A method of preparing a composition comprising a chemical compound which inhibits the growth of tumor cells that have undergone an epithelial-to-mesenchymal transition, which comprises contacting a sample of cells of the epithelial tumor cell line H358 with a test agent to be screened, contacting the sample with a single- or dual-protein ligand preparation that induces an epithelial-to-mesenchymal transition in H358 cells, determining whether the test agent inhibits the tumor cells in the sample from undergoing an epithelial-to-mesenchymal transition by comparing the level of a biomarker whose level is indicative of the EMT status of the sample tumor cells to the level of the same biomarker in an identical sample of H358 cells not contacted with the test agent, and thus determining whether the test agent is an agent that inhibits tumor cells from undergoing an epithelial-to-mesenchymal transition, and admixing the test agent so identified with a carrier, thereby preparing said composition.

37. A method of preparing a composition comprising a chemical compound which inhibits the growth of tumor cells that have undergone an epithelial-to-mesenchymal transition, which comprises contacting a sample of cells of the epithelial tumor cell line H358 with a single- or dual-protein ligand preparation to induce an epithelial-to-mesenchymal transition in the H358 cells, contacting the sample of cells with a test agent to be screened, determining whether the test agent inhibits mesenchymal-like H358 cell growth, and thus determining whether it is an agent that inhibits the growth of tumor cells that have undergone an epithelial-to-mesenchymal transition, and admixing the test agent so identified with a carrier, thereby preparing said composition.

38. A method of preparing a composition comprising a chemical compound which inhibits the growth of tumor cells that have undergone an epithelial-to-mesenchymal transition, which comprises contacting a sample of cells of the epithelial tumor cell line H358 with a single- or dual-protein ligand preparation to induce an epithelial-to-mesenchymal transition in the H358 cells, contacting the sample of cells with a test agent to be screened, determining whether the test agent stimulates the mesenchymal-like H358 cells in the sample to undergo a mesenchymal-to-epithelial transition by comparing the level of a biomarker whose level is indicative of the EMT status of the sample tumor cells to the level of the same biomarker in an identical sample of mesenchymal-like H358 cells not contacted with the test agent, and thus determining whether the test agent is an agent that stimulates mesenchymal-like tumor cells to undergo a mesenchymal-to-epithelial transition, and admixing the test agent so identified with a carrier, thereby preparing said composition.

39. A mesenchymal-like tumor cell preparation for use in the identification of anti-cancer agents, wherein said tumor cell preparation is prepared by a process comprising:

contacting a sample of cells of the epithelial tumor cell line H358 with a single- or dual-protein ligand preparation to induce an epithelial-to-mesenchymal transition in the H358 cells, wherein the single-protein ligand that induces an epithelial-to-mesenchymal transition in H358 cells is selected from any of the protein ligands that bind to and activate the EGF receptor; TGF-beta receptor II; TNF receptor; or the IL-4 receptor, and wherein the dual-protein ligands that induce an epithelial-to-mesenchymal transition in H358 cells are oncostatin-M plus one ligand that binds to a tyrosine kinase receptor and activates the same signal transduction pathways that are activated by the binding of HGF to its receptor.

40. The cell preparation of claim 39, wherein the single-protein ligand that induces an epithelial-to-mesenchymal transition in H358 cells is selected from EGF, TGF-beta, TNF-alpha, IL-4, TGF-α, HB-EGF, amphiregulin, betacellulin, epiregulin, epigen, TNF-beta, TGFbeta-1, TGFbeta-2, TGFbeta-3, a TGFbeta hererodimer, or IL-13.

41. The cell preparation of claim 40, wherein the single-protein ligand that induces an epithelial-to-mesenchymal transition in H358 cells is selected from EGF, TGFbeta, TNFalpha, or IL-4.

42. The cell preparation of claim 39, wherein the dual-protein ligands that induce an epithelial-to-mesenchymal transition in H358 cells are oncostatin-M plus one ligand that binds to and activates IGF1-R, FGFR1, FGFR2, FGFR3, FGFR4, a heterodimer FGF receptor, RON, EGFR, HER-4, a heterodimers HER receptor, VEGFR-1, VEGFR-2, VEGFR-3, PDGFRαα, PDGFRββ, or PDGFRαβ.

43. The cell preparation of claim 42, wherein the dual-protein ligands that induce an epithelial-to-mesenchymal transition in H358 cells are oncostatin-M; plus HGF, IGF-1, IGF-2, FGF1, FGF2, FGF3, FGF4, FGF5, FGF6, FGF7, FGF8, FGF8, FGF10, MSP, TGF-α, HB-EGF, amphiregulin, betacellulin, epiregulin, epigen, Heregulin, NRG-2, NRG-3, NRG-4, VEGF-A, VEGF-B, VEGF-C, VEGF-D, VEGF-E, PDGF-AA, PDGF-AB, PDGF-BB, PDGF-CC, or PDGF-DD.

44. The cell preparation of claim 43, wherein the dual-protein ligands that induce an epithelial-to-mesenchymal transition in H358 cells are oncostatin-M plus HGF.

45. A method of identifying an agent that inhibits tumor cells from undergoing an epithelial-to-mesenchymal transition, comprising contacting a sample of cells of the epithelial tumor cell line H358, which have been engineered to inducibly express a protein that stimulates an epithelial-to-mesenchymal transition in H358 cells, with a test agent to be screened,
    contacting the sample with a compound that induces the expression of said protein that stimulates an epithelial-to-mesenchymal transition in the engineered H358 cells,
    determining whether the test agent inhibits the tumor cells in the sample from undergoing an epithelial-to-mesenchymal transition, by comparing the level of a biomarker whose level is indicative of the EMT status of the sample tumor cells to the level of the same biomarker in an identical sample of engineered H358 cells not contacted with the test agent,
    and thus determining whether the test agent is an agent that inhibits tumor cells from undergoing an epithelial-to-mesenchymal transition.

46. The method of claim 45, wherein the protein that is inducibly expressed and stimulates an epithelial-to-mesenchymal transition in H358 cells is Zeb-1, Snail, constitutively active TGF-beta, co-expressed HGF and OSM, TNF-alpha, constitutively active cMET receptor, activated Src kinase, v-Src, Src Y530F mutant, IL-4, IL-13, EGF, TGF-α, HB-EGF, amphiregulin, betacellulin, epiregulin, epigen, or TNF-beta.

47. The method of claim 46, wherein the protein that is inducibly expressed and stimulates an epithelial-to-mesenchymal transition in H358 cells is Zeb-1, Snail, or constitutively active TGF-beta.

48. The method of claim 45, wherein a Tet-regulated promoter is used to inducibly express the protein that stimulates an epithelial-to-mesenchymal transition in H358 cells.

49. The method of claim 48, wherein the Tet-regulated promoter is a Tet-on system.

50. The method of claim 45, wherein the biomarker whose level is indicative of the EMT status of the sample tumor cells is an epithelial cell biomarker.

51. The method of claim 50, wherein the epithelial cell biomarker is E-cadherin, cytokeratin 8, cytokeratin 18, P-cadherin or erbB3.

52. The method of claim 45, wherein the epithelial cell biomarker whose level is indicative of the EMT status of the sample tumor cells is the activity of an epithelial biomarker gene promoter.

53. The method of claim 52, wherein the activity of the epithelial biomarker gene promoter is assessed by inclusion of a epithelial biomarker gene promoter-reporter gene construct in the engineered H358 cells such that said promoter reporter activity can be monitored by reporter gene level or activity.

54. The method of claim 53, wherein epithelial biomarker gene promoter-reporter gene construct is an E-cadherin promoter-firefly luciferase construct.

55. The method of claim 45, wherein the biomarker whose level is indicative of the EMT status of the sample tumor cells is a mesenchymal cell biomarker.

56. The method of claim 55, wherein the mesenchymal cell biomarker is vimentin, fibronectin, N-cadherin, CDH1 methylation, zeb1, twist, FOXC2 or snail.

57. The method of claim 45, wherein the mesenchymal cell biomarker whose level is indicative of the EMT status of the sample tumor cells is the activity of a mesenchymal biomarker gene promoter.

58. The method of claim 57, wherein the activity of the mesenchymal biomarker gene promoter is assessed by inclusion of a mesenchymal biomarker gene promoter-reporter gene construct in the engineered H358 cells such that said promoter reporter activity can be monitored by reporter gene level or activity.

59. The method of claim 58, wherein mesenchymal biomarker gene promoter-reporter gene construct is a vimentin promoter-firefly luciferase construct.

60. The method of claim 45, wherein the sample of cells of the epithelial tumor cell line H358, which have been engineered to inducibly express a protein that stimulates an epithelial to mesenchymal transition in H358 cells, is a xenograft growing in an animal.

61. A method of identifying an agent that inhibits tumor cells that have undergone an epithelial-to-mesenchymal transition, comprising contacting a sample of cells of the epithelial tumor cell line H358, which have been engineered to inducibly express a protein that stimulates an epithelial-to-mesenchymal transition in H358 cells, with a compound that induces the expression of said protein such that an epithelial-to-mesenchymal transition is induced in the cells,
    contacting the sample of cells with a test agent to be screened,
    determining whether the test agent inhibits mesenchymal-like H358 cell growth,
    and thus determining whether it is an agent that inhibits the growth of tumor cells that have undergone an epithelial-to-mesenchymal transition.

62. The method of claim 61, wherein the protein that is inducibly expressed and stimulates an epithelial-to-mesenchymal transition in H358 cells is Zeb-1, Snail, constitutively active TGF-beta, co-expressed HGF and OSM, TNF-alpha, constitutively active cMET receptor, activated Src kinase, v-Src, Src Y530F mutant, IL-4, IL-13, EGF, TGF-α, HB-EGF, amphiregulin, betacellulin, epiregulin, epigen, or TNF-beta.

63. The method of claim 61, wherein the protein that is inducibly expressed and stimulates an epithelial-to-mesenchymal transition in H358 cells is Zeb-1, Snail, or constitutively active TGF-beta.

64. The method of claim 61, wherein a Tet-regulated promoter is used to inducibly express the protein that stimulates an epithelial-to-mesenchymal transition in H358 cells.

65. The method of claim 64, wherein the Tet-regulated promoter is a Tet-on system.

66. A method of identifying an agent that stimulates mesenchymal-like tumor cells to undergo a mesenchymal-to-epithelial transition, comprising
    contacting a sample of cells of the epithelial tumor cell line H358, which have been engineered to inducibly express a protein that stimulates an epithelial-to-mesenchymal transition in H358 cells, with a compound that induces the expression of said protein such that an epithelial-to-mesenchymal transition is induced in the cells,
    contacting the sample of cells with a test agent to be screened,
    determining whether the test agent stimulates the mesenchymal-like H358 cells in the sample to undergo a mesenchymal-to-epithelial transition, by comparing the level of a biomarker whose level is indicative of the EMT status of the sample tumor cells to the level of the same biomarker in an identical sample of mesenchymal-like H358 cells not contacted with the test agent,
    and thus determining whether the test agent is an agent that stimulates mesenchymal-like tumor cells to undergo a mesenchymal-to-epithelial transition.

67. The method of claim 66, wherein the protein that is inducibly expressed and stimulates an epithelial-to-mesenchymal transition in H358 cells is Zeb-1, Snail, constitutively active TGF-beta, co-expressed HGF and OSM, TNF-alpha, constitutively active cMET receptor, activated Src kinase, v-Src, Src Y530F mutant, IL-4, IL-13, EGF, TGF-α, HB-EGF, amphiregulin, betacellulin, epiregulin, epigen, or TNF-beta.

68. The method of claim 66, wherein the protein that is inducibly expressed and stimulates an epithelial-to-mesenchymal transition in H358 cells is Zeb-1, Snail, or constitutively active TGF-beta.

69. The method of claim 66, wherein a Tet-regulated promoter is used to inducibly express the protein that stimulates an epithelial-to-mesenchymal transition in H358 cells.

70. The method of claim 69, wherein the Tet-regulated promoter is a Tet-on system.

71. The method of claim 66, wherein the biomarker whose level is indicative of the EMT status of the sample tumor cells is an epithelial cell biomarker.

72. The method of claim 71, wherein the epithelial cell biomarker is E-cadherin, cytokeratin 8, cytokeratin 18, P-cadherin or erbB3.

73. The method of claim 66, wherein the epithelial cell biomarker whose level is indicative of the EMT status of the sample tumor cells is the activity of an epithelial biomarker gene promoter.

74. The method of claim 73, wherein the activity of the epithelial biomarker gene promoter is assessed by inclusion of a epithelial biomarker gene promoter-reporter gene construct in the engineered H358 cells such that said promoter reporter activity can be monitored by reporter gene level or activity.

75. The method of claim 74, wherein epithelial biomarker gene promoter-reporter gene construct is an E-cadherin promoter-firefly luciferase construct.

76. The method of claim 66, wherein the biomarker whose level is indicative of the EMT status of the sample tumor cells is a mesenchymal cell biomarker.

77. The method of claim 76, wherein the mesenchymal cell biomarker is vimentin, fibronectin, N-cadherin, CDH1 methylation, zeb1, twist, FOXC2 or snail.

78. The method of claim 77, wherein the mesenchymal cell biomarker whose level is indicative of the EMT status of the sample tumor cells is the activity of a mesenchymal biomarker gene promoter.

79. The method of claim 78, wherein the activity of the mesenchymal biomarker gene promoter is assessed by inclusion of a mesenchymal biomarker gene promoter-reporter gene construct in the engineered H358 cells such that said promoter reporter activity can be monitored by reporter gene level or activity.

80. The method of claim 79, wherein mesenchymal biomarker gene promoter-reporter gene construct is a vimentin promoter-firefly luciferase construct.

81. The method of claim 66, wherein the sample of cells of the epithelial tumor cell line H358, which have been engineered to inducibly express a protein that stimulates an epithelial-to-mesenchymal transition in H358 cells, is a xenograft growing in an animal.

82. A tumor cell preparation for use in the identification of anti-cancer agents, wherein said tumor cell preparation comprises:
    a sample of cells of the epithelial tumor cell line H358, which have been engineered to inducibly express a protein that stimulates an epithelial-to-mesenchymal transition in H358 cells.

83. The tumor cell preparation of claim 82, wherein the protein that is inducibly expressed and stimulates an epithelial-to-mesenchymal transition in H358 cells is Zeb-1. Snail, constitutively active TGF-beta, co-expressed HGF and OSM, TNF-alpha, constitutively active cMET receptor, activated Src kinase, v-Src, Src Y530F mutant, IL-4, IL-13, EGF, TGF-α, HB-EGF, amphiregulin, betacellulin, epiregulin, epigen, or TNF-beta.

84. The tumor cell preparation of claim 82, wherein the protein that is inducibly expressed and stimulates an epithelial-to-mesenchymal transition in H358 cells is Zeb-1, Snail, or constitutively active TGF-beta.

85. The tumor cell preparation of claim 84, wherein a Tet-regulated promoter is used to inducibly express the protein that stimulates an epithelial-to-mesenchymal transition in H358 cells.

86. The tumor cell preparation of claim 85, wherein the Tet-regulated promoter is a Tet-on system.

87. The tumor cell preparation of claim 82, additionally comprising a stably incorporated epithelial and/or mesenchymal biomarker gene promoter-reporter gene construct in the engineered H358 cells such that said promoter reporter activity can be monitored by reporter gene level or activity.

88. The tumor cell preparation of claim 82, in which the H358 cells have been additionally engineered to inducibly express a reporter gene, such that reporter gene level or activity can be used to monitor EMT induction.

89. The tumor cell preparation of claim 82, wherein the sample of cells of the epithelial tumor cell line H358, which have been engineered to inducibly express a protein that stimulates an epithelial-to-mesenchymal transition in H358 cells, is a xenograft growing in an animal.

90. The method of claim 4, wherein the single-protein ligand that induces an epithelial-to-mesenchymal transition in H358 cells is TGFbeta, optionally with OSM or HGF.

91. The method of claim 16, wherein the single-protein ligand that induces an epithelial-to-mesenchymal transition in H358 cells is TGFbeta, optionally with OSM or HGF.

92. The method of claim 27, wherein the single-protein ligand that induces an epithelial-to-mesenchymal transition in H358 cells is TGFbeta, optionally with OSM or HGF.

93. The method of claim 41, wherein the single-protein ligand that induces an epithelial-to-mesenchymal transition in H358 cells is TGFbeta, optionally with OSM or HGF.

* * * * *